(12) United States Patent
Kirchgessner et al.

(10) Patent No.: US 6,692,934 B1
(45) Date of Patent: Feb. 17, 2004

(54) ORGANIC ANION TRANSPORT PROTEINS

(75) Inventors: Todd G. Kirchgessner, North Wales, PA (US); Bonnie Hsiang, Trenton, NJ (US); Yingjie Zhu, Killingworth, CT (US); Yuli Wu, Newtown, PA (US); Zhaoqing Wang, Piscataway, NJ (US); Jean S. Lynch, Ringoes, NJ (US); Xin Huang, Cranbury, NJ (US); Wen-Pin Yang, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/575,081

(22) Filed: May 19, 2000

Related U.S. Application Data

(60) Provisional application No. 60/135,081, filed on May 20, 1999.

(51) Int. Cl.[7] .......................... C12P 21/06; C12N 15/00; C07H 21/04; C07K 1/00; G01N 33/567
(52) U.S. Cl. .................. 435/69.1; 435/91.1; 435/320.1; 536/23.1; 536/23.5; 530/350; 436/504
(58) Field of Search ............................... 435/69.1, 91.1, 435/320.1; 530/350

(56) References Cited

U.S. PATENT DOCUMENTS 6,020,143 A * 2/2000 George-Hyslop et al. .... 435/7.1

OTHER PUBLICATIONS

Hillier et al., 1995, Genbank ACC No. T73863.*
Hagenbuch, B., et al., Proc. Natl. Acad. Sci. vol. 88, Dec. 1991, pp. 10629–10633.
Hagenbuch,B., et al., The American Society for Clinical Investigation, Inc. vol. 93, Mar. 1994, pp. 1326–1331.
Meier, P.J., et al., Hepatology vol. 26, No. 6, 1997, pp. 1667–1677.
Jacquemin, E., et al., Proc. Natl. Acad. Sci. vol. 91, Jan. 1994, pp. 133–137.
Noe, B.A., et al., Proc. Nat;. Acad. Sci. vol. 94, Sep. 1997, pp. 10346–10350.
Abe, T., et al., J. Biol. Chem. vol. 273, No. 18, (1998), pp. 11395–11401.
Bossuyt, X., et al., J. Pharmacol. Exp. Ther. vol. 276, (1996), pp. 891–6.
Bossuyt, X., et al., J. Hepatol. vol. 25, (1996) pp. 733–8.
Kanai, N., et al., Am. J. Physiol. vol. 270, (1996), pp. F319–F325.
Kanai, N., et al., Am. J. Physiol. vol. 270, (1996), pp. F326–F331.
Kontaxi, M., et al., J. Pharmacol. Exp. Ther. vol. 279, (1996), pp. 1507–1513.
Li, L., et al., J. Biol. Chem. vol. 273, No. 26 (1998), pp. 16184–16191.
Kullak–Ublick, G.A., et al., Gastroenterology vol. 109, No. 4, (1995), pp. 1274–1282.
Kullak–Ublick, G.A., et al., Hepatology vol. 20, No. 2, (1994), pp. 411–416.
Kullak–Ublick, G.A., et al., FEBS Lett., vol. 424, (1998), pp. 173–176.
Wolkoff, A.W., Semin. Liver Dis., vol. 16, No. 2, (1996), pp. 121–127.
Abe, T., et al., J. Biol. Chem., vol. 273, No. 35 (1998), pp. 22395–22401.

* cited by examiner

*Primary Examiner*—John Ulm
*Assistant Examiner*—Olga N. Chernyshev
(74) *Attorney, Agent, or Firm*—Audrey F. Sher

(57) ABSTRACT

The current invention discloses nucleic acid and amino acid sequences for novel organic anion transfer proteins ("OATPs"). The invention encompasses the OATPs described herein, together with vectors containing the cDNA sequences, host cells containing the vectors and polypeptides having all or part of an OATP. Also encompasses are uses for OATPs for targeting drugs to specific organs and for modulating the concentration of endogenous substrates.

7 Claims, 8 Drawing Sheets

Tissue Key

H: heart
B: brain
P: placenta
L: lung
Lv: liver
Sm: skeletal muscle
K: kidney
Pn: pancreas S: spleen
Ty: thymus
Pr: prostate
T: testis
O: ovary
Si: small intestine
C: colon
Bl: peripheral blood leukocytes

```
                                                                          80
roatp2      ..........  ..........  ..........  ..........  ..........  ..........  ..........  ..........
roatp3      ..........  ..........  ..........  ..........  ..........  ..........  ..........  ..........
rOAT-K1     ..........  ..........  ..........  ..........  ..........  ..........  ..........  ..........
roatp1      ..........  ..........  ..........  ..........  ..........  ..........  ..........  ..........
hOATP       ..........  ..........  ..........  ..........  ..........  ..........  ..........  ........m
hOATP-RP5   ..........  ..........  ..........  ..........  ..........  ..........  ..........  ..........
hOATP2      ..........  ..........  ..........  ..........  ..........  ..........  ..........  ..........
hOATP-RP3   ..........  ..........  ..........  ..........  ..........  ..........  ..........  ..........
hPGT        ..........  ..........  ..........  ..........  ..........  ..........  ..........  ..........
hOATP-RP2   mdegtglqpg  ageqleapat  aeavqercep  etlrskslpv  lssascrpsl  sptsgdanpa  fgcvdssghq  elkqgpnpla
hOATP-RP4   ..........  ..........  ..........  ..........  ..........  ..........  ..........  ..........
hOATP-RP1   mplhqlgdkp  ltfpspnsam  englđhtpps  rraspgtpls  pgslrsaahs  pldtskqplc
Consensus   ----------  ----------  ----------  ----------  ----------  ----------  ----------  ----------

160
roatp2      ..........  ........k   sEkrvAthg.  .vrCFakIKm  FLLALtcAyv  sksLs.GtYM  nSmLTQIERq
roatp3      .........m  G.......e   tEkrvAthe.  .vrCFskIKm  FLLALtwAyv  sqsLs.GiYM  ntmLTQIERq
rOAT-K1     .........m  G.......d   lEkgaAthg.  .agCFakIKv  FLmALtcAyv  sksLs.GtfM  sSmLTQIERq
roatp1      .........m  e.......e   tEkkiAtqe.  .grlFskmKv  FLLsLtcAcl  tksLs.GvYM  nSmLTQIERq
hOATP       .........m  e.......e   tEkriethr.  .irClsklKm  FLLAitcAfv  sktLs.GsYM  nSmLTQIERq
hOATP-RP5   dtsskeniql  fcktsvq.pv  Gr.....psfk  tEypsseek.  .qpCcgelKv  FLcALsfvyf  akaLa.egYl  kStiTQIERR
hOATP2      ..........  ..mdqmq.hl  n.......kt  aEaqpsenkk  .trycnglkm  FLaALslsfi  aktLg.aiiM  kSsiihIERR
hOATP-RP3   mqgkkpggss  gggrsge.lq  G.......de  aqrnkkkkkk  .vsCFsniKi  FLvsecalml  aqgtv.GaYl  vSvLTtlERR
hPGT        .........mg  llpklgv.sq  G.......sd  tstsrAgrca  .rsvFgniKv  FvLcqgllql  cqlLy.sayf  kSsLTtiEkR
hOATP-RP2   ..........  .mgtent.pg  G.......k  aspdpqdvr.  .psvFhniKl  FvLchsllql  aqlmi.sgYl  kSsistvEkR
hOATP-RP4   pspsapstsa  glgdcnh.rv  dlsktfsvss  alamlgerrc  lyvvltdsrc  Flvcmcfltf  iqaLmvsgYl  sSviTtIERR
hOATP-RP1   qlwaekhgar  gthevryxsa  G.......  qsv acgwwAfapp  clqvlntpKg  iLfflcaAaf  lggmtvngfi  ntviTslERR
Consensus   ----------  G---------  G-------  E---A----  ---CF---IK-  FLLAL--A--  ---L---G-YM  -S-LTQIERR
```

FIG. 3A

```
          161                                                                              240
roatp2    FgIptSiVGL lnGSFEIGNL LLIifVSYFG tKLHRPimIG vGCavMGLGc fLisLPHFLM GqYEYEt.... ilptsNvsSn
roatp3    FdIpisIVGf lnGSFEIGNf LLIifVSYFG tKLHRPimIG vGCviMGLGc fLmsLPHFLM GrYEYEtt... isptsNlsSn
rOAT-K1   FgIptaiVGf lnGSFEIGNL LLIifVSYFG mKLHRPivIG vGCavMGLGc fiisLPHFLM GrYEYEtt... ilptsNlsSn
roatp1    FdIstSvaGL lnGSFEIGNL ffIvFVSYFG tKLHRPvvIG iGCviMGLGc lLmsLPHFfM GrYEYEtt... isptgNlsSn
hOATP     FnIptSlVGf lnGSFEIGNL LLIifVSYFG tKLHRPimIG iGCvvMGLGc fLksLPHFfM nqYEYEst... vsvsgNlsSn
hOATP-RP5 FdIpSSlVGv ldGSFEIGNL LvItfVSYFG aKLHRPkiIG aGCviMGvGt lLiamPqFfM eqYkYEr... yspssNstls
hOATP2    FeIsSSlVGf ldGSFEIGNL LvIvfVSYFG sKLHRPklIG iGCfiMGiGg vLtaLPHFfM GyYrYsketn idsseNstSt
hOATP-RP3 FnlqSadVGv lasSFEIGNL aLIlfVSYFG arghRPrlIG cGgivMaLGa lLsaLPeFlt hqYkYEag.. .eirwgaegr
hPGT      FglsSSssGL IsslnEIsNa iLIiFVSYFG srvHRPrlIG iGglflaaGa filtLPHFls epYQytla.. .stgnNsrlq
hOATP-RP2 FglsSqtsGL lasfnEvGNt aLIvFVSYFG srvHRPrmIG yGailvaLag lLmtLPHFis epYrYdnts. .pedmpqdfk
hOATP-RP4 yslkSSesGL lvscFdIGNL vvvFVSYFG grgrRPlwla vGglliafGa aLfaLPHFis ppYqige... ..lnasapnd
hOATP-RP1 ydlhSyqsGL lasSydIaac LcltFVSYFG gsgHkPrwlG wGvllMGtGs lvfaLPHFta GrYEvEl... ......dagvr
Consensus F-I-SS-VGL I-GSFEIGNL LLI-FVSYFG -KLHRP---IG -GC---MGLG- -L--LPHFLM G--YEYE--- -----N--S-

241                                                                              320
roatp2    sffCveNrSq ......tLnPt qD..psECvK Emk.SLMWIY VlVG...NIi RGIGETPImP LGISYIeDFA KsENSPLYIG
roatp3    sfLCmeNrSq ......tLkPt qD..paECiK Emk.SLMWIY VlVG...NIi RGIGETPImP LGISYIeDFA KsENSPLYIG
rOAT-K1   sfLCmeNqtq ......tLnPa qD..paECvK Evk.SLMWIY VlVG...NIi RGIGETPImP LGvSYIenFA KsENSPLYIG
roatp1    sfLCmeNrtq ......tLkPt qD..paECvK Emk.SLMWIc VmVG...NIi RGIGETPIvP LGISYIeDFA KsENSPLYIG
hOATP     sfLCmeNgtq ......iLrPt qD..psECTK Evk.SLMWvY VlVG...NIv RGmGETPIlP LGISYIeDFA KfENSPLYIG
hOATP-RP5 ispCllesSs qlpvsvmeks kskisnECev dts.SsMMIY VflG...NIL RGIGETPIqP LGIaYlDDFA sedNaafYIG
hOATP2    lstCliNqil s....lnras peivgkgClk Esg.SyMMIY VfmG...NmL RGIGETPIvP LGlSYIDDFA KeghSsLYIG
hOATP-RP3 .dvCaaNgSg g......degPd pD...liCrn rta.tnMmyl lliGa..qvL RGIGETPIvP LGvSYIDDhv rrkdSsLYIG
hPGT      aeLCqkhwqd ......LpPs kchsttqnpq ket.SsMwgl mvVa...qlL lGIGaTPvqP fGISYvDDFs epsNSPLYIs
hOATP-RP2 asLClpttSa p....asaPs ng..ncssyt Etq.hLsvvg imfva..qtL aGIGtvPIqP LGvGgvPIqP fGISYIvDFA hnsNSPLYIG
hOATP-RP4 .gLCqqgnSt a......tLeP. p.....aCpK dsggnnhwvY lalficaqIL iGmGsTPIyt LGptYlDDnv KkENSsLYla
hOATP-RP1 ..tCpaN... ..........P. .....gavCad stsglsryql Vfmlg..qfL hGvGaTPlyt LGvtYlDenv KsscSPvYIa
Consensus --LC--N-S- -------L-P- --D-----EC-K E---SLMWIY V-VG---NIL RGIGETPI-P LGISYIDDFA K-ENSPLYIG
```

FIG. 3B

```
            321
roatp2      ILeTgmtiGP  liGlLLaSsC  AnIYVDiesV  NTDdLtITPt  DtRWVGAWWi  GFLvCAGvni  LtsFPFFFFP  KtLP...KeG       400
roatp3      ILeTgkvfGP  ivGlLLGSfC  AsIYVDtGsV  NTDdLtITPt  DtRWVGAWWi  GFLiCAGvni  LssIPFFFFP  KtLP...KeG
rOAT-K1     ILeTgkmiGP  ifGlLLGSfC  AsIYVDtGsV  NTDdLtITPt  DiRWVGAWWi  GFLvCAGvni  LiSIPFFFFP  KtLP...KeG
roatp1      ILemgkvaGP  ifGlLLGSyC  AqIYVDiGsV  NTDdLtITPs  DtRWVGAWWi  GFLvCAGvni  LtSIPFFFLP  KaLP...KkG
hOATP       lveTgaiiGP  liGfLLaSfC  AnvYVDtGfV  NTDdLtITPt  DtRWVGAWWf  GFLiCAGvnv  LtaIPFFFlP  ntLP...KeG
hOATP-RP5   cvqfTvaiiGP iifGfLLGSlC  AklYVDiGfV  NlDhitITPk  DPqWVGAWW1  GyLiagiisl  LaavPFwylP  KsLP...rsq
hOATP2      ILnaiamiGP  iiGftLGSlf  skmYVDiGyV  dlstirITPt  DsRWVGAWW1  nFLvsglfsi  isSIPFFFlP  qtpn...Kpq
hOATP-RP3   ILfTmlvfGP  acGfiLGSfC  tkIYVDavfi  dTsnLdITPd  DPRWiGAWWg  GFLlCgallf  fsSllmFgFP  qsLPphsdpa
hPGT        ILfaisvfGP  afGyLLGSim  lqIfVDyGrV  NTaavnlvPg  DPRWiGAWW1  GLlissallv  LtsFPFFFFP  ramP....iG
hOATP-RP2   ILfavtmmGP  glafgLGSlm  lrlYVDinqm  peggislTik  DPRWiGnWWs  GFLiaAGava  LaaIPyFFFP  KemPkekrel
hOATP-RP4   Imyvmgalp   avGyLLgGll  igfYVDp...  .rnpvhldqn  DPRFiGnWWs  GFLlCAiamf  LvifPmFtFP  KkLPprhkkk
hOATP-RP1   IfyTaailGP  aaGyLiGgal  lnIYtemG..  ..rrtelTte  sPlWVGAWWv  GFLgsgaaaf  ftavPilgyP  rqLP....gs
Consensus   IL-T----GP  --G-LLGS-C  A-IYVD-G-V  NTD-L-ITP-  DPRWVGAWW-  GFL-CAG---  L-SIPFFFFP  K-LP----K-G 401                                                                                              480
lq..enVdgt  e.........n akekkhrkka  k..........                                                  eekrgit  KDFFvfmKsL  scNPiYmLfi  LisVlQfNaf
lq..ddVdgt  n.........n dkeekhreka  k..........                                                  eenrgit  KDFlpfmKsL  scNPiYmLli  LtsVlQiNaf
lq..enVdgt  e.........n akeestekrp  r..........                                                  kknrgit  KDFfpflKsp  vlqPdlhavh  pykVlQvNaf
qq..enVavt  k.........d gkvekyggqa  r..........                                                  eenlgit  KDFltfmKrL  fcNPiYmLfi  LtsVlQvNgf
le..tnadii  k.........n enedkqkeev  k..........                                                  kekygit  KDFlpfmKsL  scNPiYmLfi  LvsViQfNaf
sr..edsnss  sekskfii.d  dhtdyqtpqg  en.........                                                  akimema  rDFlpslKnL  fgNPvYfLyl  ctstvQfNsl
ke..rkasls  lhvletn..d  ekdqtanltn qg...........                                                 knitknv  tgFfqsfKsi  LtNPlYvmfv  LltllQvssy
mes.eqamls  ereyerpkps  ngvlrhplep dss..........                                                 ascfqql  rvipkvtKhL  LsNPvftcii  Laacmeiavv
ak...rapat  a.........d earkleeaks r..........                                                   gslvdfi  KrFpciflrL  LmNslfvLvv  Laqctfssvi
qfr.rkVlav  tdsparkgkd  spskqspges tkkqdglvqi  apnltviqfi                                         KvFprvllqt  LrhPiflLvv  LsqVclssma
kkkkfsVdav  sddvlkeks   nnseqadkkv ss..........                                                   mgfgkdv  rDlpraavri  LsNmtflfvs  Lsytaesaiv
qr..yaVmra  a..em...h   qlkdssrgea sn..........                                                   pdfgkti  rDlplsiwlL  LkNPtfiLlc  Lagateatli
Consensus   ------V---  ----------  ----------  ----------                                        -------  KDF----K-L  L-NP-Y-L--  L--V-Q-N--
```

FIG. 3C

```
                481                                                                                  560
roatp2      insfTFmPKY LEQQYGkSta evvFLmGlym LPpiCiGyli GGlIMKKFKv tVkkAAhLAf wlcLseYLls flsyvmtCdN
roatp3      inmfTFLPKY LEQQYGkSta evvlLiGvyn LPpiCiGyll iGfIMKKFKi tVkkAAymAf clSLfeYLly flhFmitCdN
rOAT-K1     niyfsFLPKY LEnQYGkSta eviFLmGvyn LPaiCiGyli aGfmMKKFKi tVktAAfLrf clSLseYsfg fcnFlitCdN
roatp1      inkfTFLPKY LEQQYGkSta eAiFLiGvys LPpiCiGyli GGfIMKKFKi tVkkAAyLAf clSvfeYLLf lchFmltCdN
hOATP       vnmisFmPKY LEQQYGisSs dAiFLmGiyn LPpiCiGyii tVkqAAhigc wlSLleYLly flsFlmtCeN
hOATP-RP5   fGmvTykPKY iEQQYGqSsS rAnFviGlin iPavalGifs GGivMKKFri sVcgAAkLyl gsSvfgYLLf lslFalgCeN
hOATP2      iGafTyvfKY vEQQYGqpsS kAnillGvit iPifasGmfl GGyIkKKFKl ntvgiAkfsc ftavmslsfy llyFfilCeN
hOATP-RP3   aGfaaFLgKY LEQQfnltts sAnqlLGmta iPcaClGifl GGllvKKlsl salgAirmAm lvnLvstacy vsflflgCdt
hPGT        aGlsTFLnKf LEkQYGtSaa yAnFLiGavn LPaaalGmlf GGilMKrFvf slqtipriAt tiitismiLc vplFfmgCst
hOATP-RP2   aGmaTFLPKf LErQfsitaS yAnlLiGcls fPsvivGivv GGvlvKrlhl gpvcgaLcl lgmLlcliffs lplFfigCss
hOATP-RP4   tafiTFiPKf iEsQfGipaS nAsiytGvii vPsagvGivl GGyIikKLKl garesAkLAm icSgvsLlcf stlFivgCes
hOATP-RP1   tGmsTFsPKf LEsQfslSaS eAatLfGylv vPagggGtfl GGffvnKlrl rgsavikfcl fctvvsllg. ilvFslhCps
Consensus   -G---TFLPKY LEQQYG-S-S -A-FL-G--- LP---C--G--- GG-IMKKFK- -V--AA-LA- --SL--YLL- ---F----C-N 561                                                                                  640
roatp2      fpVAGLTtsY eGvqhqlyvE nkvlADCNtr CnCstntWdP VCG.dNGlaY mSACLAGCe. ..kSvGTGtN mVFq.NCSCI
roatp3      fpVAGLTaly eGvhhplyvE nkvlADCNrg CSCstnsWdP VCG.dNGlaY mSACLAGCk. ..kSvGTGtN mVFq.NCSCI
rOAT-K1     vpVAGLTnsY erdqkplylE nnvlADCNtr CSCltktWdP VCG.dNGlaY mSACLAGCe. ..kSvGTGtN mVFh.NCSCI
roatp1      aaVAGLTtsY kGvqhqlhvE skvlADCNtr CSCstntWdP VCG.dNGvaY mSACLAGCk. ..kfvGTGtN mVFq.dcSCI
hOATP       ssVvgintsY eGipqdlyvE ndifADCNvd CnCpskiWdP VCG.nNGlsY vCg.nNGlsY lSACLAGCe. ..tSiGTGiN mVFq.NCSCI
hOATP-RP5   sdVAGLTvsY qgtkpvsyhE ralfsDCNsr CkCsetkWeP mCG.eNGitY vSACLAGCq. ..tSnrsGxN iiFy.NctCv
hOATP2      ksVAGLTmtY dGnnpvtshr dvplsyCNsd CnCdesqWeP VCG.nNGitY iSpCLAGCk. ..sSsGnkkp iVFy.NCSCl
hOATP-RP3   gpVAGVTvpY .Gnstapgsa ldpyspCNnn CeCqtdsftP VCG.adGitY lSACfAGCn. ..stnlTG.. ......CaCl
hPGT        ptVAevypps ..tss.sihp qs..paCrrd CSCpdsifhP VCG.dNGieY VCdpstrveY inmSsaTskq liyl.NCSCv
hOATP-RP2   hqiAGiThqt ...sahpglE ls..psCmea CSCpldgfnP VCG.sdGitY itpChAGCss wvvqdaldns qVFytNCSCv
hOATP-RP4   inlgGinipY ttgpsltmph rnltgsCNvn CgCkiheyeP VCG.sdGitY fnpCLAGCv. ..nSgnlstg irnyteCtCv
hOATP-RP1   vpmAGvTaSY .Ggsllpegh lnltApCNaa CSCqpehysP VCG.sdGlmY fslChAGCpa atetnvdGqk .Vyr.dCSCI
Consensus   --VAGLT-SY -G------E ----ADCN-- CSC----W-P VCG--NG--Y -SACLAGC-- ---S-GTG-N -VF--NCSCI
```

```
         801                                                                                    880
roatp2   R.......tfq fPgd...Ies Sk....tdha emkltlKESe cTevlrs.kv t..eD..............
roatp3   R.......Kfq fPge...IdS SE....tela emkitvKkse cTdvHgspqv e..nDgElkT rl..........
rOAT-K1  R.......Kfs lPgk...InS SE....meia emklteKESq cTdvHrnpkf k..nDgElkT kl..........
roatp1   R.......Kfq fPgd...IdS Sa....tdht emmlgeKESe hTdvHgspqv e..nDgElkT kl..........
hOATP    R.......Kch lPge...naS Sg....teli etkvkgKEne ckdiyqkstv l..kDdElkT kl..........
hOATP-RP5 k.......Kny vskhrsfItk rE.....rtmv strfq.KEny tTsdHllqpn y..wpgke.T ql.........
hOATP2   k.......Kky qekd...Ina SE....ngsv mdean.lEsl nknkHfvpsa g..aDsEthc ............
hOATP-RP3 Rkny....Kry iknhegglst SEff.astlt ldnlgrdpvp anqtHrtkfi ynleDhEwce nmesvl......
hPGT     k.......Knk .eyn...vqk aa....gli. .......... .......... .......... ............
hOATP-RP2 Rqqd....Kea rtke...srS Sp....ave qqllvsgpgk kpedsrv... .......... ............
hOATP-RP4 kykedglqrr rqrefplstv SErvghpdna rtrscpafst qgefHeetgl qkgiqcaaqT ypgpfpeais ssadpglees
hOATP-RP1 k.........  Pls...eS Sd...gletc lpsqssapds aTdsqlqssv .......... ............
Consensus R------K-- -P------I-S SE------- ------KES- -T--H---- ----D-E--T ------------

881
roatp2    .........
roatp3    .........
rOAT-K1   .........
roatp1    .........
hOATP     .........
hOATP-RP5 .........
hOATP2    .........
hOATP-RP3 .........
hPGT      .........
hOATP-RP2 .........
hOATP-RP4 paalepxs
hOATP-RP1 .........
Consensus ---------
```

FIG. 3F

SEQUENCE LISTING

<160> NUMBER OF SEQ ID NOS: 29

<210> SEQ ID NO 1
<211> LENGTH: 2830
<212> TYPE: DNA
<213> ORGANISM: Homo sapiens

<400> SEQUENCE: 1

```
cggacgcgtg ggcggacgcg tgggtcgccc acgcgtccga cttgttgcag ttgctgtagg        60
attctaaatc caggtgattg tttcaaactg agcatcaaca acaaaaacat ttgtatgata       120
tctatatttc aatcatggac caaaatcaac atttgaataa aacagcagag gcacaacctt       180
cagagaataa gaaaacaaga tactgcaatg gattgaagat gttcttggca gctctgtcac       240
tcagctttat tgctaagaca ctaggtgcaa ttattatgaa aagttccatc attcatatag       300
aacggagatt tgagatatcc tcttctcttg ttggttttat tgacggaagc tttgaaattg       360
gaaatttgct tgtgattgta tttgtgagtt actttggatc caaactacat agaccaaagt       420
taattggaat cggttgtttc attatgggaa ttggaggtgt tttgactgct ttgccacatt       480
tcttcatggg atattacagg tattctaaag aaactaatat cgattcatca gaaaattcaa       540
catcgacctt atccacttgt ttaattaatc aaattttatc actcaataga gcatcacctg       600
agatagtggg aaaaggttgt ttaaaggaat ctgggtcata catgtggata tatgtgttca       660
tgggtaatat gcttcgtgga ataggggaga ctcccatagt accattgggg cttttcttaca      720 ttgatgattt cgctaaagaa ggacattctt ctttgtattt aggtatattg aatgcaatag       780
caatgattgg tccaatcatt ggctttaccc tgggatctct gttttctaaa atgtacgtgg       840
atattggata tgtagatcta agcactatca ggataactcc tactgattct cgatgggttg       900
gagcttggtg gcttaatttc cttgtgtctg gactattctc cattatttct tccataccat       960
tctttttctt gccccaaact ccaaataaac cacaaaaaga aagaaaagct tcactgtctt      1020
tgcatgtgct ggaaacaaat gatgaaaagg atcaaacagc taatttgacc aatcaaggaa      1080
aaaatattac caaaaatgtg actggttttt tccagtcttt taaaagcatc cttactaatc      1140
ccctgtatgt tatgtttgtg cttttgacgt tgttacaagt aagcagctat attggtgctt      1200
ttacttatgt cttcaaatac gtagagcaac agtatggtca gccttcatct aaggctaaca      1260
tcttattggg agtcataacc ataccctattt ttgcaagtgg aatgttttta ggaggatata      1320
tcattaaaaa attcaaactg aacaccgttg gaattgccaa attctcatgt tttactgctg      1380
tgatgtcatt gtccttttac ctattatatt ttttcatact ctgtgaaaac aaatcagttg      1440
ccggactaac catgaccat gatggaaata atccagtgac atctcataga gatgtaccac      1500
```

-continued

```
tttcttattg caactcagac tgcaattgtg atgaaagtca atgggaacca gtctgtggaa    1560
acaatggaat aacttacatc tcaccctgtc tagcaggttg caaatcttca agtggcaata    1620
aaaagcctat agtgttttac aactgcagtt gtttggaagt aactggtctc cagaacagaa    1680
attactcagc ccatttgggt gaatgcccaa gagatgatgc ttgtacaagg aaattttact    1740
tttttgttgc aatacaagtc ttgaatttat ttttctctgc acttggaggc acctcacatg    1800
tcatgctgat tgttaaaatt gttcaacctg aattgaaatc acttgcactg ggtttccact    1860
caatggttat acgagcacta ggaggaattc tagctccaat atattttggg gctctgattg    1920
atacaacgtg tataaagtgg tccaccaaca actgtggcac acgtgggtca tgtaggacat    1980
ataattccac atcattttca aggtctact tgggcttgtc ttcaatgtta agagtctcat    2040
cacttgtttt atatattata ttaatttatg ccatgaagaa aaaatatcaa gagaaagata    2100
tcaatgcatc agaaaatgga agtgtcatgg atgaagcaaa cttagaatcc ttaaataaaa    2160
ataaacattt tgtcccttct gctggggcag atagtgaaac acattgttaa ggggagaaaa    2220
aaagccactc tgcttctgt gtttccaaac agcattgcat tgattcagta agatgttatt    2280
tttgaggagt tcctggtcct ttcactaaga atttccacat cttttatggt ggaagtataa    2340
ataagcctat gaacttataa taaacaaac tgtaggtaga aaaatgaga gtactcattg    2400 ttacattata gctacatatt tgtggttaag gttagactat atgatccata caaattaaag    2460
tgagagacat ggttactgtg taataaaaga aaaatactt gttcaggtaa ttctaattct    2520
taataaaaca aatgagtatc atacaggtag aggttaaaaa ggaggagcta gattcatatc    2580
ctaagtaaag agaaatgcct agtgtctatt ttattaaaca aacaaacaca gagtttgaac    2640
tataatacta aggcctgaag tctagcttgg atatatgcta caataatatc tgttactcac    2700
ataaaattat atatttcaca gactttatca atgtataatt aacaattatc ttgtttaagt    2760
aaatttagaa tacattttaag tattgtggaa gaaataaaga cattccaata tttgcaaaaa    2820
aaaaaaaaa                                                            2830
```

<210> SEQ ID NO 2
<211> LENGTH: 691
<212> TYPE: PRT
<213> ORGANISM: Homo sapiens

<400> SEQUENCE: 2

```
Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asp Ser Ser Glu Asn Ser Thr Ser Thr Leu Ser Thr Cys Leu Ile
```

-continued

```
            130                 135                 140
Asn Gln Ile Leu Ser Leu Asn Arg Ala Ser Pro Glu Ile Val Gly Lys
145                 150                 155                 160
Gly Cys Leu Lys Glu Ser Gly Ser Tyr Met Trp Ile Tyr Val Phe Met
                165                 170                 175
Gly Asn Met Leu Arg Gly Ile Gly Glu Thr Pro Ile Val Pro Leu Gly
            180                 185                 190
Leu Ser Tyr Ile Asp Asp Phe Ala Lys Glu Gly His Ser Ser Leu Tyr
                195                 200                 205
Leu Gly Ile Leu Asn Ala Ile Ala Met Ile Gly Pro Ile Ile Gly Phe
            210                 215                 220
Thr Leu Gly Ser Leu Phe Ser Lys Met Tyr Val Asp Ile Gly Tyr Val
225                 230                 235                 240
Asp Leu Ser Thr Ile Arg Ile Thr Pro Thr Asp Ser Arg Trp Val Gly
                245                 250                 255
Ala Trp Trp Leu Asn Phe Leu Val Ser Gly Leu Phe Ser Ile Ile Ser
            260                 265                 270
Ser Ile Pro Phe Phe Leu Pro Gln Thr Pro Asn Lys Pro Gln Lys
            275                 280                 285
Glu Arg Lys Ala Ser Leu Ser Leu His Val Leu Glu Thr Asn Asp Glu
290                 295                 300
Lys Asp Gln Thr Ala Asn Leu Thr Asn Gln Gly Lys Asn Ile Thr Lys
305                 310                 315                 320
Asn Val Thr Gly Phe Phe Gln Ser Phe Lys Ser Ile Leu Thr Asn Pro
                325                 330                 335
Leu Tyr Val Met Phe Val Leu Leu Thr Leu Leu Gln Val Ser Ser Tyr
            340                 345                 350
Ile Gly Ala Phe Thr Tyr Val Phe Lys Tyr Val Glu Gln Gln Tyr Gly
            355                 360                 365
Gln Pro Ser Ser Lys Ala Asn Ile Leu Leu Gly Val Ile Thr Ile Pro
370                 375                 380
Ile Phe Ala Ser Gly Met Phe Leu Gly Gly Tyr Ile Ile Lys Lys Phe
385                 390                 395                 400
Lys Leu Asn Thr Val Gly Ile Ala Lys Phe Ser Cys Phe Thr Ala Val
                405                 410                 415
Met Ser Leu Ser Phe Tyr Leu Leu Tyr Phe Phe Ile Leu Cys Glu Asn
                420                 425                 430
Lys Ser Val Ala Gly Leu Thr Met Thr Tyr Asp Gly Asn Asn Pro Val
            435                 440                 445
Thr Ser His Arg Asp Val Pro Leu Ser Tyr Cys Asn Ser Asp Cys Asn
            450                 455                 460
Cys Asp Glu Ser Gln Trp Glu Pro Val Cys Gly Asn Asn Gly Ile Thr
465                 470                 475                 480
Tyr Ile Ser Pro Cys Leu Ala Gly Cys Lys Ser Ser Gly Asn Lys
                485                 490                 495
Lys Pro Ile Val Phe Tyr Asn Cys Ser Cys Leu Glu Val Thr Gly Leu
            500                 505                 510
Gln Asn Arg Asn Tyr Ser Ala His Leu Gly Glu Cys Pro Arg Asp Asp
            515                 520                 525
Ala Cys Thr Arg Lys Phe Tyr Phe Val Ala Ile Gln Val Leu Asn
            530                 535                 540
Leu Phe Phe Ser Ala Leu Gly Gly Thr Ser His Val Met Leu Ile Val
545                 550                 555                 560
```

```
Lys Ile Val Gln Pro Glu Leu Lys Ser Leu Ala Leu Gly Phe His Ser
                565                 570                 575
Met Val Ile Arg Ala Leu Gly Gly Ile Leu Ala Pro Ile Tyr Phe Gly
            580                 585                 590
Ala Leu Ile Asp Thr Thr Cys Ile Lys Trp Ser Thr Asn Asn Cys Gly
        595                 600                 605
Thr Arg Gly Ser Cys Arg Thr Tyr Asn Ser Thr Ser Phe Ser Arg Val
    610                 615                 620
Tyr Leu Gly Leu Ser Ser Met Leu Arg Val Ser Ser Leu Val Leu Tyr
625                 630                 635                 640
Ile Ile Leu Ile Tyr Ala Met Lys Lys Tyr Gln Glu Lys Asp Ile
                645                 650                 655
Asn Ala Ser Glu Asn Gly Ser Val Met Asp Glu Ala Asn Leu Glu Ser
            660                 665                 670
Leu Asn Lys Asn Lys His Phe Val Pro Ser Ala Gly Ala Asp Ser Glu
        675                 680                 685
Thr His Cys
    690

<210> SEQ ID NO 3
<211> LENGTH: 2442
<212> TYPE: DNA
<213> ORGANISM: Homo sapiens

<400> SEQUENCE: 3
cccgggtcga cccacgcgtc cgggataaag tactcccagg aaggctttga gccttggcag    60
aagaggctgg gattgaagct tcagggagag ccagaggtga ggctggagtg ggagatcacc   120
tgaggcaggg ccagcgggtg aggtacccca ggtaccagac aaggaaacca agccacaat    180
gggcacagaa aacacacctg gaggcaaagc cagcccagac cctcaggacg tgcggccaag   240
tgtgttccat aacatcaagc tgttcgttct gtgccacagc ctgctgcagc tggcgcagct   300
catgatctcc ggctacctaa agagctccat ctccacagtg gagaagcgct tcggcctctc   360
cagccagacg tcggggctgc tggcctcctt caacgaggtg gggaacacag ccttgattgt   420
gtttgtgagc tattttggca gccgggtgca ccgaccccga atgattggct atgggctat   480
ccttgtggcc ctggcgggcc tgctcatgac tctcccgcac ttcatctcgg agccataccg   540
ctacgacaac accagccctg aggatatgcc acaggacttc aaggcttccc tgtgcctgcc   600
cacaacctcg gccccagcct cggccccctc aatggcaac tgctcaagct acacagaaac   660
ccagcatctg agtgtggtgg ggatcatgtt cgtggcacag accctgctgg gcgtgggcgg   720
ggtgcccatt cagcccttg gcatctccta catcgttgac tttgcccaca cagtaactc   780
gcccctctac ctcgggatcc tgtttgcagt gaccatgatg gggccaggcc tggccttgg   840
gctgggcagc ctcatgctgc gcctttatgt ggacattaac cagatgccag aaggtggtat   900
cagcctgacc ataaaggacc ccgatgggg gggtgcctgg tggctgggtt tcctcatcgc   960
tgccggtgca gtggccctgg ctgccatccc ctacttcttc ttcccaaggg aaatgcccaa  1020
ggaaaaacgt gagcttcagt ttcggcgaaa ggtcttagca gtcacagact cacctgccag  1080
gaagggcaag gactctcccct ctaagcagag ccctgggggag tccacgaaga agcaggatgg  1140
cctagtccag attgcaccaa acctgactgt gatccagttc attaaagtct tcccagggt  1200
gctgctgcag accctacgcc accccatctt cctgctggtg gtcctgtccc aggtatgctt  1260
gtcatccatg gctgcgggca tggccacctt cctgcccaag ttcctggagc gccagttttc  1320
```

-continued

```
catcacagcc tcctacgcca acctgctcat cggctgcctc tccttcccett cggtcatcgt   1380 gggcatcgtg gtgggtggcg tcctggtcaa gcggctccac ctgggccctg tgggatgcgg   1440 tgcccttttgc ctgctgggga tgctgctgtg cctcttcttc agcctgccgc tcttctttat   1500
cggctgctcc agccaccaga ttgcgggcat cacacaccag accagtgccc accctgggct   1560
ggagctgtct ccaagctgca tggaggcctg ctcctgccca ttggacggct ttaaccctgt   1620
ctgcgacccc agcactcgtg tggaatacat cacaccctgc cacgcaggct gctcaagctg   1680
ggtggtccag gatgctctgg acaacagcca ggttttctac accaactgca gctgcgtggt   1740
ggagggcaac cccgtgctgg caggatcctg cgactcaacg tgcagccatc tggtggtgcc   1800
cttcctgctc ctggtcagcc tgggctcggc cctggcctgt ctcacccaca caccctcctt   1860
catgctcatc ctaagaggag tgaagaaaga agacaagact ttggctgtgg catccagtt   1920 catgttcctg aggattttgg cctggatgcc agcccccgtg atccacggca gcgccatcga   1980
caccacctgt gtgcactggg ccctgagctg tgggcgtcga gctgtctgtc gctactacaa   2040
taatgacctg ctccgaaacc ggttcatcgg cctccagttc ttcttcaaaa caggttctgt   2100
gatctgcttc gccttagttt tggctgtcct gaggcagcag acaaagagg caaggaccaa   2160 agagagcaga tccagccctg ccgtagagca gcaattgcta gtgtcgggggc cagggaagaa   2220 gccagaggat tcccgagtgt gagctgtctt ggggccccac ctggccaaga gtagcagcca   2280
cagcagtacc tcctctgagt ccttttgccca agattgggtg tcaagagccc tgtgttccat   2340
tctggctcct ccactaaatt gctgtgtgac ttcaggcaaa aaaaaaaaaa aaaaaaaaa   2400 aaaaaaaaaa aaaaaaaaaa aaaaaaaaaa aaaaaaaaaa aa                      2442
```

<210> SEQ ID NO 4
<211> LENGTH: 687
<212> TYPE: PRT
<213> ORGANISM: Homo sapiens

<400> SEQUENCE: 4

```
Met Gly Thr Glu Asn Thr Pro Gly Gly Lys Ala Ser Pro Asp Pro Gln
 1               5                  10                  15

Asp Val Arg Pro Ser Val Phe His Asn Ile Lys Leu Phe Val Leu Cys
            20                  25                  30

His Ser Leu Leu Gln Leu Ala Gln Leu Met Ile Ser Gly Tyr Leu Lys
        35                  40                  45

Ser Ser Ile Ser Thr Val Glu Lys Arg Phe Gly Leu Ser Ser Gln Thr
    50                  55                  60

Ser Gly Leu Leu Ala Ser Phe Asn Glu Val Gly Asn Thr Ala Leu Ile
65                  70                  75                  80

Val Phe Val Ser Tyr Phe Gly Ser Arg Val His Arg Pro Arg Met Ile
                85                  90                  95

Gly Tyr Gly Ala Ile Leu Val Ala Leu Ala Gly Leu Leu Met Thr Leu
            100                 105                 110

Pro His Phe Ile Ser Glu Pro Tyr Arg Tyr Asp Asn Thr Ser Pro Glu
        115                 120                 125

Asp Met Pro Gln Asp Phe Lys Ala Ser Leu Cys Leu Pro Thr Thr Ser
    130                 135                 140

Ala Pro Ala Ser Ala Pro Ser Asn Gly Asn Cys Ser Ser Tyr Thr Glu
145                 150                 155                 160

Thr Gln His Leu Ser Val Val Gly Ile Met Phe Val Ala Gln Thr Leu
                165                 170                 175
```

```
Leu Gly Val Gly Gly Val Pro Ile Gln Pro Phe Gly Ile Ser Tyr Ile
            180                 185                 190
Val Asp Phe Ala His Asn Ser Asn Ser Pro Leu Tyr Leu Gly Ile Leu
            195                 200                 205
Phe Ala Val Thr Met Met Gly Pro Gly Leu Ala Phe Gly Leu Gly Ser
            210                 215                 220
Leu Met Leu Arg Leu Tyr Val Asp Ile Asn Gln Met Pro Glu Gly Gly
225                 230                 235                 240
Ile Ser Leu Thr Ile Lys Asp Pro Arg Trp Val Gly Ala Trp Trp Leu
            245                 250                 255
Gly Phe Leu Ile Ala Ala Gly Ala Val Ala Leu Ala Ala Ile Pro Tyr
            260                 265                 270
Phe Phe Phe Pro Lys Glu Met Pro Lys Glu Lys Arg Glu Leu Gln Phe
            275                 280                 285
Arg Arg Lys Val Leu Ala Val Thr Asp Ser Pro Ala Arg Lys Gly Lys
            290                 295                 300
Asp Ser Pro Ser Lys Gln Ser Pro Gly Glu Ser Thr Lys Lys Gln Asp
305                 310                 315                 320
Gly Leu Val Gln Ile Ala Pro Asn Leu Thr Val Ile Gln Phe Ile Lys
            325                 330                 335
Val Phe Pro Arg Val Leu Leu Gln Thr Leu Arg His Pro Ile Phe Leu
            340                 345                 350
Leu Val Val Leu Ser Gln Val Cys Leu Ser Ser Met Ala Ala Gly Met
            355                 360                 365
Ala Thr Phe Leu Pro Lys Phe Leu Glu Arg Gln Phe Ser Ile Thr Ala
            370                 375                 380
Ser Tyr Ala Asn Leu Leu Ile Gly Cys Leu Ser Phe Pro Ser Val Ile
385                 390                 395                 400
Val Gly Ile Val Val Gly Gly Val Leu Val Lys Arg Leu His Leu Gly
            405                 410                 415
Pro Val Gly Cys Gly Ala Leu Cys Leu Leu Gly Met Leu Leu Cys Leu
            420                 425                 430
Phe Phe Ser Leu Pro Leu Phe Phe Ile Gly Cys Ser Ser His Gln Ile
            435                 440                 445
Ala Gly Ile Thr His Gln Thr Ser Ala His Pro Gly Leu Glu Leu Ser
            450                 455                 460
Pro Ser Cys Met Glu Ala Cys Ser Cys Pro Leu Asp Gly Phe Asn Pro
465                 470                 475                 480
Val Cys Asp Pro Ser Thr Arg Val Glu Tyr Ile Thr Pro Cys His Ala
            485                 490                 495
Gly Cys Ser Ser Trp Val Val Gln Asp Ala Leu Asp Asn Ser Gln Val
            500                 505                 510
Phe Tyr Thr Asn Cys Ser Cys Val Glu Gly Asn Pro Val Leu Ala
            515                 520                 525
Gly Ser Cys Asp Ser Thr Cys Ser His Leu Val Pro Phe Leu Leu
            530                 535                 540
Leu Val Ser Leu Gly Ser Ala Leu Ala Cys Leu Thr His Thr Pro Ser
545                 550                 555                 560
Phe Met Leu Ile Leu Arg Gly Val Lys Lys Glu Asp Lys Thr Leu Ala
            565                 570                 575
Val Gly Ile Gln Phe Met Phe Leu Arg Ile Leu Ala Trp Met Pro Ser
            580                 585                 590
```

Pro Val Ile His Gly Ser Ala Ile Asp Thr Thr Cys Val His Trp Ala
                595                 600                 605

Leu Ser Cys Gly Arg Arg Ala Val Cys Arg Tyr Tyr Asn Asn Asp Leu
    610                 615                 620

Leu Arg Asn Arg Phe Ile Gly Leu Gln Phe Phe Lys Thr Gly Ser
625                 630                 635                 640

Val Ile Cys Phe Ala Leu Val Leu Ala Val Leu Arg Gln Gln Asp Lys
                645                 650                 655

Glu Ala Arg Thr Lys Glu Ser Arg Ser Ser Pro Ala Val Glu Gln Gln
                660                 665                 670

Leu Leu Val Ser Gly Pro Gly Lys Lys Pro Glu Asp Ser Arg Val
                675                 680                 685

<210> SEQ ID NO 5
<211> LENGTH: 2757
<212> TYPE: DNA
<213> ORGANISM: Homo sapiens

<400> SEQUENCE: 5

| | | | | | |
|---|---|---|---|---|---|
| cccacgcgtc | cggcgaggag | ctgtgccttc | cacctctcca | gccccggcag | gacgggggcg | 60 |
| gccgccgcga | acccggggcg | gggacagcac | gcagcctcga | ggcgcgcacc | cccgcccggc | 120 |
| agcggccccg | acacccgggg | cgagcgggaa | agcggcagcg | gcggcggcgg | cggcggcggc | 180 |
| ggggaagga | tgcaggggaa | gaagccgggc | ggttcgtcgg | gcggcggccg | gagcggcgag | 240 |
| ctgcaggggg | acgaggcgca | gaggaacaag | aaaaagaaaa | agaaggtgtc | ctgcttttcc | 300 |
| aacatcaaga | tcttcctggt | gtccgagtgc | gccctgatgc | tggcgcaggg | cacggtgggc | 360 |
| gcctacctgg | tgagcgtcct | gaccaccctg | gagcgtaggt | caacctgca | gagcgctgac | 420 |
| gtgggtgtga | tcgctagcag | cttcgagatc | gggaacctgg | cgctcatcct | cttcgtgagc | 480 |
| tacttcgggg | cacgcgggca | ccggccgcgc | ctgatcggct | gcgcggcat | cgtcatggcg | 540 |
| ctgggcgcgc | tgctgtcggc | gctgcccgag | ttcctgaccc | accagtacaa | gtacgaggcg | 600 |
| ggcgagatcc | gctggggcgc | cgaggccgcc | gacgtctgcg | cagccaacgg | ctcgggcggc | 660 |
| gacgaggggc | ccgaccccga | cctcatctgc | cgcaaccgga | cggctaccaa | catgatgtac | 720 |
| ttgctgctca | ttggggccca | ggtgctcctg | ggcatcggtg | ctaccctgt | gcagcccctg | 780 |
| ggcgtctcct | acatcgacga | ccacgtgcgg | aggaaggact | cctcgctcta | tataggaatc | 840 |
| ctgttcacga | tgctggtatt | tggaccagcc | tgcgggttta | tcctgggctc | tttctgtacc | 900 |
| aaaatctacg | tggatgcggt | cttcattgac | acaagtaacc | tggacatcac | tccggacgac | 960 |
| ccccgctgga | tcgagcctg | gtggggtggc | tttctgctct | gcggtgcctt | actcttcttc | 1020 |
| tcttccctct | tgatgtttgg | gtttccacag | tccctgcccc | cgcactcaga | ccccgccatg | 1080 |
| gaaagcgagc | aggccatgct | ctccgaaaga | gaatacgaga | gacccaagcc | cagcaacggg | 1140 |
| gtcctgaggc | acccctgga | gccagacagc | agtgcctcct | gtttccagca | gctgagagtg | 1200 |
| atcccgaagg | tcaccaagca | cctgctctca | aaccctgtgt | tcacctgcat | catcctggcc | 1260 |
| gcctgcatgg | agattgcagt | ggtggctggc | ttcgctgcct | ttttggggaa | gtacctggag | 1320 |
| cagcagttta | acctcaccac | ctcttctgcc | aaccagctgc | ttgggatgac | tgcgatcccg | 1380 |
| tgtgcttgtc | tgggtatctt | cctgggaggt | cttttggtga | agaagctcag | cctgtctgcc | 1440 |
| ctggggccca | ttcggatggc | catgctcgtc | aacctggtgt | ccactgcttg | ctacgtctcc | 1500 |
| ttcctcttcc | tgggctgcga | cactggccct | gtggctgggg | ttactgttcc | ctatggaaac | 1560 |
| agcacagcac | ctggctcagc | cctggacccc | tactcgccct | gcaataataa | ctgtgaatgc | 1620 |

-continued

```
caaaccgatt ccttcactcc agtgtgtggg gcagatggca tcacctacct gtctgcctgc    1680
tttgctggct gcaacagcac gaatctcacg ggctgtgcgt gcctcaccac cgtccctgct    1740
gagaacgcaa ccgtggttcc tggaaaatgc cccagtcctg ggtgccaaga ggccttcctc    1800
actttcctct gtgtgatgtg tatctgcagc ctgatcggtg ccatggcaca gacaccctca    1860
gtcatcatcc tcatcaggac agtcagccct gaactcaagt cttacgcttt gggagttctt    1920
tttctcctcc ttcgtttgtt gggcttcatc cctccacccc tcatcttcgg ggctggcatc    1980
gactccacct gcctgttctg gagcacgttc tgtggggagc aaggcgcctg cgtcctctac    2040
gacaatgtgg tctaccgata cctgtatgtc agcatcgcca tcgcgctcaa atccttcgcc    2100
ttcatcctgt acaccaccac gtggcagtgc ctgaggaaaa actataaacg ctacatcaaa    2160
aaccacgagg gcgggctgag caccagtgag ttctttgcct ctactctgac cctagacaac    2220
ctggggaggg accctgtgcc cgcaaaccag acacatagga caaagtttat ctataacctg    2280
gaagaccatg agtggtgtga aaacatggag tccgttttat agtgactaaa ggagggctga    2340
actctgtatt agtaatccaa gggtcatttt tttcttaaaa aagaaaaaa aggttccaaa    2400 aaaaaccaaa actcagtaca cacacacagg cacagatgca cacacgcca gacagacaca    2460 ccgactttgt cctttttctc agcatcagag ccagacagga ttcagaataa ggagagaatg    2520
acatcgtgcg gcagggtcct ggaggccact cgcgcggctg ggccacagag tctactttga    2580
aggcacctca tggttttcag gatgctgaca gctgcaagca acaggcactg ccaaattcag    2640
ggaacagtgg tggccagctt ggaggatgga catttctgga tacacataca catacaaaac    2700
agaaaacatt ttttaaaaga agtttcctaa aataaaaaaa ataaaaaaaa aaaaaaa     2757
```

<210> SEQ ID NO 6
<211> LENGTH: 710
<212> TYPE: PRT
<213> ORGANISM: Homo sapiens

<400> SEQUENCE: 6

```
Met Gln Gly Lys Lys Pro Gly Gly Ser Ser Gly Gly Arg Ser Gly
1               5                   10                  15

Glu Leu Gln Gly Asp Glu Ala Gln Arg Asn Lys Lys Lys Lys
            20                  25                  30

Val Ser Cys Phe Ser Asn Ile Lys Ile Phe Leu Val Ser Glu Cys Ala
        35                  40                  45

Leu Met Leu Ala Gln Gly Thr Val Gly Ala Tyr Leu Val Ser Val Leu
    50                  55                  60

Thr Thr Leu Glu Arg Arg Phe Asn Leu Gln Ser Ala Asp Val Gly Val
65                  70                  75                  80

Ile Ala Ser Ser Phe Glu Ile Gly Asn Leu Ala Leu Ile Leu Phe Val
                85                  90                  95

Ser Tyr Phe Gly Ala Arg Gly His Arg Pro Arg Leu Ile Gly Cys Gly
            100                 105                 110

Gly Ile Val Met Ala Leu Gly Ala Leu Leu Ser Ala Leu Pro Glu Phe
        115                 120                 125

Leu Thr His Gln Tyr Lys Tyr Glu Ala Gly Glu Ile Arg Trp Gly Ala
    130                 135                 140

Glu Gly Arg Asp Val Cys Ala Ala Asn Gly Ser Gly Gly Asp Glu Gly
145                 150                 155                 160

Pro Asp Pro Asp Leu Ile Cys Arg Asn Arg Thr Ala Thr Asn Met Met
                165                 170                 175
```

```
Tyr Leu Leu Ile Gly Ala Gln Val Leu Leu Gly Ile Gly Ala Thr
            180                 185                 190

Pro Val Gln Pro Leu Gly Val Ser Tyr Ile Asp Asp His Val Arg Arg
            195                 200                 205

Lys Asp Ser Ser Leu Tyr Ile Gly Ile Leu Phe Thr Met Leu Val Phe
            210                 215                 220

Gly Pro Ala Cys Gly Phe Ile Leu Gly Ser Phe Cys Thr Lys Ile Tyr
225                 230                 235                 240

Val Asp Ala Val Phe Ile Asp Thr Ser Asn Leu Asp Ile Thr Pro Asp
            245                 250                 255

Asp Pro Arg Trp Ile Gly Ala Trp Trp Gly Phe Leu Leu Cys Gly
            260                 265                 270

Ala Leu Leu Phe Phe Ser Ser Leu Leu Met Phe Gly Phe Pro Gln Ser
            275                 280                 285

Leu Pro Pro His Ser Asp Pro Ala Met Glu Ser Glu Gln Ala Met Leu
            290                 295                 300

Ser Glu Arg Glu Tyr Glu Arg Pro Lys Pro Ser Asn Gly Val Leu Arg
305                 310                 315                 320

His Pro Leu Glu Pro Asp Ser Ser Ala Ser Cys Phe Gln Gln Leu Arg
            325                 330                 335

Val Ile Pro Lys Val Thr Lys His Leu Leu Ser Asn Pro Val Phe Thr
            340                 345                 350

Cys Ile Ile Leu Ala Ala Cys Met Glu Ile Ala Val Val Ala Gly Phe
            355                 360                 365

Ala Ala Phe Leu Gly Lys Tyr Leu Glu Gln Gln Phe Asn Leu Thr Thr
            370                 375                 380

Ser Ser Ala Asn Gln Leu Leu Gly Met Thr Ala Ile Pro Cys Ala Cys
385                 390                 395                 400

Leu Gly Ile Phe Leu Gly Gly Leu Leu Val Lys Lys Leu Ser Leu Ser
            405                 410                 415

Ala Leu Gly Ala Ile Arg Met Ala Met Leu Val Asn Leu Val Ser Thr
            420                 425                 430

Ala Cys Tyr Val Ser Phe Leu Phe Leu Gly Cys Asp Thr Gly Pro Val
            435                 440                 445

Ala Gly Val Thr Val Pro Tyr Gly Asn Ser Thr Ala Pro Gly Ser Ala
            450                 455                 460

Leu Asp Pro Tyr Ser Pro Cys Asn Asn Asn Cys Glu Cys Gln Thr Asp
465                 470                 475                 480

Ser Phe Thr Pro Val Cys Gly Ala Asp Gly Ile Thr Tyr Leu Ser Ala
            485                 490                 495

Cys Phe Ala Gly Cys Asn Ser Thr Asn Leu Thr Gly Cys Ala Cys Leu
            500                 505                 510

Thr Thr Val Pro Ala Glu Asn Ala Thr Val Val Pro Gly Lys Cys Pro
            515                 520                 525

Ser Pro Gly Cys Gln Glu Ala Phe Leu Thr Phe Leu Cys Val Met Cys
            530                 535                 540

Ile Cys Ser Leu Ile Gly Ala Met Ala Gln Thr Pro Ser Val Ile Ile
545                 550                 555                 560

Leu Ile Arg Thr Val Ser Pro Glu Leu Lys Ser Tyr Ala Leu Gly Val
            565                 570                 575

Leu Phe Leu Leu Leu Arg Leu Leu Gly Phe Ile Pro Pro Leu Ile
            580                 585                 590
```

```
Phe Gly Ala Gly Ile Asp Ser Thr Cys Leu Phe Trp Ser Thr Phe Cys
            595                 600                 605
Gly Glu Gln Gly Ala Cys Val Leu Tyr Asp Asn Val Tyr Arg Tyr
        610                 615                 620
Leu Tyr Val Ser Ile Ala Ile Ala Leu Lys Ser Phe Ala Phe Ile Leu
625                 630                 635                 640
Tyr Thr Thr Thr Trp Gln Cys Leu Arg Lys Asn Tyr Lys Arg Tyr Ile
                645                 650                 655
Lys Asn His Glu Gly Gly Leu Ser Thr Ser Glu Phe Phe Ala Ser Thr
            660                 665                 670
Leu Thr Leu Asp Asn Leu Gly Arg Asp Pro Val Pro Ala Asn Gln Thr
            675                 680                 685
His Arg Thr Lys Phe Ile Tyr Asn Leu Glu Asp His Glu Trp Cys Glu
            690                 695                 700
Asn Met Glu Ser Val Leu
705                 710

<210> SEQ ID NO 7
<211> LENGTH: 3692
<212> TYPE: DNA
<213> ORGANISM: Homo sapiens
<220> FEATURE:
<221> NAME/KEY: misc_feature
<222> LOCATION: (713)..(713)
<223> OTHER INFORMATION: y = c or t
<220> FEATURE:
<221> NAME/KEY: misc_feature
<222> LOCATION: (2397)..(2397)
<223> OTHER INFORMATION: k = g or t

<400> SEQUENCE: 7
ctgatttctc ttcggctgga cggaggctgc ctcctcacgc ggctcccaac tattcccgta      60
gctcagtgcc ccctcccgc cgctctactc agccaggcag acagactgac agactcgcta     120
gtcggcagct tcactcccga gggtgccgcg agcccaggcg gcgaacaccc ggtacccctg     180
gcgcagcgag gtgggatgct gtacggacag cagcgctaag tgcccccca ccccggcgc      240
agggtgcact cgctcctggc gcgggccca gcggcggcgg cggcggcggc ggcggagggg     300
atgagcccgg gacgcgcgag gcgcctgcct caagctaccg cccggagagg gacgccgagt     360
agggctcatc gcagtaccgc gcggacccct gccccctgtg gcacgcggct gcggagcctt     420
gaagccgtgt ctgtgatcag gatgcactgg gcgcctcgca gctggtgagg atgccctgct     480
gcgcggccct gcgcccccag ccccagtccc aggtgggcaa gactgactgg gcccggcttc     540
ggcccctcgt gccggtggat gaaacgtgcc ggagtgcttg ggtgccatca gctatcaaat     600
ctgaattcta agcgccatgg acgaaggcac tggactgcag cccggggcgg gagagcagct     660
ggaggcgccg gccactgcag aagctgtcca agagaggtgc gagccggaga ccytcaggtc     720
taagagttta ccggtcctca gcagcgcctc ctgccggcca agcctcagtc ccactagtgg     780
agacgccaac ccgccctttg gctgtgtgga ttcttcgggc caccaggagt tgaagcaagg     840
cccgaacccg ttggccccca gtccctctgc ccgtccact tcggcggggc tcggggactg     900
taaccacagg gtggacctca gcaaaacctt tcggtgtcc tccgccttgg ccatgctcca     960
ggagagaagg tgcctctacg tggtcctcac ggattcccgt tgcttcctgg tgtgcatgtg    1020
ctttctgacc ttcatccagg cgttaatggt ctctgggtac ctgagcagcg taattaccac    1080
cattgaaagg cgctacagtc tgaagagttc cgagtcgggg ctgctggtca gctgctttga    1140
catcgggaac ctggtggtgg tggtgttcgt cagctacttc ggcggccggg gtcggcggcc    1200
```

```
cctgtggctg gccgtgggtg gactcctcat cgccttcggg gcagccctct tcgccttacc   1260
tcacttcatc tcgcccccct accagatcca agagttgaac gcctcggccc ccaacgacgg   1320
cctgtgtcag ggtggcaact ccaccgccac tttggagcct ccggcctgtc cgaaggactc   1380 ggaggaaat aatcactggg tctacctggc tttattcatt tgcgcgcaga ttctcattgg    1440
aatgggctcc acacctattt ataccctggg accaacctac ttagatgaca atgtcaagaa   1500
agaaaactcc tccttgtacc tagccatcat gtatgtcatg ggagcacttg gccctgcagt   1560
gggatattta ttaggtggac ttcttattgg tttttatgtt gatcccagaa atcctgttca   1620
ccttgaccag aatgaccctc gtttcattgg aaactggtgg agtggattcc tcctttgtgc   1680
cattgcaatg tttcttgtga tattcccaat gtttactttc ccaaaaaagc ttccacctcg   1740
acacaagaaa aagaaaaaga aaaattttc tgttgatgct gttagtgatg acgatgttct    1800
gaaggagaaa tcaaacaaca gtgaacaagc ggacaaaaaa gtttcttcga tgggatttgg   1860
aaaggatgtc agagacctac caagagcagc tgtcaggatc ttaagcaaca tgacattcct   1920
ttttgtgagt ttgtcataca cagctgagag tgccattgta actgctttca ttaccttcat   1980
tcccaagttc atcgagtcac agtttggtat cccagcctcc aatgccagca tctacactgg   2040
ggttattatc gtccccagtg ctggtgttgg tattgtcctc ggaggctaca ttataaaaaa   2100
attgaaactt ggtgccagag aatctgcaaa actagcaatg atctgcagtg gtgtgtcttt   2160 actatgttt tcaaccctat ttattgttgg atgtgaaagc attaatctag ggggcataaa    2220
catcccttat acaacaggac cttctctcac catgccccat aggaatctga caggaagctg   2280
caacgttaat tgtggtttgta aaatacacga gtatgagcca gtctgtggat cagatggaat  2340
tacatacttt aaccccttgtc tggctggctg tgttaatagt ggtaatctta gcactgkgat   2400
acggaattat acagaatgca cctgtgtcca aagtcgccaa gtgatcactc cacccaccgt    2460
gggacagcga agtcagctcc gtgtggttat tgtcaagact tatctcaatg agaacggcta    2520
tgctgtgtct gggaaatgta aacggacctg caatactctt atcccattct tagttttttct   2580 tttcatagtc accttcatca cagcatgtgc ccaaccatca gctatcatag taacactcag    2640
gtccgtagaa gatgaggaga gaccttttgc actgggaatg cagtttgttt tgttgcgaac    2700
acttgcatac attcctactc caatctactt tggagcagtc attgacacca cctgcatgct    2760
ctggcaacag gaatgtggtg tgcagggttc ttgctgggag tacaacgtga cgtcgttttcg   2820 ttttgtgtat tttggtttgg ctgccggcct caaattcgtt gggtttattt ttatttttct    2880
ggcctggtac tccataaaat acaaggagga tggactgcag aggcggaggc agagagaatt    2940 tccctgagc accgtgagtg agagagtggg acaccccgac aatgcccgga ctagatcttg     3000
cccagctttc agcacccagg gagaattcca cgaagagact ggcctgcaaa aagggatcca    3060
gtgcgcagca cagacctacc cggggcccct cccagaagca ataagttcct ctgcggaccc    3120
ggggctggaa gagagccccg ctgccttgga gccgccctcc tgaagcttga aaatggaaga    3180
atttagtttt gttggttgaa ttgaaaatgg cgacttgaga acaactgtg ccttctttc     3240 tttctttctt ttttttaacc tctacagaca caatcctcaa accaacaaaa ctcagtatac    3300
acagccgcta ttcattgagg gctggatacc tcaacaagac tgagagcctt tccccgcttc   3360
tctccaagaa ggagacgttc agctagattt gttcccattt ccgttgtgtt aattcaaagc    3420
tcatgctccc ctacggtaca ggctgaggta cacggttagc aaaaccatgg gaaggggaat    3480
ggcggtgcat atcattaact aacactccaa acaaaggtga gcttgcccag gacttggcat    3540
```

-continued

```
ttccaaatca aagtttttag atatgaacac ctactgtgag ttctgctaca aagcacaaat    3600
gaatttgtct caactatgca atttgattgg aaaaatgtat gtgcagcatg ttacatttac    3660
tttcacggaa taaagcagat atgtttctga aa                                  3692
```

```
<210> SEQ ID NO 8
<211> LENGTH: 848
<212> TYPE: PRT
<213> ORGANISM: Homo sapiens
<220> FEATURE:
<221> NAME/KEY: PEPTIDE
<222> LOCATION: (33)..(33)
<223> OTHER INFORMATION: Xaa = Leu or Phe
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: PEPTIDE
<222> LOCATION: (594)..(594)
<223> OTHER INFORMATION: Xaa = Gly or Val
<220> FEATURE:
<221> NAME/KEY: misc_feature
<222> LOCATION: (594)..(594)
<223> OTHER INFORMATION: Xaa can be any naturally occurring amino acid
```

<400> SEQUENCE: 8

```
Met Asp Glu Gly Thr Gly Leu Gln Pro Gly Ala Gly Glu Gln Leu Glu
 1               5                  10                  15

Ala Pro Ala Thr Ala Glu Ala Val Gln Glu Arg Cys Glu Pro Glu Thr
            20                  25                  30

Xaa Arg Ser Lys Ser Leu Pro Val Leu Ser Ser Ala Ser Cys Arg Pro
        35                  40                  45

Ser Leu Ser Pro Thr Ser Gly Asp Ala Asn Pro Ala Phe Gly Cys Val
    50                  55                  60

Asp Ser Ser Gly His Gln Glu Leu Lys Gln Gly Pro Asn Pro Leu Ala
65                  70                  75                  80

Pro Ser Pro Ser Ala Pro Ser Thr Ser Ala Gly Leu Gly Asp Cys Asn
                85                  90                  95

His Arg Val Asp Leu Ser Lys Thr Phe Ser Val Ser Ser Ala Leu Ala
            100                 105                 110

Met Leu Gln Glu Arg Arg Cys Leu Tyr Val Val Leu Thr Asp Ser Arg
        115                 120                 125

Cys Phe Leu Val Cys Met Cys Phe Leu Thr Phe Ile Gln Ala Leu Met
    130                 135                 140

Val Ser Gly Tyr Leu Ser Ser Val Ile Thr Thr Ile Glu Arg Arg Tyr
145                 150                 155                 160

Ser Leu Lys Ser Ser Glu Ser Gly Leu Leu Val Ser Cys Phe Asp Ile
                165                 170                 175

Gly Asn Leu Val Val Val Phe Val Ser Tyr Phe Gly Gly Arg Gly
            180                 185                 190

Arg Arg Pro Leu Trp Leu Ala Val Gly Gly Leu Leu Ile Ala Phe Gly
        195                 200                 205

Ala Ala Leu Phe Ala Leu Pro His Phe Ile Ser Pro Pro Tyr Gln Ile
    210                 215                 220

Gln Glu Leu Asn Ala Ser Ala Pro Asn Asp Gly Leu Cys Gln Gly Gly
225                 230                 235                 240

Asn Ser Thr Ala Thr Leu Glu Pro Pro Ala Cys Pro Lys Asp Ser Gly
                245                 250                 255

Gly Asn Asn His Trp Val Tyr Leu Ala Leu Phe Ile Cys Ala Gln Ile
```

-continued

```
                260                 265                 270
Leu Ile Gly Met Gly Ser Thr Pro Ile Tyr Thr Leu Gly Pro Thr Tyr
                275                 280                 285
Leu Asp Asp Asn Val Lys Lys Glu Asn Ser Ser Leu Tyr Leu Ala Ile
                290                 295                 300
Met Tyr Val Met Gly Ala Leu Gly Pro Ala Val Gly Tyr Leu Leu Gly
305                 310                 315                 320
Gly Leu Leu Ile Gly Phe Tyr Val Asp Pro Arg Asn Pro Val His Leu
                325                 330                 335
Asp Gln Asn Asp Pro Arg Phe Ile Gly Asn Trp Trp Ser Gly Phe Leu
                340                 345                 350
Leu Cys Ala Ile Ala Met Phe Leu Val Ile Phe Pro Met Phe Thr Phe
                355                 360                 365
Pro Lys Lys Leu Pro Pro Arg His Lys Lys Lys Lys Lys Lys Lys Phe
                370                 375                 380
Ser Val Asp Ala Val Ser Asp Asp Val Leu Lys Glu Lys Ser Asn
385                 390                 395                 400
Asn Ser Glu Gln Ala Asp Lys Lys Val Ser Ser Met Gly Phe Gly Lys
                405                 410                 415
Asp Val Arg Asp Leu Pro Arg Ala Ala Val Arg Ile Leu Ser Asn Met
                420                 425                 430
Thr Phe Leu Phe Val Ser Leu Ser Tyr Thr Ala Glu Ser Ala Ile Val
                435                 440                 445
Thr Ala Phe Ile Thr Phe Ile Pro Lys Phe Ile Glu Ser Gln Phe Gly
                450                 455                 460
Ile Pro Ala Ser Asn Ala Ser Ile Tyr Thr Gly Val Ile Ile Val Pro
465                 470                 475                 480
Ser Ala Gly Val Gly Ile Val Leu Gly Gly Tyr Ile Ile Lys Lys Leu
                485                 490                 495
Lys Leu Gly Ala Arg Glu Ser Ala Lys Leu Ala Met Ile Cys Ser Gly
                500                 505                 510
Val Ser Leu Leu Cys Phe Ser Thr Leu Phe Ile Val Gly Cys Glu Ser
                515                 520                 525
Ile Asn Leu Gly Gly Ile Asn Ile Pro Tyr Thr Thr Gly Pro Ser Leu
                530                 535                 540
Thr Met Pro His Arg Asn Leu Thr Gly Ser Cys Asn Val Asn Cys Gly
545                 550                 555                 560
Cys Lys Ile His Glu Tyr Glu Pro Val Cys Gly Ser Asp Gly Ile Thr
                565                 570                 575
Tyr Phe Asn Pro Cys Leu Ala Gly Cys Val Asn Ser Gly Asn Leu Ser
                580                 585                 590
Thr Xaa Ile Arg Asn Tyr Thr Glu Cys Thr Cys Val Gln Ser Arg Gln
                595                 600                 605
Val Ile Thr Pro Pro Thr Val Gly Gln Arg Ser Gln Leu Arg Val Val
                610                 615                 620
Ile Val Lys Thr Tyr Leu Asn Glu Asn Gly Tyr Ala Val Ser Gly Lys
625                 630                 635                 640
Cys Lys Arg Thr Cys Asn Thr Leu Ile Pro Phe Leu Val Phe Leu Phe
                645                 650                 655
Ile Val Thr Phe Ile Thr Ala Cys Ala Gln Pro Ser Ala Ile Ile Val
                660                 665                 670
Thr Leu Arg Ser Val Glu Asp Glu Glu Arg Pro Phe Ala Leu Gly Met
                675                 680                 685
```

-continued

```
Gln Phe Val Leu Leu Arg Thr Leu Ala Tyr Ile Pro Thr Pro Ile Tyr
    690                 695                 700
Phe Gly Ala Val Ile Asp Thr Thr Cys Met Leu Trp Gln Gln Glu Cys
705                 710                 715                 720
Gly Val Gln Gly Ser Cys Trp Glu Tyr Asn Val Thr Ser Phe Arg Phe
                725                 730                 735
Val Tyr Phe Gly Leu Ala Ala Gly Leu Lys Phe Val Gly Phe Ile Phe
            740                 745                 750
Ile Phe Leu Ala Trp Tyr Ser Ile Lys Tyr Lys Glu Asp Gly Leu Gln
        755                 760                 765
Arg Arg Arg Gln Arg Glu Phe Pro Leu Ser Thr Val Ser Glu Arg Val
770                 775                 780
Gly His Pro Asp Asn Ala Arg Thr Arg Ser Cys Pro Ala Phe Ser Thr
785                 790                 795                 800
Gln Gly Glu Phe His Glu Thr Gly Leu Gln Lys Gly Ile Gln Cys
                805                 810                 815
Ala Ala Gln Thr Tyr Pro Gly Pro Phe Pro Glu Ala Ile Ser Ser Ser
            820                 825                 830
Ala Asp Pro Gly Leu Glu Glu Ser Pro Ala Ala Leu Glu Pro Pro Ser
        835                 840                 845
```

<210> SEQ ID NO 9
<211> LENGTH: 3381
<212> TYPE: DNA
<213> ORGANISM: Homo sapiens

<400> SEQUENCE: 9

```
cgcaaagaaa tggctcaaaa gcttcagctc tttctgtgcc ctgggagctg agatgcacgt      60
cagtggcctt gccagcgtgg ccaattctct gctgactgcc agaaaaaaga ggccaggaag     120
aaagaggaaa gagaagagat cgctcagggg tgagaccatg cccttcatct tttcttttcc     180
ctaatctcct ctgcttgtgt ccacccacac tctccccacc tggcaaaatt gttcaaaatt     240
gctgtggagt ttacctcagt ttcctctttc agtctgtggt gtgtggtcca tcctcttgct     300
gagcacattg aaaggaactg gctatctttg atctcttcct ccagatcaga gtcaaggaat     360
gtgtttataa tggacacttc atccaaagaa aatatccagt tgttctgcaa aacttcagtg     420
caacctgttg gaaggccttc ttttaaaaca gaatatccct cctcagaaga aaagcaacca     480
tgctgtggtg aactaaaggt gttcttgtgt gccttgtctt ttgtttactt tgccaaagca     540
ttggcagaag gctatctgaa gagcaccatc actcagatag agagaaggtt tgatatccct     600
tcttcactgg tgggagttat tgatggtagt tttgaaattg ggaatctctt agttataaca     660
tttgttagct actttggagc caaacttcac aggccaaaaa taattggagc agggtgtgta     720
atcatgggag ttggaacact gctcattgca atgcctcagt tcttcatgga gcagtacaaa     780
tatgagagat attctccttc ctccaattcc actctcagca tctctccgtg tctcctagag     840
tcaagcagtc aattaccagt ttcagttatg gaaaaatcaa aatccaaaat aagtaacgaa     900
tgtgaagtgg acactagctc ttccatgtgg atttatgttt tcctgggcaa tcttcttcgt     960
ggaataggag aaactcccat tcagcctttg ggcattgcct acctggatga ttttgccagt    1020
gaagacaatg cagctttcta tattgggtgt gtgcagacgg ttgcaattat aggaccaatc    1080
tttggttttc tgttaggctc attatgtgcc aaactatatg ttgacattgg ctttgtaaac    1140
ctagatcaca taaccattac cccaaaagat ccccagtggg taggagcctg gtggcttggc    1200
```

-continued

```
tatctaatag caggaatcat aagtcttctt gcagctgtgc cttctggta tttaccaaag      1260 agtttaccaa gatcccaaag tagagaggat tctaattctt cctctgagaa atccaagttt    1320
attatagatg atcacacaga ctaccaaaca ccccagggag aaaatgcaaa ataatggaa     1380 atggcaagag atttcttcc atcactgaag aatcttttg gaaacccagt atacttccta      1440
tatttatgta caagcactgt tcagttcaat ctctgttcg catggtgac gtacaaacca      1500 aagtacattg agcagcagta tggacagtca tcctccaggg ccaactttgt gatcgggctc    1560
atcaacattc cagcagtggc ccttggaata ttctctgggg ggatagttat gaaaaaattc    1620
agaatcagtg tgtgtggagc tgcaaaactc tacttgggat catctgtctt tggttacctc    1680
ctatttcttt ccctgtttgc actgggctgt gaaaattctg atgtggcagg actaactgtc    1740
tcctaccaag gaaccaaacc tgtctcttat catgaacgag ctctcttttc agattgcaac    1800
tcaagatgca aatgttcaga gacaaaatgg gaacccatgt gcggtgaaaa tggaatcaca    1860
tatgtatcag cttgtcttgc tggttgtcaa acctccaaca ggagtggaaa aatatatta    1920 ttttacaact gcacttgtgt gggaattgca gcttctaaat ccggaaattc ctcaggcata    1980
gtgggaagat gtcagaaaga caatggatgt ccccaaatgt ttctgtattt ccttgtaatt    2040
tcagtcatca catcctatac tttatcccta ggtggcatac ctggatacat attacttctg    2100
aggtgcatta agccacagct taagtctttt gccttgggta tctacacatt agcaataaga    2160
gttcttgcag gaatcccagc tccagtgtat tttggagttt tgattgatac ttcatgcctc    2220
aaatggggat ttaaaagatg tggaagtaga ggatcatgca gattatatga ttcaaatgtc    2280
ttcagacata tatatttggg actaactgtg atactgggca cagtgtcaat tctcctaagc    2340
attgcagtac ttttcatttt aaagaaaaat tatgttcaa acacagaag tttttataacc    2400 aagagagaaa gaacaatggt gtctacaaga ttccaaaagg aaaattacac tacaagtgat    2460
catctgctac aacccaacta ctggccaggc aaggaaactc aactttagaa acatgatgac    2520
tggaagtcat gtcttctaat tggttgacat tttgcaaaca aataaattgt aatcaaaaga    2580
gctctaaatt tgtaatttct ttctccttc aaaaaatgtc tactttgttt tggtcctagg     2640
cattaggtaa tataactgat aatatactga aatatataat ggaagatgca gatgataaaa    2700
ctaattttga actttttaat ttatataaat tattttatat catttactta tttcactta     2760 ttttgctttg tgctcattga tatatattag ctgtactcct agaagaacaa ttgtctctat    2820
tgtcacacat ggttatattt aaagtaattt ctgaactgtg taatgtgtct agagtaagca    2880
aatactgcta acaattaact cataccttgg gttccttcaa gtattactcc tatagtattt    2940
tctcccatag ctgtcttcat ctgtgtattt taataatgat cttaggatgg agcagaacat    3000
ggagaggaag atttcattt aagctcctcc ttttccttga aatacaataa tttatataga    3060
aatgtgtagc agcaaattat attggggatt agaattttga attaatagct ctcctactat    3120
taatttacat gtgctttttg tgtggcgcta taagtgacta tggttgtaaa gtaataaaat    3180
tgatgttaac atgcccaatt attgttcttt tatgaattca atgaatttaa aactattgtt    3240
aaatataata ctgccccact ttaatatatg taagcaactt cctacttata cacgacgtgt    3300
tcctaaaaca tgtttgaaag gtgaatttct gaaagtctcc cataaatgta ggtgttacaa    3360
caggaaaaaa aaaaaaaaa a                                                3381
```

<210> SEQ ID NO 10
<211> LENGTH: 712
<212> TYPE: PRT
<213> ORGANISM: Homo sapiens

<400> SEQUENCE: 10

```
Met Asp Thr Ser Ser Lys Glu Asn Ile Gln Leu Phe Cys Lys Thr Ser
1               5                   10                  15

Val Gln Pro Val Gly Arg Pro Ser Phe Lys Thr Glu Tyr Pro Ser Ser
            20                  25                  30

Glu Glu Lys Gln Pro Cys Cys Gly Glu Leu Lys Val Phe Leu Cys Ala
        35                  40                  45

Leu Ser Phe Val Tyr Phe Ala Lys Ala Leu Ala Glu Gly Tyr Leu Lys
    50                  55                  60

Ser Thr Ile Thr Gln Ile Glu Arg Arg Phe Asp Ile Pro Ser Ser Leu
65                  70                  75                  80

Val Gly Val Ile Asp Gly Ser Phe Glu Ile Gly Asn Leu Leu Val Ile
                85                  90                  95

Thr Phe Val Ser Tyr Phe Gly Ala Lys Leu His Arg Pro Lys Ile Ile
                100                 105                 110

Gly Ala Gly Cys Val Ile Met Gly Val Gly Thr Leu Leu Ile Ala Met
            115                 120                 125

Pro Gln Phe Phe Met Glu Gln Tyr Lys Tyr Glu Arg Tyr Ser Pro Ser
    130                 135                 140

Ser Asn Ser Thr Leu Ser Ile Ser Pro Cys Leu Leu Glu Ser Ser Ser
145                 150                 155                 160

Gln Leu Pro Val Ser Val Met Glu Lys Ser Lys Ser Lys Ile Ser Asn
                165                 170                 175

Glu Cys Glu Val Asp Thr Ser Ser Met Trp Ile Tyr Val Phe Leu
                180                 185                 190

Gly Asn Leu Leu Arg Gly Ile Gly Glu Thr Pro Ile Gln Pro Leu Gly
            195                 200                 205

Ile Ala Tyr Leu Asp Asp Phe Ala Ser Glu Asp Asn Ala Ala Phe Tyr
    210                 215                 220

Ile Gly Cys Val Gln Thr Val Ala Ile Ile Gly Pro Ile Phe Gly Phe
225                 230                 235                 240

Leu Leu Gly Ser Leu Cys Ala Lys Leu Tyr Val Asp Ile Gly Phe Val
                245                 250                 255

Asn Leu Asp His Ile Thr Ile Thr Pro Lys Asp Pro Gln Trp Val Gly
                260                 265                 270

Ala Trp Trp Leu Gly Tyr Leu Ile Ala Gly Ile Ile Ser Leu Leu Ala
            275                 280                 285

Ala Val Pro Phe Trp Tyr Leu Pro Lys Ser Leu Pro Arg Ser Gln Ser
    290                 295                 300

Arg Glu Asp Ser Asn Ser Ser Glu Lys Ser Lys Phe Ile Ile Asp
305                 310                 315                 320

Asp His Thr Asp Tyr Gln Thr Pro Gln Gly Glu Asn Ala Lys Ile Met
                325                 330                 335

Glu Met Ala Arg Asp Phe Leu Pro Ser Leu Lys Asn Leu Phe Gly Asn
            340                 345                 350

Pro Val Tyr Phe Leu Tyr Leu Cys Thr Ser Thr Val Gln Phe Asn Ser
    355                 360                 365

Leu Phe Gly Met Val Thr Tyr Lys Pro Lys Tyr Ile Glu Gln Gln Tyr
    370                 375                 380

Gly Gln Ser Ser Ser Arg Ala Asn Phe Val Ile Gly Leu Ile Asn Ile
385                 390                 395                 400

Pro Ala Val Ala Leu Gly Ile Phe Ser Gly Gly Ile Val Met Lys Lys
```

405                 410                 415
Phe Arg Ile Ser Val Cys Gly Ala Ala Lys Leu Tyr Leu Gly Ser Ser
                420                 425                 430

Val Phe Gly Tyr Leu Leu Phe Leu Ser Leu Phe Ala Leu Gly Cys Glu
            435                 440                 445

Asn Ser Asp Val Ala Gly Leu Thr Val Ser Tyr Gln Gly Thr Lys Pro
        450                 455                 460

Val Ser Tyr His Glu Arg Ala Leu Phe Ser Asp Cys Asn Ser Arg Cys
465                 470                 475                 480

Lys Cys Ser Glu Thr Lys Trp Glu Pro Met Cys Gly Glu Asn Gly Ile
                485                 490                 495

Thr Tyr Val Ser Ala Cys Leu Ala Gly Cys Gln Thr Ser Asn Arg Ser
                500                 505                 510

Gly Lys Asn Ile Ile Phe Tyr Asn Cys Thr Cys Val Gly Ile Ala Ala
                515                 520                 525

Ser Lys Ser Gly Asn Ser Ser Gly Ile Val Gly Arg Cys Gln Lys Asp
        530                 535                 540

Asn Gly Cys Pro Gln Met Phe Leu Tyr Phe Leu Val Ile Ser Val Ile
545                 550                 555                 560

Thr Ser Tyr Thr Leu Ser Leu Gly Gly Ile Pro Gly Tyr Ile Leu Leu
                565                 570                 575

Leu Arg Cys Ile Lys Pro Gln Leu Lys Ser Phe Ala Leu Gly Ile Tyr
                580                 585                 590

Thr Leu Ala Ile Arg Val Leu Ala Gly Ile Pro Ala Pro Val Tyr Phe
                595                 600                 605

Gly Val Leu Ile Asp Thr Ser Cys Leu Lys Trp Gly Phe Lys Arg Cys
                610                 615                 620

Gly Ser Arg Gly Ser Cys Arg Leu Tyr Asp Ser Asn Val Phe Arg His
625                 630                 635                 640

Ile Tyr Leu Gly Leu Thr Val Ile Leu Gly Thr Val Ser Ile Leu Leu
                645                 650                 655

Ser Ile Ala Val Leu Phe Ile Leu Lys Lys Asn Tyr Val Ser Lys His
                660                 665                 670

Arg Ser Phe Ile Thr Lys Arg Glu Arg Thr Met Val Ser Thr Arg Phe
                675                 680                 685

Gln Lys Glu Asn Tyr Thr Thr Ser Asp His Leu Leu Gln Pro Asn Tyr
                690                 695                 700

Trp Pro Gly Lys Glu Thr Gln Leu
705                 710

<210> SEQ ID NO 11
<211> LENGTH: 2763
<212> TYPE: DNA
<213> ORGANISM: Homo sapiens

<400> SEQUENCE: 11
ggcacgaggc gctgcgcggc gcggcggccg ggccctcgag acggggacgg acacaccagc     60
ccctcggata ccacttggcc actcccgctg aggccactcc cactgcgtgg ctgaagcctc    120
gaggtcacca ggcggaggcg cggagatgcc cctgcatcag ctgggggaca agccgctcac    180
cttccccagc cccaactcag ccatggaaaa cgggcttgac cacaccccac ccagcaggag    240
ggcatccccg ggcacacccc tgagcccgg gtccctccgc tccgctgccc atagccccct    300
ggacaccagc aagcagcccc tctgccagct ctgggccgag aagcatggcg cccgggggac    360

| | | |
|---|---|---|
| ccatgaggtg cggtacgtct cggccgggca gagcgtggcg tgcggctggt gggccttcgc | 420 |
| accgccgtgc ctgcaggtcc tcaacacgcc caagggcatc ctgttcttcc tgtgtgcggc | 480 |
| cgcattcctg caggggatga ctgtgaatgg cttcatcaac acagtcatca cctccctgga | 540 |
| gcgccgctat gacctgcaca gctaccagag cgggctcatc gccagctcct acgacattgc | 600 |
| cgcctgcctc tgcctcacct tcgtcagcta cttcggggc tcagggcaca agccgcgctg | 660 |
| gctgggctgg ggcgtgctgc ttatgggcac ggggtcgctg tgttcgcgc tgccccactt | 720 |
| cacggctggc cgctatgagg tggagttgga cgcgggtgtc aggacgtgcc ctgccaaccc | 780 |
| cggcgcggtg tgtgcggaca gcacctcggg cctgtcccgc taccagctgg tcttcatgct | 840 |
| gggccagttc ctgcatggcg tgggtgccac acccctctac acgctgggcg tcacctacct | 900 |
| ggatgagaac gtcaagtcca gctgctcgcc cgtctacatt gccatcttct acacagcggc | 960 |
| catcctgggc ccagctgccg gctacctgat tggaggtgcc ctgctgaata tctacacgga | 1020 |
| aatgggccga cggacggagc tgaccaccga gagcccactg tgggtcggcg cctggtgggt | 1080 |
| cggcttcctg ggctctgggg ccgctgcttt cttcaccgcc gttcccatcc ttggttaccc | 1140 |
| tcggcagctg ccaggctccc agcgctacgc ggtcatgaga gcggcggaaa tgcaccagtt | 1200 |
| gaaggacagc agccgtgggg aggcgagcaa cccggacttt gggaaaacca tcagagacct | 1260 |
| gcctctctcc atctggctcc tgctgaagaa ccccacgttc atcctgctct gcctggccgg | 1320 |
| ggccaccgag gccactctca tcaccggcat gtccacgttc agccccaagt tcttggagtc | 1380 |
| ccagttcagc ctgagtgcct cagaagctgc caccttgttt gggtacctgg tggtgccagc | 1440 |
| gggtggtggc ggcaccttcc tgggcggctt ctttgtgaac aagctcaggc tccggggctc | 1500 |
| cgcggtcatc aagttctgcc tgttctgcac cgttgtcagc ctgctgggca tcctcgtctt | 1560 |
| ctcactgcac tgccccagtg tgcccatggc gggcgtcaca gccagctacg gcgggagcct | 1620 |
| cctgcccgaa ggccacctga acctaacggc tccctgcaac gctgcctgca gctgccagcc | 1680 |
| agaacactac agccctgtgt gcggctcgga cggcctcatg tacttctcac tgtgccacgc | 1740 |
| agggtgccct gcagccacgg agacgaatgt ggacggccag aaggtgtacc gagactgtag | 1800 |
| ctgtatccct cagaatcttt cctctggttt tggccatgcc actgcaggga atgcacttc | 1860 |
| aacttgtcag agaaagcccc tccttctggt tttcatattc gttgtaattt tctttacatt | 1920 |
| cctcagcagc attcctgcac taacggcaac tctacgatgt gtccgtgacc ctcagagatc | 1980 |
| cttgccctg gaatccagt ggattgtagt tagaatacta gggggcatcc cggggcccat | 2040 |
| cgccttcggc tgggtgatcg acaaggcctg tctgctgtgg caggaccagt gtggccagca | 2100 |
| gggctcctgc ttggtgtacc agaattcggc catgagccgc tacatactca tcatgggct | 2160 |
| cctgtacaag gtgctgggcg tcctcttctt tgccatagcc tgcttcttat acaagcccct | 2220 |
| gtcggagtct tcagatggcc tggaaacttg tctgcccagc cagtcctcag cccctgacag | 2280 |
| tgccacagat agccagctcc agagcagcgt ctgaccaccg cccgcgccca cccggccacg | 2340 |
| gcgggcactc agcatttcct gatgacagaa cagtgccgtt gggtgatgca atcacacggg | 2400 |
| aacttctatt tgacctgcaa ccttctactt aacctgtggt ttaaagtcgg ctgtgacctc | 2460 |
| ctgtccccag agctgtacgg ccctgcagtg ggtgggagga acttgcataa atatatattt | 2520 |
| atggacacac agtttgcatc agaacgtgtt tatagaatgt gttttatacc cgatcgtgtg | 2580 |
| tggtgtgcgt gaggacaaac tccgcagggg ctgtgaatcc cactgggagg gcggcgggcc | 2640 |
| tgcagcccga ggaaggcttg tgtgtcctca gttaaaactg tgcatatcga aatatatttt | 2700 |
| gttatttaag cctgcgaaaa aaaaaaaaaa aaaaaaaaaa aaaaaaaaaa aaaaaaaaaa | 2760 | aaa                                                                 2763

<210> SEQ ID NO 12
<211> LENGTH: 722
<212> TYPE: PRT
<213> ORGANISM: Homo sapiens

<400> SEQUENCE: 12

Met Pro Leu His Gln Leu Gly Asp Lys Pro Leu Thr Phe Pro Ser Pro
1               5                   10                  15

Asn Ser Ala Met Glu Asn Gly Leu Asp His Thr Pro Pro Ser Arg Arg
            20                  25                  30

Ala Ser Pro Gly Thr Pro Leu Ser Pro Gly Ser Leu Arg Ser Ala Ala
        35                  40                  45

His Ser Pro Leu Asp Thr Ser Lys Gln Pro Leu Cys Gln Leu Trp Ala
    50                  55                  60

Glu Lys His Gly Ala Arg Gly Thr His Glu Val Arg Tyr Val Ser Ala
65              70                  75                  80

Gly Gln Ser Val Ala Cys Gly Trp Trp Ala Phe Ala Pro Pro Cys Leu
                85                  90                  95

Gln Val Leu Asn Thr Pro Lys Gly Ile Leu Phe Phe Leu Cys Ala Ala
            100                 105                 110

Ala Phe Leu Gln Gly Met Thr Val Asn Gly Phe Ile Asn Thr Val Ile
        115                 120                 125

Thr Ser Leu Glu Arg Arg Tyr Asp Leu His Ser Tyr Gln Ser Gly Leu
    130                 135                 140

Ile Ala Ser Ser Tyr Asp Ile Ala Ala Cys Leu Cys Leu Thr Phe Val
145                 150                 155                 160

Ser Tyr Phe Gly Gly Ser Gly His Lys Pro Arg Trp Leu Gly Trp Gly
                165                 170                 175

Val Leu Leu Met Gly Thr Gly Ser Leu Val Phe Ala Leu Pro His Phe
            180                 185                 190

Thr Ala Gly Arg Tyr Glu Val Glu Leu Asp Ala Gly Val Arg Thr Cys
        195                 200                 205

Pro Ala Asn Pro Gly Ala Val Cys Ala Asp Ser Thr Ser Gly Leu Ser
    210                 215                 220

Arg Tyr Gln Leu Val Phe Met Leu Gly Gln Phe Leu His Gly Val Gly
225                 230                 235                 240

Ala Thr Pro Leu Tyr Thr Leu Gly Val Thr Tyr Leu Asp Glu Asn Val
                245                 250                 255

Lys Ser Ser Cys Ser Pro Val Tyr Ile Ala Ile Phe Tyr Thr Ala Ala
            260                 265                 270

Ile Leu Gly Pro Ala Ala Gly Tyr Leu Ile Gly Gly Ala Leu Leu Asn
        275                 280                 285

Ile Tyr Thr Glu Met Gly Arg Arg Thr Glu Leu Thr Thr Glu Ser Pro
    290                 295                 300

Leu Trp Val Gly Ala Trp Trp Val Gly Phe Leu Gly Ser Gly Ala Ala
305                 310                 315                 320

Ala Phe Phe Thr Ala Val Pro Ile Leu Gly Tyr Pro Arg Gln Leu Pro
                325                 330                 335

Gly Ser Gln Arg Tyr Ala Val Met Arg Ala Ala Glu Met His Gln Leu
            340                 345                 350

Lys Asp Ser Ser Arg Gly Glu Ala Ser Asn Pro Asp Phe Gly Lys Thr
        355                 360                 365

-continued

```
Ile Arg Asp Leu Pro Leu Ser Ile Trp Leu Leu Lys Asn Pro Thr
    370                 375                 380
Phe Ile Leu Leu Cys Leu Ala Gly Ala Thr Glu Ala Thr Leu Ile Thr
385                 390                 395                 400
Gly Met Ser Thr Phe Ser Pro Lys Phe Leu Glu Ser Gln Phe Ser Leu
                405                 410                 415
Ser Ala Ser Glu Ala Ala Thr Leu Phe Gly Tyr Leu Val Val Pro Ala
                420                 425                 430
Gly Gly Gly Gly Thr Phe Leu Gly Gly Phe Val Asn Lys Leu Arg
            435                 440                 445
Leu Arg Gly Ser Ala Val Ile Lys Phe Cys Leu Phe Cys Thr Val Val
    450                 455                 460
Ser Leu Leu Gly Ile Leu Val Phe Ser Leu His Cys Pro Ser Val Pro
465                 470                 475                 480
Met Ala Gly Val Thr Ala Ser Tyr Gly Gly Ser Leu Leu Pro Glu Gly
                485                 490                 495
His Leu Asn Leu Thr Ala Pro Cys Asn Ala Ala Cys Ser Cys Gln Pro
                500                 505                 510
Glu His Tyr Ser Pro Val Cys Gly Ser Asp Gly Leu Met Tyr Phe Ser
            515                 520                 525
Leu Cys His Ala Gly Cys Pro Ala Ala Thr Glu Thr Asn Val Asp Gly
    530                 535                 540
Gln Lys Val Tyr Arg Asp Cys Ser Cys Ile Pro Gln Asn Leu Ser Ser
545                 550                 555                 560
Gly Phe Gly His Ala Thr Ala Gly Lys Cys Thr Ser Thr Cys Gln Arg
                565                 570                 575
Lys Pro Leu Leu Leu Val Phe Ile Phe Val Ile Phe Phe Thr Phe
                580                 585                 590
Leu Ser Ser Ile Pro Ala Leu Thr Ala Thr Leu Arg Cys Val Arg Asp
    595                 600                 605
Pro Gln Arg Ser Phe Ala Leu Gly Ile Gln Trp Ile Val Arg Ile
610                 615                 620
Leu Gly Gly Ile Pro Gly Pro Ile Ala Phe Gly Trp Val Ile Asp Lys
625                 630                 635                 640
Ala Cys Leu Leu Trp Gln Asp Gln Cys Gly Gln Gly Ser Cys Leu
                645                 650                 655
Val Tyr Gln Asn Ser Ala Met Ser Arg Tyr Ile Leu Ile Met Gly Leu
                660                 665                 670
Leu Tyr Lys Val Leu Gly Val Leu Phe Phe Ala Ile Ala Cys Phe Leu
    675                 680                 685
Tyr Lys Pro Leu Ser Glu Ser Ser Asp Gly Leu Glu Thr Cys Leu Pro
    690                 695                 700
Ser Gln Ser Ser Ala Pro Asp Ser Ala Thr Asp Ser Gln Leu Gln Ser
705                 710                 715                 720
Ser Val
```

<210> SEQ ID NO 13
<211> LENGTH: 20
<212> TYPE: DNA
<213> ORGANISM: Homo sapiens

<400> SEQUENCE: 13
accctgtcta gcaggttgca                                                    20

```
<210> SEQ ID NO 14
<211> LENGTH: 19
<212> TYPE: DNA
<213> ORGANISM: Homo sapiens

<400> SEQUENCE: 14
ctgtcggagt cttcagatg                                                19

<210> SEQ ID NO 15
<211> LENGTH: 20
<212> TYPE: DNA
<213> ORGANISM: Homo sapiens

<400> SEQUENCE: 15
tccatcacag cctcctacgc                                               20

<210> SEQ ID NO 16
<211> LENGTH: 20
<212> TYPE: DNA
<213> ORGANISM: Homo sapiens

<400> SEQUENCE: 16
tgcctctact ctgaccctag                                               20

<210> SEQ ID NO 17
<211> LENGTH: 20
<212> TYPE: DNA
<213> ORGANISM: Homo sapiens

<400> SEQUENCE: 17
ggagcagtca ttgacaccac                                               20

<210> SEQ ID NO 18
<211> LENGTH: 21
<212> TYPE: DNA
<213> ORGANISM: Homo sapiens

<400> SEQUENCE: 18
tgctgggagt acaacgtgac g                                             21

<210> SEQ ID NO 19
<211> LENGTH: 20
<212> TYPE: DNA
<213> ORGANISM: Homo sapiens

<400> SEQUENCE: 19
acaaggagga tggactgcag                                               20

<210> SEQ ID NO 20
<211> LENGTH: 20
<212> TYPE: DNA
<213> ORGANISM: Homo sapiens

<400> SEQUENCE: 20
caggaatccc agctccagtg                                               20

<210> SEQ ID NO 21
<211> LENGTH: 20
<212> TYPE: DNA
<213> ORGANISM: Homo sapiens

<400> SEQUENCE: 21
gctacaaccc aactactggc                                               20
```

<210> SEQ ID NO 22
<211> LENGTH: 20
<212> TYPE: DNA
<213> ORGANISM: Homo sapiens

<400> SEQUENCE: 22
gggactaact gtgatactgg                                           20

<210> SEQ ID NO 23
<211> LENGTH: 661
<212> TYPE: PRT
<213> ORGANISM: Rat

<400> SEQUENCE: 23

```
Met Gly Lys Ser Glu Lys Arg Val Ala Thr His Gly Val Arg Cys Phe
1               5                   10                  15

Ala Lys Ile Lys Met Phe Leu Leu Ala Leu Thr Cys Ala Tyr Val Ser
            20                  25                  30

Lys Ser Leu Ser Gly Thr Tyr Met Asn Ser Met Leu Thr Gln Ile Glu
        35                  40                  45

Arg Gln Phe Gly Ile Pro Thr Ser Ile Val Gly Leu Ile Asn Gly Ser
    50                  55                  60

Phe Glu Ile Gly Asn Leu Leu Ile Ile Phe Val Ser Tyr Phe Gly
65                  70                  75                  80

Thr Lys Leu His Arg Pro Ile Met Ile Gly Val Gly Cys Ala Val Met
                85                  90                  95

Gly Leu Gly Cys Phe Leu Ile Ser Leu Pro His Phe Leu Met Gly Gln
            100                 105                 110

Tyr Glu Tyr Glu Thr Ile Leu Pro Thr Ser Asn Val Ser Ser Asn Ser
        115                 120                 125

Phe Phe Cys Val Glu Asn Arg Ser Gln Thr Leu Asn Pro Thr Gln Asp
130                 135                 140

Pro Ser Glu Cys Val Lys Glu Met Lys Ser Leu Met Trp Ile Tyr Val
145                 150                 155                 160

Leu Val Gly Asn Ile Ile Arg Gly Ile Gly Glu Thr Pro Ile Met Pro
                165                 170                 175

Leu Gly Ile Ser Tyr Ile Glu Asp Phe Ala Lys Ser Glu Asn Ser Pro
            180                 185                 190

Leu Tyr Ile Gly Ile Leu Glu Thr Gly Met Thr Ile Gly Pro Leu Ile
        195                 200                 205

Gly Leu Leu Leu Ala Ser Ser Cys Ala Asn Ile Tyr Val Asp Ile Glu
    210                 215                 220

Ser Val Asn Thr Asp Asp Leu Thr Ile Thr Pro Thr Asp Thr Arg Trp
225                 230                 235                 240

Val Gly Ala Trp Trp Ile Gly Phe Leu Val Cys Ala Gly Val Asn Ile
                245                 250                 255

Leu Thr Ser Phe Pro Phe Phe Phe Pro Lys Thr Leu Pro Lys Glu
            260                 265                 270

Gly Leu Gln Glu Asn Val Asp Gly Thr Glu Asn Ala Lys Glu Lys Lys
        275                 280                 285

His Arg Lys Lys Ala Lys Glu Glu Lys Arg Gly Ile Thr Lys Asp Phe
    290                 295                 300

Phe Val Phe Met Lys Ser Leu Ser Cys Asn Pro Ile Tyr Met Leu Phe
305                 310                 315                 320
```

-continued

Ile Leu Ile Ser Val Leu Gln Phe Asn Ala Phe Ile Asn Ser Phe Thr
            325                 330                 335

Phe Met Pro Lys Tyr Leu Glu Gln Gln Tyr Gly Lys Ser Thr Ala Glu
            340                 345                 350

Val Val Phe Leu Met Gly Leu Tyr Met Leu Pro Pro Ile Cys Leu Gly
            355                 360                 365

Tyr Leu Ile Gly Gly Leu Ile Met Lys Lys Phe Lys Val Thr Val Lys
        370                 375                 380

Lys Ala Ala His Leu Ala Phe Trp Leu Cys Leu Ser Glu Tyr Leu Leu
385                 390                 395                 400

Ser Phe Leu Ser Tyr Val Met Thr Cys Asp Asn Phe Pro Val Ala Gly
            405                 410                 415

Leu Thr Thr Ser Tyr Glu Gly Val Gln His Gln Leu Tyr Val Glu Asn
            420                 425                 430

Lys Val Leu Ala Asp Cys Asn Thr Arg Cys Asn Cys Ser Thr Asn Thr
            435                 440                 445

Trp Asp Pro Val Cys Gly Asp Asn Gly Leu Ala Tyr Met Ser Ala Cys
        450                 455                 460

Leu Ala Gly Cys Glu Lys Ser Val Gly Thr Gly Thr Asn Met Val Phe
465                 470                 475                 480

Gln Asn Cys Ser Cys Ile Gln Ser Ser Gly Asn Ser Ser Ala Val Leu
            485                 490                 495

Gly Leu Cys Asn Lys Gly Pro Asp Cys Ala Asn Lys Leu Gln Tyr Phe
            500                 505                 510

Leu Ile Ile Ala Ile Phe Gly Cys Phe Ile Tyr Ser Leu Ala Gly Ile
        515                 520                 525

Pro Gly Tyr Met Val Leu Leu Arg Cys Ile Lys Ser Glu Glu Lys Ser
        530                 535                 540

Leu Gly Val Gly Leu His Ala Phe Cys Ile Arg Ile Leu Ala Gly Ile
545                 550                 555                 560

Pro Ala Pro Ile Tyr Phe Gly Ala Leu Ile Asp Arg Thr Cys Leu His
            565                 570                 575

Trp Gly Thr Leu Lys Cys Gly Glu Pro Gly Ala Cys Arg Met Tyr Asp
            580                 585                 590

Ile Asn Ser Phe Arg Arg Leu Tyr Leu Gly Leu Pro Ala Ala Leu Arg
        595                 600                 605

Gly Ala Ser Phe Val Pro Ala Phe Phe Ile Leu Arg Leu Thr Arg Thr
        610                 615                 620

Phe Gln Phe Pro Gly Asp Ile Glu Ser Ser Lys Thr Asp His Ala Glu
625                 630                 635                 640

Met Lys Leu Thr Leu Lys Glu Ser Glu Cys Thr Glu Val Leu Arg Ser
            645                 650                 655

Lys Val Thr Glu Asp
            660

<210> SEQ ID NO 24
<211> LENGTH: 670
<212> TYPE: PRT
<213> ORGANISM: Rat

<400> SEQUENCE: 24

Met Gly Glu Thr Glu Lys Arg Val Ala Thr His Glu Val Arg Cys Phe
1               5                   10                  15

Ser Lys Ile Lys Met Phe Leu Leu Ala Leu Thr Trp Ala Tyr Val Ser
            20                  25                  30

```
Gln Ser Leu Ser Gly Ile Tyr Met Asn Thr Met Leu Thr Gln Ile Glu
         35                  40                  45

Arg Gln Phe Asp Ile Pro Ile Ser Ile Val Gly Phe Ile Asn Gly Ser
         50                  55                  60

Phe Glu Ile Gly Asn Phe Leu Ile Ile Phe Val Ser Tyr Phe Gly
 65                  70                  75                  80

Thr Lys Leu His Arg Pro Ile Met Ile Gly Val Gly Cys Val Ile Met
                 85                  90                  95

Gly Leu Gly Cys Phe Leu Met Ser Leu Pro His Phe Leu Met Gly Arg
            100                 105                 110

Tyr Glu Tyr Glu Thr Thr Ile Ser Pro Thr Ser Asn Leu Ser Ser Asn
        115                 120                 125

Ser Phe Leu Cys Met Glu Asn Arg Ser Gln Thr Leu Lys Pro Thr Gln
    130                 135                 140

Asp Pro Ala Glu Cys Ile Lys Glu Met Lys Ser Leu Met Trp Ile Tyr
145                 150                 155                 160

Val Leu Val Gly Asn Ile Ile Arg Gly Ile Gly Glu Thr Pro Ile Met
                165                 170                 175

Pro Leu Gly Ile Ser Tyr Ile Glu Asp Phe Ala Lys Ser Glu Asn Ser
            180                 185                 190

Pro Leu Tyr Ile Gly Ile Leu Glu Thr Gly Lys Val Phe Gly Pro Ile
        195                 200                 205

Val Gly Leu Leu Leu Gly Ser Phe Cys Ala Ser Ile Tyr Val Asp Thr
    210                 215                 220

Gly Ser Val Asn Thr Asp Asp Leu Thr Ile Thr Pro Thr Asp Thr Arg
225                 230                 235                 240

Trp Val Gly Ala Trp Trp Ile Gly Phe Leu Ile Cys Ala Gly Val Asn
                245                 250                 255

Ile Leu Ser Ser Ile Pro Phe Phe Phe Pro Lys Thr Leu Pro Lys
            260                 265                 270

Glu Gly Leu Gln Asp Asp Val Asp Gly Thr Asn Asn Asp Lys Glu Glu
        275                 280                 285

Lys His Arg Glu Lys Ala Lys Glu Glu Asn Arg Gly Ile Thr Lys Asp
    290                 295                 300

Phe Leu Pro Phe Met Lys Ser Leu Ser Cys Asn Pro Ile Tyr Met Leu
305                 310                 315                 320

Leu Ile Leu Thr Ser Val Leu Gln Ile Asn Ala Phe Ile Asn Met Phe
                325                 330                 335

Thr Phe Leu Pro Lys Tyr Leu Glu Gln Gln Tyr Gly Lys Ser Thr Ala
            340                 345                 350

Glu Val Val Leu Leu Ile Gly Val Tyr Asn Leu Pro Pro Ile Cys Ile
        355                 360                 365

Gly Tyr Leu Leu Ile Gly Phe Ile Met Lys Lys Phe Lys Ile Thr Val
    370                 375                 380

Lys Lys Ala Ala Tyr Met Ala Phe Cys Leu Ser Leu Phe Glu Tyr Leu
385                 390                 395                 400

Leu Tyr Phe Leu His Phe Met Ile Thr Cys Asp Asn Phe Pro Val Ala
                405                 410                 415

Gly Leu Thr Ala Leu Tyr Glu Gly Val His His Pro Leu Tyr Val Glu
            420                 425                 430

Asn Lys Val Leu Ala Asp Cys Asn Arg Gly Cys Ser Cys Ser Thr Asn
        435                 440                 445
```

```
Ser Trp Asp Pro Val Cys Gly Asp Asn Gly Leu Ala Tyr Met Ser Ala
    450                 455                 460

Cys Leu Ala Gly Cys Lys Lys Ser Val Gly Thr Gly Thr Asn Met Val
465                 470                 475                 480

Phe Gln Asn Cys Ser Cys Ile Arg Ser Ser Gly Asn Ser Ser Ala Val
                    485                 490                 495

Leu Gly Leu Cys Lys Lys Gly Pro Glu Cys Ala Asn Lys Leu Gln Tyr
                500                 505                 510

Phe Leu Ile Met Ser Val Ile Gly Ser Phe Ile Tyr Ser Ile Thr Ala
            515                 520                 525

Ile Pro Gly Tyr Met Val Leu Arg Cys Ile Lys Pro Glu Lys Lys
        530                 535                 540

Ser Leu Gly Ile Gly Leu His Ala Phe Cys Thr Arg Val Phe Ala Gly
545                 550                 555                 560

Ile Pro Ala Pro Ile Tyr Phe Gly Ala Leu Ile Asp Arg Thr Cys Leu
                565                 570                 575

His Trp Gly Thr Leu Lys Cys Gly Glu Pro Gly Ala Cys Arg Met Tyr
                580                 585                 590

Asn Ile Asn Asn Phe Arg Arg Ile Tyr Leu Val Leu Pro Ala Ala Leu
            595                 600                 605

Arg Gly Ser Ser Tyr Leu Pro Ala Leu Phe Ile Leu Ile Leu Met Arg
610                 615                 620

Lys Phe Gln Phe Pro Gly Glu Ile Asp Ser Ser Glu Thr Glu Leu Ala
625                 630                 635                 640

Glu Met Lys Ile Thr Val Lys Lys Ser Glu Cys Thr Asp Val His Gly
                645                 650                 655

Ser Pro Gln Val Glu Asn Asp Gly Glu Leu Lys Thr Arg Leu
                660                 665                 670

<210> SEQ ID NO 25
<211> LENGTH: 669
<212> TYPE: PRT
<213> ORGANISM: Rat

<400> SEQUENCE: 25

Met Gly Asp Leu Glu Lys Gly Ala Ala Thr His Gly Ala Gly Cys Phe
1               5                   10                  15

Ala Lys Ile Lys Val Phe Leu Met Ala Leu Thr Cys Ala Tyr Val Ser
            20                  25                  30

Lys Ser Leu Ser Gly Thr Phe Met Ser Ser Met Leu Thr Gln Ile Glu
        35                  40                  45

Arg Gln Phe Gly Ile Pro Thr Ala Ile Val Gly Phe Ile Asn Gly Ser
    50                  55                  60

Phe Glu Ile Gly Asn Leu Leu Leu Ile Ile Phe Val Ser Tyr Phe Gly
65                  70                  75                  80

Met Lys Leu His Arg Pro Ile Val Ile Gly Val Gly Cys Ala Val Met
                85                  90                  95

Gly Leu Gly Cys Phe Ile Ile Ser Leu Pro His Phe Leu Met Gly Arg
            100                 105                 110

Tyr Glu Tyr Glu Thr Thr Ile Leu Pro Thr Ser Asn Leu Ser Ser Asn
        115                 120                 125

Ser Phe Leu Cys Met Glu Asn Gln Thr Gln Thr Leu Asn Pro Ala Gln
    130                 135                 140

Asp Pro Ala Glu Cys Val Lys Glu Val Lys Ser Leu Met Trp Ile Tyr
145                 150                 155                 160
```

```
Val Leu Val Gly Asn Ile Ile Arg Gly Ile Gly Glu Thr Pro Ile Met
                165                 170                 175

Pro Leu Gly Val Ser Tyr Ile Glu Asn Phe Ala Lys Ser Glu Asn Ser
            180                 185                 190

Pro Leu Tyr Ile Gly Ile Leu Glu Thr Gly Lys Met Ile Gly Pro Ile
            195                 200                 205

Phe Gly Leu Leu Leu Gly Ser Phe Cys Ala Ser Ile Tyr Val Asp Thr
            210                 215                 220

Gly Ser Val Asn Thr Asp Asp Leu Thr Ile Thr Pro Thr Asp Ile Arg
225                 230                 235                 240

Trp Val Gly Ala Trp Trp Ile Gly Phe Leu Val Cys Ala Gly Val Asn
                245                 250                 255

Ile Leu Ile Ser Ile Pro Phe Phe Phe Pro Lys Thr Leu Pro Lys
            260                 265                 270

Glu Gly Leu Gln Glu Asn Val Asp Gly Thr Glu Asn Ala Lys Glu Glu
            275                 280                 285

Ser Thr Glu Lys Arg Pro Arg Lys Lys Asn Arg Gly Ile Thr Lys Asp
            290                 295                 300

Phe Phe Pro Phe Leu Lys Ser Pro Val Leu Gln Pro Asp Leu His Ala
305                 310                 315                 320

Val His Pro Tyr Lys Val Leu Gln Val Asn Ala Phe Asn Ile Tyr Phe
            325                 330                 335

Ser Phe Leu Pro Lys Tyr Leu Glu Asn Gln Tyr Gly Lys Ser Thr Ala
            340                 345                 350

Glu Val Ile Phe Leu Met Gly Val Tyr Asn Leu Pro Ala Ile Cys Ile
            355                 360                 365

Gly Tyr Leu Ile Ala Gly Phe Met Met Lys Lys Phe Lys Ile Thr Val
            370                 375                 380

Lys Thr Ala Ala Phe Leu Arg Phe Cys Leu Ser Leu Ser Glu Tyr Ser
385                 390                 395                 400

Phe Gly Phe Cys Asn Phe Leu Ile Thr Cys Asp Asn Val Pro Val Ala
            405                 410                 415

Gly Leu Thr Asn Ser Tyr Glu Arg Asp Gln Lys Pro Leu Tyr Leu Glu
            420                 425                 430

Asn Asn Val Leu Ala Asp Cys Asn Thr Arg Cys Ser Cys Leu Thr Lys
            435                 440                 445

Thr Trp Asp Pro Val Cys Gly Asp Asn Gly Leu Ala Tyr Met Ser Ala
            450                 455                 460

Cys Leu Ala Gly Cys Glu Lys Ser Val Gly Thr Gly Thr Asn Met Val
465                 470                 475                 480

Phe His Asn Cys Ser Cys Ile Gln Ser Pro Gly Asn Ser Ser Ala Val
            485                 490                 495

Leu Gly Leu Cys Asn Lys Gly Pro Glu Cys Thr Asn Lys Leu Gln Tyr
            500                 505                 510

Leu Leu Ile Leu Ser Gly Phe Leu Ser Ile Leu Tyr Ser Phe Ala Ala
            515                 520                 525

Ile Pro Gly Tyr Met Val Phe Leu Arg Cys Ile Lys Ser Glu Glu Lys
            530                 535                 540

Ser Leu Gly Ile Gly Ile His Ala Phe Cys Ile Arg Val Phe Ala Gly
545                 550                 555                 560

Ile Pro Ala Pro Ile Tyr Phe Gly Ala Leu Ile Asp Arg Thr Cys Leu
            565                 570                 575
```

-continued

```
His Trp Gly Thr Gln Lys Cys Gly Ala Pro Gly Arg Arg Met Tyr Asp
            580                 585                 590

Ile Asn Ser Phe Arg Arg Ile Tyr Leu Gly Met Ser Ala Ala Leu Arg
            595                 600                 605

Gly Ser Ser Tyr Leu Pro Ala Phe Val Ile Val Leu Thr Arg Lys
            610                 615                 620

Phe Ser Leu Pro Gly Lys Ile Asn Ser Ser Glu Met Glu Ile Ala Glu
625                 630                 635                 640

Met Lys Leu Thr Glu Lys Glu Ser Gln Cys Thr Asp Val His Arg Asn
            645                 650                 655

Pro Lys Phe Lys Asn Asp Gly Glu Leu Lys Thr Lys Leu
            660                 665

<210> SEQ ID NO 26
<211> LENGTH: 670
<212> TYPE: PRT
<213> ORGANISM: Rat

<400> SEQUENCE: 26

Met Glu Glu Thr Glu Lys Lys Ile Ala Thr Gln Glu Gly Arg Leu Phe
1               5                   10                  15

Ser Lys Met Lys Val Phe Leu Leu Ser Leu Thr Cys Ala Cys Leu Thr
            20                  25                  30

Lys Ser Leu Ser Gly Val Tyr Met Asn Ser Met Leu Thr Gln Ile Glu
        35                  40                  45

Arg Gln Phe Asp Ile Ser Thr Ser Val Ala Gly Leu Ile Asn Gly Ser
    50                  55                  60

Phe Glu Ile Gly Asn Leu Phe Phe Ile Val Phe Val Ser Tyr Phe Gly
65                  70                  75                  80

Thr Lys Leu His Arg Pro Val Val Ile Gly Ile Gly Cys Val Ile Met
            85                  90                  95

Gly Leu Gly Cys Leu Leu Met Ser Leu Pro His Phe Met Gly Arg
            100                 105                 110

Tyr Glu Tyr Glu Thr Thr Ile Ser Pro Thr Gly Asn Leu Ser Ser Asn
            115                 120                 125

Ser Phe Leu Cys Met Glu Asn Arg Thr Gln Thr Leu Lys Pro Thr Gln
    130                 135                 140

Asp Pro Ala Glu Cys Val Lys Glu Met Lys Ser Leu Met Trp Ile Cys
145                 150                 155                 160

Val Met Val Gly Asn Ile Ile Arg Gly Ile Gly Glu Thr Pro Ile Val
            165                 170                 175

Pro Leu Gly Ile Ser Tyr Ile Glu Asp Phe Ala Lys Ser Glu Asn Ser
            180                 185                 190

Pro Leu Tyr Ile Gly Ile Leu Glu Met Gly Lys Val Ala Gly Pro Ile
            195                 200                 205

Phe Gly Leu Leu Leu Gly Ser Tyr Cys Ala Gln Ile Tyr Val Asp Ile
    210                 215                 220

Gly Ser Val Asn Thr Asp Asp Leu Thr Ile Thr Pro Ser Asp Thr Arg
225                 230                 235                 240

Trp Val Gly Ala Trp Trp Ile Gly Phe Leu Val Cys Ala Gly Val Asn
            245                 250                 255

Ile Leu Thr Ser Ile Pro Phe Phe Leu Pro Lys Ala Leu Pro Lys
        260                 265                 270

Lys Gly Gln Gln Glu Asn Val Ala Val Thr Lys Asp Gly Lys Val Glu
    275                 280                 285
```

-continued

```
Lys Tyr Gly Gly Gln Ala Arg Glu Glu Asn Leu Gly Ile Thr Lys Asp
    290                 295                 300
Phe Leu Thr Phe Met Lys Arg Leu Phe Cys Asn Pro Ile Tyr Met Leu
305                 310                 315                 320
Phe Ile Leu Thr Ser Val Leu Gln Val Asn Gly Phe Ile Asn Lys Phe
                325                 330                 335
Thr Phe Leu Pro Lys Tyr Leu Glu Gln Gln Tyr Gly Lys Ser Thr Ala
                340                 345                 350
Glu Ala Ile Phe Leu Ile Gly Val Tyr Ser Leu Pro Pro Ile Cys Leu
                355                 360                 365
Gly Tyr Leu Ile Gly Gly Phe Ile Met Lys Lys Phe Lys Ile Thr Val
    370                 375                 380
Lys Lys Ala Ala Tyr Leu Ala Phe Cys Leu Ser Val Phe Glu Tyr Leu
385                 390                 395                 400
Leu Phe Leu Cys His Phe Met Leu Thr Cys Asp Asn Ala Ala Val Ala
                405                 410                 415
Gly Leu Thr Thr Ser Tyr Lys Gly Val Gln His Gln Leu His Val Glu
                420                 425                 430
Ser Lys Val Leu Ala Asp Cys Asn Thr Arg Cys Ser Cys Ser Thr Asn
    435                 440                 445
Thr Trp Asp Pro Val Cys Gly Asp Asn Gly Val Ala Tyr Met Ser Ala
    450                 455                 460
Cys Leu Ala Gly Cys Lys Lys Phe Val Gly Thr Gly Thr Asn Met Val
465                 470                 475                 480
Phe Gln Asp Cys Ser Cys Ile Gln Ser Leu Gly Asn Ser Ser Ala Val
                485                 490                 495
Leu Gly Leu Cys Lys Lys Gly Pro Glu Cys Ala Asn Arg Leu Gln Tyr
                500                 505                 510
Phe Leu Ile Leu Thr Ile Ile Ser Phe Ile Tyr Ser Leu Thr Ala
                515                 520                 525
Ile Pro Gly Tyr Met Val Phe Leu Arg Cys Val Lys Ser Glu Lys
    530                 535                 540
Ser Leu Gly Val Gly Leu His Thr Phe Cys Ile Arg Val Phe Ala Gly
545                 550                 555                 560
Ile Pro Ala Pro Val Tyr Phe Gly Ala Leu Ile Asp Arg Thr Cys Leu
                565                 570                 575
His Trp Gly Thr Leu Lys Cys Gly Gln Arg Gly Ala Cys Arg Met Tyr
                580                 585                 590
Asp Ile Asn Ser Phe Arg His Ile Tyr Leu Gly Leu Pro Ile Ala Leu
                595                 600                 605
Arg Gly Ser Ser Tyr Leu Pro Ala Phe Phe Ile Leu Ile Leu Met Arg
    610                 615                 620
Lys Phe Gln Phe Pro Gly Asp Ile Asp Ser Ser Ala Thr Asp His Thr
625                 630                 635                 640
Glu Met Met Leu Gly Glu Lys Glu Ser Glu His Thr Asp Val His Gly
                645                 650                 655
Ser Pro Gln Val Glu Asn Asp Gly Glu Leu Lys Thr Lys Leu
                660                 665                 670

<210> SEQ ID NO 27
<211> LENGTH: 670
<212> TYPE: PRT
<213> ORGANISM: Homo sapiens
```

-continued

```
<400> SEQUENCE: 27

Met Gly Glu Thr Glu Lys Arg Ile Glu Thr His Arg Ile Arg Cys Leu
1               5                   10                  15

Ser Lys Leu Lys Met Phe Leu Leu Ala Ile Thr Cys Ala Phe Val Ser
            20                  25                  30

Lys Thr Leu Ser Gly Ser Tyr Met Asn Ser Met Leu Thr Gln Ile Glu
        35                  40                  45

Arg Gln Phe Asn Ile Pro Thr Ser Leu Val Gly Phe Ile Asn Gly Ser
    50                  55                  60

Phe Glu Ile Gly Asn Leu Leu Ile Ile Phe Val Ser Tyr Phe Gly
65                  70                  75                  80

Thr Lys Leu His Arg Pro Ile Met Ile Gly Ile Gly Cys Val Val Met
                85                  90                  95

Gly Leu Gly Cys Phe Leu Lys Ser Leu Pro His Phe Leu Met Asn Gln
            100                 105                 110

Tyr Glu Tyr Glu Ser Thr Val Ser Val Ser Gly Asn Leu Ser Ser Asn
        115                 120                 125

Ser Phe Leu Cys Met Glu Asn Gly Thr Gln Ile Leu Arg Pro Thr Gln
    130                 135                 140

Asp Pro Ser Glu Cys Thr Lys Glu Val Lys Ser Leu Met Trp Val Tyr
145                 150                 155                 160

Val Leu Val Gly Asn Ile Val Arg Gly Met Gly Glu Thr Pro Ile Leu
                165                 170                 175

Pro Leu Gly Ile Ser Tyr Ile Glu Asp Phe Ala Lys Phe Glu Asn Ser
            180                 185                 190

Pro Leu Tyr Ile Gly Leu Val Glu Thr Gly Ala Ile Ile Gly Pro Leu
        195                 200                 205

Ile Gly Leu Leu Leu Ala Ser Phe Cys Ala Asn Val Tyr Val Asp Thr
    210                 215                 220

Gly Phe Val Asn Thr Asp Asp Leu Ile Ile Thr Pro Thr Asp Thr Arg
225                 230                 235                 240

Trp Val Gly Ala Trp Trp Phe Gly Phe Leu Ile Cys Ala Gly Val Asn
                245                 250                 255

Val Leu Thr Ala Ile Pro Phe Phe Phe Leu Pro Asn Thr Leu Pro Lys
            260                 265                 270

Glu Gly Leu Glu Thr Asn Ala Asp Ile Ile Lys Asn Glu Asn Glu Asp
        275                 280                 285

Lys Gln Lys Glu Glu Val Lys Lys Glu Lys Tyr Gly Ile Thr Lys Asp
    290                 295                 300

Phe Leu Pro Phe Met Lys Ser Leu Ser Cys Asn Pro Ile Tyr Met Leu
305                 310                 315                 320

Phe Ile Leu Val Ser Val Ile Gln Phe Asn Ala Phe Val Asn Met Ile
                325                 330                 335

Ser Phe Met Pro Lys Tyr Leu Glu Gln Gln Tyr Gly Ile Ser Ser Ser
            340                 345                 350

Asp Ala Ile Phe Leu Met Gly Ile Tyr Asn Leu Pro Pro Ile Cys Ile
        355                 360                 365

Gly Tyr Ile Ile Gly Gly Leu Ile Met Lys Lys Phe Lys Ile Thr Val
    370                 375                 380

Lys Gln Ala Ala His Ile Gly Cys Trp Leu Ser Leu Glu Tyr Leu
385                 390                 395                 400

Leu Tyr Phe Leu Ser Phe Leu Met Thr Cys Glu Asn Ser Ser Val Val
                405                 410                 415
```

Gly Ile Asn Thr Ser Tyr Glu Gly Ile Pro Gln Asp Leu Tyr Val Glu
            420                 425                 430

Asn Asp Ile Phe Ala Asp Cys Asn Val Asp Cys Asn Cys Pro Ser Lys
            435                 440                 445

Ile Trp Asp Pro Val Cys Gly Asn Asn Gly Leu Ser Tyr Leu Ser Ala
            450                 455                 460

Cys Leu Ala Gly Cys Glu Thr Ser Ile Gly Thr Gly Ile Asn Met Val
465                 470                 475                 480

Phe Gln Asn Cys Ser Cys Ile Gln Thr Ser Gly Asn Ser Ser Ala Val
            485                 490                 495

Leu Gly Leu Cys Asp Lys Gly Pro Asp Cys Ser Leu Met Leu Gln Tyr
            500                 505                 510

Phe Leu Ile Leu Ser Ala Met Ser Ser Phe Ile Tyr Ser Leu Ala Ala
            515                 520                 525

Ile Pro Gly Tyr Met Val Leu Leu Arg Cys Met Lys Ser Glu Glu Lys
            530                 535                 540

Ser Leu Gly Val Gly Leu His Thr Phe Cys Thr Arg Val Phe Ala Gly
545                 550                 555                 560

Ile Pro Ala Pro Ile Tyr Phe Gly Ala Leu Met Asp Ser Thr Cys Leu
            565                 570                 575

His Trp Gly Thr Leu Lys Cys Gly Glu Ser Gly Ala Cys Arg Ile Tyr
            580                 585                 590

Asp Ser Thr Thr Phe Arg Tyr Ile Tyr Leu Gly Leu Pro Ala Ala Leu
            595                 600                 605

Arg Gly Ser Ser Phe Val Pro Ala Leu Ile Ile Leu Ile Leu Leu Arg
            610                 615                 620

Lys Cys His Leu Pro Gly Glu Asn Ala Ser Ser Gly Thr Glu Leu Ile
625                 630                 635                 640

Glu Thr Lys Val Lys Gly Lys Glu Asn Glu Cys Lys Asp Ile Tyr Gln
            645                 650                 655

Lys Ser Thr Val Leu Lys Asp Asp Glu Leu Lys Thr Lys Leu
            660                 665                 670

<210> SEQ ID NO 28
<211> LENGTH: 643
<212> TYPE: PRT
<213> ORGANISM: Homo sapiens

<400> SEQUENCE: 28

Met Gly Leu Leu Pro Lys Leu Gly Val Ser Gln Gly Ser Asp Thr Ser
1               5                   10                  15

Thr Ser Arg Ala Gly Arg Cys Ala Arg Ser Val Phe Gly Asn Ile Lys
            20                  25                  30

Val Phe Val Leu Cys Gln Gly Leu Leu Gln Leu Cys Gln Leu Leu Tyr
            35                  40                  45

Ser Ala Tyr Phe Lys Ser Ser Leu Thr Thr Ile Glu Lys Arg Phe Gly
            50                  55                  60

Leu Ser Ser Ser Ser Gly Leu Ile Ser Ser Leu Asn Glu Ile Ser
65                  70                  75                  80

Asn Ala Ile Leu Ile Ile Phe Val Ser Tyr Phe Gly Ser Arg Val His
            85                  90                  95

Arg Pro Arg Leu Ile Gly Ile Gly Gly Leu Phe Leu Ala Ala Gly Ala
            100                 105                 110

Phe Ile Leu Thr Leu Pro His Phe Leu Ser Glu Pro Tyr Gln Tyr Thr

```
                115                 120                 125
Leu Ala Ser Thr Gly Asn Asn Ser Arg Leu Gln Ala Glu Leu Cys Gln
130                 135                 140

Lys His Trp Gln Asp Leu Pro Pro Ser Lys Cys His Ser Thr Thr Gln
145                 150                 155                 160

Asn Pro Gln Lys Glu Thr Ser Ser Met Trp Gly Leu Met Val Val Ala
                165                 170                 175

Gln Leu Leu Ala Gly Ile Gly Thr Val Pro Ile Gln Pro Phe Gly Ile
                180                 185                 190

Ser Tyr Val Asp Asp Phe Ser Glu Pro Ser Asn Ser Pro Leu Tyr Ile
                195                 200                 205

Ser Ile Leu Phe Ala Ile Ser Val Phe Gly Pro Ala Phe Gly Tyr Leu
210                 215                 220

Leu Gly Ser Ile Met Leu Gln Ile Phe Val Asp Tyr Gly Arg Val Asn
225                 230                 235                 240

Thr Ala Ala Val Asn Leu Val Pro Gly Asp Pro Arg Trp Ile Gly Ala
                245                 250                 255

Trp Trp Leu Gly Leu Leu Ile Ser Ser Ala Leu Leu Val Leu Thr Ser
                260                 265                 270

Phe Pro Phe Phe Phe Pro Arg Ala Met Pro Ile Gly Ala Lys Arg
                275                 280                 285

Ala Pro Ala Thr Ala Asp Glu Ala Arg Lys Leu Glu Glu Ala Lys Ser
290                 295                 300

Arg Gly Ser Leu Val Asp Phe Ile Lys Arg Phe Pro Cys Ile Phe Leu
305                 310                 315                 320

Arg Leu Leu Met Asn Ser Leu Phe Val Leu Val Leu Ala Gln Cys
                325                 330                 335

Thr Phe Ser Ser Val Ile Ala Gly Leu Ser Thr Phe Leu Asn Lys Phe
                340                 345                 350

Leu Glu Lys Gln Tyr Gly Thr Ser Ala Ala Tyr Ala Asn Phe Leu Ile
                355                 360                 365

Gly Ala Val Asn Leu Pro Ala Ala Leu Gly Met Leu Phe Gly Gly
                370                 375                 380

Ile Leu Met Lys Arg Phe Val Phe Ser Leu Gln Thr Ile Pro Arg Ile
385                 390                 395                 400

Ala Thr Thr Ile Ile Thr Ile Ser Met Ile Leu Cys Val Pro Leu Phe
                405                 410                 415

Phe Met Gly Cys Ser Thr Pro Thr Val Ala Glu Val Tyr Pro Pro Ser
                420                 425                 430

Thr Ser Ser Ser Ile His Pro Gln Ser Pro Ala Cys Arg Arg Asp Cys
                435                 440                 445

Ser Cys Pro Asp Ser Ile Phe His Pro Val Cys Gly Asp Asn Gly Ile
450                 455                 460

Glu Tyr Leu Ser Pro Cys His Ala Gly Cys Ser Asn Ile Asn Met Ser
465                 470                 475                 480

Ser Ala Thr Ser Lys Gln Leu Ile Tyr Leu Asn Cys Ser Cys Val Thr
                485                 490                 495

Gly Gly Ser Ala Ser Ala Lys Thr Gly Ser Cys Pro Val Pro Cys Ala
                500                 505                 510

His Phe Leu Leu Pro Ala Ile Phe Leu Ile Ser Phe Val Ser Leu Ile
                515                 520                 525

Ala Cys Ile Ser His Asn Pro Leu Tyr Met Met Val Leu Arg Val Val
                530                 535                 540
```

```
Asn Gln Glu Glu Lys Ser Phe Ala Ile Gly Val Gln Phe Leu Leu Met
545                 550                 555                 560

Arg Leu Leu Ala Trp Leu Pro Ser Pro Ala Leu Tyr Gly Leu Thr Ile
                565                 570                 575

Asp His Ser Cys Ile Arg Trp Asn Ser Leu Cys Leu Gly Arg Arg Gly
            580                 585                 590

Ala Cys Ala Tyr Tyr Asp Asn Asp Ala Leu Arg Asp Arg Tyr Leu Gly
        595                 600                 605

Leu Gln Met Gly Tyr Lys Ala Leu Gly Met Leu Leu Leu Cys Phe Ile
    610                 615                 620

Ser Trp Arg Val Lys Lys Asn Lys Glu Tyr Asn Val Gln Lys Ala Ala
625                 630                 635                 640

Gly Leu Ile

<210> SEQ ID NO 29
<211> LENGTH: 384
<212> TYPE: PRT
<213> ORGANISM: Artificial Sequence
<220> FEATURE:
<223> OTHER INFORMATION: Artificial Sequence = consensus sequence

<400> SEQUENCE: 29

Gly Glu Ala Cys Phe Ile Lys Phe Leu Leu Ala Leu Ala Leu Gly Tyr
1               5                   10                  15

Met Ser Leu Thr Gln Ile Glu Arg Arg Phe Ile Ser Ser Val Gly Leu
                20                  25                  30

Ile Gly Ser Phe Glu Ile Gly Asn Leu Leu Leu Ile Phe Val Ser Tyr
            35                  40                  45

Phe Gly Lys Leu His Arg Pro Ile Gly Gly Cys Met Gly Leu Gly Leu
        50                  55                  60

Leu Pro His Phe Leu Met Gly Tyr Glu Tyr Glu Asn Ser Leu Cys Asn
65                  70                  75                  80

Ser Leu Pro Asp Glu Cys Lys Glu Ser Leu Met Trp Ile Tyr Val Val
                85                  90                  95

Gly Asn Ile Leu Arg Gly Ile Gly Glu Thr Pro Ile Pro Leu Gly Ile
                100                 105                 110

Ser Tyr Ile Asp Asp Phe Ala Lys Glu Asn Ser Pro Leu Tyr Ile Gly
            115                 120                 125

Ile Leu Thr Gly Pro Gly Leu Leu Gly Ser Cys Ala Ile Tyr Val Asp
        130                 135                 140

Gly Val Asn Thr Asp Leu Ile Thr Pro Asp Pro Arg Trp Val Gly Ala
145                 150                 155                 160

Trp Trp Gly Phe Leu Cys Ala Gly Leu Ser Ile Pro Phe Phe Phe Phe
                165                 170                 175

Pro Lys Leu Pro Lys Gly Val Lys Asp Phe Lys Leu Leu Asn Pro Tyr
                180                 185                 190

Leu Leu Val Gln Asn Gly Thr Phe Leu Pro Lys Tyr Leu Glu Gln Gln
            195                 200                 205

Tyr Gly Ser Ser Ala Phe Leu Gly Leu Pro Cys Gly Gly Gly Ile Met
        210                 215                 220

Lys Lys Phe Lys Val Ala Ala Leu Ala Ser Leu Tyr Leu Leu Phe Cys
225                 230                 235                 240

Asn Val Ala Gly Leu Thr Ser Tyr Gly Glu Ala Asp Cys Asn Cys Ser
                245                 250                 255
```

-continued

```
Cys Trp Pro Val Cys Gly Asn Gly Tyr Ser Ala Cys Leu Ala Gly Cys
        260                 265             270

Ser Gly Thr Gly Asn Val Phe Asn Cys Ser Cys Ile Gly Asn Ser Ser
        275                 280             285

Ala Val Leu Gly Cys Lys Pro Cys Leu Tyr Phe Leu Ser Phe Ile Ser
    290                 295             300

Leu Ile Pro Gly Tyr Met Val Leu Arg Cys Val Lys Glu Glu Lys Ser
305                 310             315                 320

Leu Ala Gly His Arg Leu Ala Gly Ile Pro Ala Pro Ile Tyr Phe Gly
                325                 330             335

Ala Leu Ile Asp Thr Cys Leu His Trp Gly Thr Cys Gly Gly Ala Cys
            340             345             350

Arg Tyr Asp Phe Arg Tyr Leu Gly Leu Ala Leu Arg Ser Leu Ile Leu
            355             360             365

Leu Arg Lys Pro Ile Ser Ser Glu Lys Glu Ser Thr His Asp Glu Thr
370                 375                 380
```

ORGANIC ANION TRANSPORT PROTEINS

This application claims priority from provisional U.S. application Serial No. 60/135,081, filed May 20, 1999, which is incorporated herein by reference in its entirety.

FIELD OF THE INVENTION

The invention claims isolated nucleic acid encoding all or a portion of novel members of the organic anion transport protein ("OATP") designated OATP2, OATP-RP1, OATP-RP2, OATP-RP3, OATP-RP4 and OATP-RP5. Also claimed are vectors containing the nucleic acid sequences, host cells containing the vectors and polypeptides having all or part of the amino acid sequence of OATP2, OATP-RP1, OATP-RP2, OATP-RP3, OATP-RP4 and OATP-RP5. Tissue expression of the transporter is described as well as some of its substrates. Also claimed are uses for these novel OATPs, including for targeting drugs to specific tissues, for modulating the concentration of endogenous substrates, and for identifying a substrate capable of being transported by a novel OATP of the invention.

BACKGROUND OF THE INVENTION

The liver functions in the clearance of a large variety of metabolic products, drugs and other xenobiotics by transporting them across the sinusoidal membrane into the hepatocyte. Several classes of transport systems have been described that mediate these processes including the Na+/taurocholate cotransporter polypeptide, NTCP, in rat and human liver (Hagenbuch, B., et al. (1991) *Proc. Natl. Acad. Sci. USA* 88:10629–33; Hagenbuch, B. et al., (1994) *J. Clin. Invest.* 93:1326–31) and a family of organic anion transporting polypeptides (OATPs) that are principally expressed in liver, kidney and brain, and transport a broad spectrum of substrates in a sodium-independent manner (Meier, P. J., et al., (1997) *Hepatology* 26:1667–77; Wolkoff, A. W., (1996) *Semin. Liver Dis.* 16:121–127). The distribution of this latter family of transporters in liver, kidney and choroid plexus in the brain is thought to reflect common physiological requirements of these organs for the clearance of a multitide of organic anions. There are three OATP isoforms in the rat: roatp1 (Jacquemin, E., et al., (1994) *Proc. Natl. Acad. Sci. USA* 91:133–37); roatp2 (Noe, B. A., et al., (1997) *Proc. Natl. Acad. Sci. USA* 94:10346–50; and roatp3 (Abe, T., et al., (1998) *J. Biol. Chem.* 273:11395–401). In addition to bile acids, OATPs are known to transport a variety of other compounds. These include, depending on the transporter, unconjugated and conjugated steroids such as estrone sulfate, estradiol-17B-glucuronide, aldosterone, and cardiac glycosides (Boussuyt, X., et al., (1996) *J. Pharmacol. Exp. Ther.* 276:891–6; Boussuyt, X. (1996) *J. Hepatol.* 25:733–8; Kanai, N., et al., (1996) *Am. J. Physiol.* 270:F319–F325; Kanai, N., et al., (1996) *Am. J. Physiol.* 270:F326–F331; Noe, B. A., et al., (1997) *Proc. Natl. Acad. Sci. USA* 94:10346–50). Bromosulfophthalien (Jacquemin, E., et al., (1994) *Proc. Natl. Acad. Sci. USA* 91:133–7); mycotoxin (Kontaxi, M., et al., (1996) *J. Pharmacol. Exp. Ther.* 279:1507–13); leukotriene $C_4$ (Li, L., et al., (1 998) *J. Biol. Chem.* 273:16184–91); and thyroid hormone (Abe, T., et al., (1998) *J. Biol. Chem.* 273:11395) are additional substrates.

Several proteins have been identified. Jacquemin,E., et al., (1994) *Proc. Natl. Acad. Sci. U.S.A.*, 91:133–137 reported the first cloning and identification of a member of the OATP transporter family, namely the rat oatp1. The first cloning and identification of a human OATP was reported in Kullak-Ublick, G. A., et al., (1995) *Gastroenterology*, 109:1274–1282. Its expression was found in liver, kidney brain and other organs. The authors concluded, based on substrate specificities, that it was not the human orthologue of rat oatp1.

Substrate specificities of rat oatp1 are discussed in Kullak-Ublick, G. A. et al., (1994) *Hepatology*, 20:411–416, while substrate specificities of human OATP are discussed in Bossuyt, X., et al., (1996) *J. Hepatol.*, 25:733–738.

Data was later discovered showing that rat oatp1 is involved in the transport of steroids (Bossuyt, X., et al., (1996) *J. Pharmacol. Exp. Ther.*, 276:891–896), and that human OATP acts as a transporter for the psychoactive hormone DHEAS (Kullak-Ublick, G. A., et al., (1998) *FEBS Lett.*, 424:173–176). For a review of the OATP family and organic anoin transport in the liver, see Wolkoff, A. W., (1996) *Semin. Liver Dis.*, 16:121–127.

A third rat OATP isoform that was shown to transport thyroid hormones T3 and T4 was cloned and reported in Abe,T., et al., (1998) *J. Biol. Chem.*, 273:22395–22401.

All references cited herein, whether supra or infra, are hereby incorporated by reference in their entirety.

SUMMARY OF THE INVENTION

The present invention encompasses novel organic anion transport proteins ("OATP") and polynucleotides encoding said OATPs. The OATPs disclosed herein are designated OATP2, OATP-RP2, OATP-RP3, OATP-RP4, OATP-RP5 and OATP-RP1. A polynucleotide sequence of each OATP is disclosed herein, along with the deduced amino acid sequence. The cDNAs encoding the OATPs of the present invention have been deposited with the American Type Culture Collection and given Accession Numbers ATCC 207213 (OATP2), ATCC 207212 (OATP-RP2), ATCC 207209 (OATP-RP3), ATCC 207210 (OATP-RP4), ATCC 207211 (OATP-RP5), and ATCC 207214 (OATP-RP1).

The present inventors sequenced the cDNAs encoding the novel OATPs and determined the primary sequence of the deduced proteins. Disclosed herein are the nucleic acid sequence (SEQ ID NO:1) and amino acid sequence (SEQ ID NO:2) of OATP2; the nucleic acid sequence (SEQ ID NO:3) and amino acid sequence (SEQ ID NO:4) of OATP-RP2; the nucleic acid sequence (SEQ ID NO:5) and amino acid sequence (SEQ ID NO:6) of OATP-RP3; the nucleic acid sequence (SEQ ID NO:7) and amino acid sequence (SEQ ID NO:8) of OATP-RP4; the nucleic acid sequence (SEQ ID NO:9) and amino acid sequence (SEQ ID NO:10) of OATP-RP5; and the nucleic acid sequence (SEQ ID NO:11) and amino acid sequence (SEQ ID NO:12) of OATP-RP1.

The OATPs of the present invention can be produced by: (1) inserting the cDNA of a disclosed OATP into an appropriate expression vector; (2) transfecting the expression vector into an appropriate transfection host(s); (3) growing the transfected host(s) in appropriate culture media; and (4) assaying the transport activity in the transfected cells.

The present invention therefore provides a purified and isolated nucleic acid molecule, preferably a DNA molecule, having a sequence which codes for an OATP, or an oligonucleotide fragment of the nucleic acid molecule which is unique to an OATP of the invention. In a preferred embodiment of the invention, the purified and isolated nucleic acid molecule has the sequence as shown in SEQ ID NO:1 (OATP2). In another preferred embodiment, the purified and isolated nucleic acid molecule has the sequence as shown in SEQ ID NO:3 (OATP-RP2). In still another preferred embodiment the purified and isolated nucleic acid molecule has the sequence as shown in SEQ ID NO:5 (OATP-RP3).

In still another preferred embodiment of the present invention the purified and isolated nucleic acid molecule has the nucleotide sequence as shown in SEQ ID NO:7 (OATP-RP4). In still another preferred embodiment the purified and isolated nucleic acid molecule has the sequence as shown in SEQ ID NO:9 (OATP-RP5). In still another preferred embodiment of the present invention the purified and isolated nucleic acid molecule has the nucleotide sequence as shown in SEQ ID NO:11 (OATP-RP1).

The invention also contemplates a double stranded nucleic acid molecule comprising a nucleic acid molecule of the invention or an oligonucleotide fragment thereof hydrogen bonded to a complementary nucleotide base sequence.

The terms "isolated and purified nucleic acid", "isolated and purified polynucleotide", "substantially pure nucleic acid", and "substantially pure polynucleotide", e.g., substantially pure DNA, refer to a nucleic acid molecule which is one or both of the following: (1) not immediately contiguous with either one or both of the sequences, e.g., coding sequences, with which it is immediately contiguous (i.e., one at the 5' end and one at the 3 end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure or isolated and purified DNA also includes a recombinant DNA which is part of a hybrid gene encoding additional OATP sequence.

The present invention provides in one embodiment: (a) an isolated and purified nucleic acid molecule comprising a sequence encoding all or a portion of a protein having the amino acid sequence as shown in SEQ ID NO:2 (OATP2); (b) nucleic acid sequences complementary to (a); (c) nucleic acid sequences which exhibit at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The degree of homology (percent sequence identity) between two sequences may be determined, for example, by comparing the two sequences using computer programs commonly employed for this purpose. One suitable program is the GAP computer program described by Devereux et al., (1984) Nucl. Acids Res. 12:387. The GAP program utilizes the alignment method of Needleman and Wunsch (1970) J. Mol. Biol. 48:433, as revised by Smith and Waterman (1981) Adv. Appl. Math. 2:482. Briefly, the GAP program defines percent identity as the number of aligned symbols (i.e., nucleotides or amino acids) which are identical, divided by the total number of symbols in the shorter of the two sequences.

As used herein the term "stringent conditions" encompasses conditions known in the art under which a nucleotide sequence will hybridize to: (a) an isolated and purified nucleic acid molecule comprising a sequence encoding a protein having the amino acid sequence as shown herein, or to (b) a nucleic acid sequence complementary to (a). Screening polynucleotides under stringent conditions may be carried out according to the method described in Nature, 313:402–404 (1985). Polynucleotide sequences capable of hybridizing under stringent conditions with the polynucleotides of the present invention may be, for example, allelic variants of the disclosed DNA sequences, or may be derived from other sources. General techniques of nucleic acid hybridization are disclosed by Sambrook et al., "Molecular Cloning: A Laboratory Manual", 2nd Ed., Cold Spring Harbor Laboratory, Cold Spring Harbor, N.Y. (1984); and by Haymes et al., "Nucleic Acid Hybridization: A Practical Approach", IRL Press, Washington, D.C. (1985), which references are incorporated herein by reference.

The present invention provides in another embodiment: (a) an isolated and purified nucleic acid molecule comprising a sequence encoding all or a portion of a protein having the amino acid sequence as shown in SEQ ID NO:4 (OATP-RP2); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:6 (OATP-RP3); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:8 (OATP-RP4); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:10 (OATP-RP5); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:12 (OATP-RP1); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention also provides: (a) a purified and isolated nucleic acid molecule comprising a sequence as shown in SEQ ID NO:1 (OATP2); (b) nucleic lo acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:3 (OATP-RP2); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:5 (OATP-RP3); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:7 (OATP-RP4); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:9 (OATP-RP5); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:11 (OATP-RP1); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention additionally covers polynucleotides and amino acid sequences of the present invention having one or more structural mutations including replacement, deletion or insertion mutations. For example, a signal peptide may be deleted, or conservative amino acid substitutions may be made to generate a protein that is still biologically competent or active.

The invention further contemplates a recombinant molecule comprising a nucleic acid molecule of the present invention or an oligonucleotide fragment thereof and an expression control sequence operatively linked to the nucleic acid molecule or oligonucleotide fragment. A transformant host cell including a recombinant molecule of the invention is also provided.

In another aspect, the invention features a cell or purified preparation of cells which include a novel gene encoding an OATP of the present invention, or which otherwise misexpresses a gene encoding an OATP of the present invention. The cell preparation can consist of human or non-human cells, e.g., rodent cells, e.g., mouse or rat cells, rabbit cells, non-human primate cells, or pig cells. In preferred embodiments, the cell or cells include an OATP transgene, e.g., a heterologous form of an OATP gene, e.g., a gene derived from humans (in the case of a non-human cell). The OATP transgene can be misexpressed, e.g., overexpressed or underexpressed. In other preferred embodiments, the cell or cells include a gene which misexpresses an endogenous OATP gene, e.g., a gene that expression of which is disrupted, e.g., a knockout. Such cells can serve as a model for studying disorders which are related to mutated or misexpressed OATP alleles for use in drug screening.

Still further, the invention provides plasmids which comprise the nucleic acid molecules of the invention. Also encompassed within the invention are vectors comprising the nucleic acid sequences disclosed herein, as well as host cells comprising said vectors.

The present invention also includes a novel OATP of the present invention, or an active part thereof. A biologically competent or active form of the protein or part thereof is also referred to herein as an "active OATP or part thereof".

The invention further contemplates antibodies having specificity against an epitope of an OATP of the present invention or part of the protein. These antibodies may be polyclonal or monoclonal. The antibodies may be labeled with a detectable substance and they may be used, for example, to detect a novel OATP of the invention in tissue and cells. Additionally, the antibodies of the present invention, or portions thereof, may be used to make targeted antibodies that destroy OATP expressing cells (e.g., antibody-toxin fusion proteins, or radiolabelled antibodies).

The invention also permits the construction of nucleotide probes which encode part or all of a novel OATP protein of the invention or a part of the protein. Thus, the invention also relates to a probe comprising a nucleotide sequence coding for a protein, which displays the properties of a novel OATP of the invention or a peptide unique to the protein. The probe may be labeled, for example, with a detectable (e.g., radioactive) substance and it may be used to select from a mixture of nucleotide sequences a nucleotide sequence coding for a protein which displays the properties of a novel OATP of the invention.

The present invention also provides a transgenic non-human animal (e.g., a rodent, e.g., a mouse or a rat, a rabbit or a pig) or embryo all of whose germ cells and somatic cells contain a recombinant molecule of the invention, preferably a recombinant molecule comprising a nucleic acid molecule of the present invention encoding an OATP of the invention or part thereof. The recombinant molecule may comprise a nucleic acid sequence encoding an OATP of the present invention with a structural mutation, or may comprise a nucleic acid sequence encoding an OATP of the invention or part thereof and one or more regulatory elements which differ from the regulatory elements that drive expression of the native protein. In another preferred embodiment, the animal has an OATP gene which is misexpressed or not expressed, e.g., a knockout. Such transgenic animals can serve as a model for studying disorders that are related to mutated or misexpressed OATPs of the present invention.

The invention still further provides a method for identifying a substance which is capable of binding a novel OATP of the invention, comprising reacting a novel OATP of the invention or part of the protein under conditions which permit the formation of a complex between the substance and a novel OATP protein or part of the protein, and assaying for substance-OATP complexes, for free substance, for non-complexed OATP, or for activation of an OATP.

An embodiment of the invention provides a method for identifying substrates which are capable of binding to a novel OATP protein of the invention, isoforms thereof, or part of the protein, said method comprising reacting a novel OATP protein of the invention, isoforms thereof, or part of the protein, with at least one substrate which potentially is capable of binding to the protein, isoform, or part of the protein, under conditions which permit the formation of substrate-transporter protein complexes, and assaying for substrate-transporter protein complexes, for free substrate, for non-complexed OATP protein, or for activation of an OATP. In a preferred embodiment of the method, substrates are identified which are capable of binding to and being transported by a novel OATP protein of the invention, isoforms thereof, or part of the protein.

The invention also provides methods for screening potentially useful pharmacological agonists or antagonists of the OATPs of the present invention. The method comprises testing potential agents by adding the agent to be tested to a cell expressing a novel OATP of the present invention in the presence of a compound known to be transported by an OATP of the invention, and measuring the augmentation or inhibition of transport of the known compound.

An OATP of the present invention is also useful to identify compounds that may be transported into an organ, e.g., the liver. Compounds that are found to be actively transported into the liver are useful as carriers for other therapeutics targeting the liver.

Also included within the scope of the present invention is a composition which includes an OATP of the present invention, a fragment thereof (or a nucleic acid encoding said OATP or fragment thereof) and one or more additional components, e.g., a carrier, diluent or solvent. The additional component can be one that renders the composition useful for in vitro, in vivo, pharmaceutical or veterinary use.

Encompassed within the present invention are agonists and antagonists of an OATP of the present invention. Pharmacological agonists or antagonists are useful to increase or decrease the flow of compounds transported by an OATP of the present invention. Said agonists and/or antagonists of the present invention are preferably administered with an acceptable carrier, diluent or solvent.

In another aspect, the present invention relates to a method of treating a mammal, e.g., a human, at risk for a disorder, e.g., a disorder characterized by aberrant or unwanted level or biological activity of an OATP of the present invention. Additionally, encompassed within the invention is a method of treating a mammal, e.g., a human, at risk for disorders of the liver. Since OATP2 is expressed exclusively in the liver, compounds that are optimized for OATP2 are useful to target hepatic delivery. These compounds in themselves may be useful therapeutics, or may be useful to chaperone other therapeutic compounds to the liver. In addition, blocking OATP2-compound interactions could provide benefit by decreasing its first-pass extraction by the liver and, thus, increasing plasma concentrations and prolonging the systemic half-life of a drug.

Also within the scope of the present invention are fusion proteins comprising all or a portion of an OATP of the present invention.

The primary object of the present invention is the identification of new human OATPs, as identified by the nucleic acid and amino acid sequences disclosed herein. Additional objects of the invention are the methods of using the cDNA, the OATP proteins, monoclonal antibodies specific for the novel OATPs, fusion proteins comprising a portion of the OATP protein of the present invention, and agonists and/or antagonists of the novel OATPs as described above.

BRIEF DESCRIPTION OF THE FIGURES

FIG. 3 shows a sequence alignment of OATP family members. The protein sequences of human OATP2 (SEQ ID NO:2), OATP-RP1 (SEQ ID NO:12), OATP-RP2 (SEQ ID NO:4), OATP-RP3 (SEQ ID NO:6), OATP-RP4 (SEQ ID NO:8), and OATP-RP5 (SEQ ID NO:10) are aligned with the following other known OATP family members: roatp2 (SEQ ID NO:23); roatp3 (SEQ ID NO:24); rOAT-K1 (SEQ ID NO:25); roatp1 (SEQ ID NO:26); hOATP (SEQ ID NO:27); and hPGT (SEQ ID NO:28). Also shown is a consensus sequence in bold (SEQ ID NO:29). A concensus is indicated if at least 6 out of the 12 sequences are identical at a given position. A residue is capitalized if it agrees with the concensus.

DETAILED DESCRIPTION OF THE INVENTION

Figure 1:
FIG. 1 is a Northern blot showing the mRNA tissue distribution of OATP2, OATP-RP1, OATP-RP2, OATP-RP4, and OATP-RP5. The tissues corresponding to the abbreviations above the lanes are indicated below.
Figure 1:
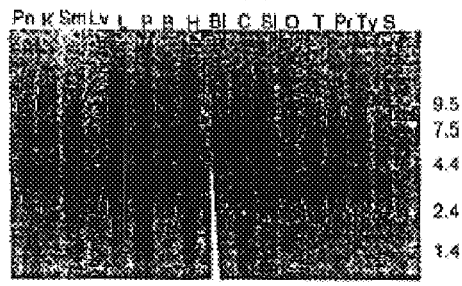
Figure 1:
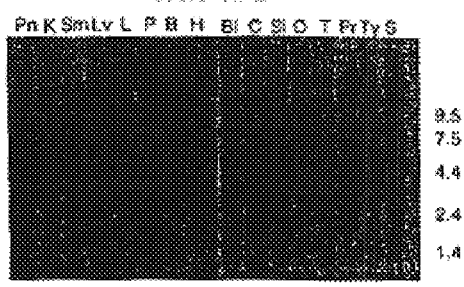
Figure 1:
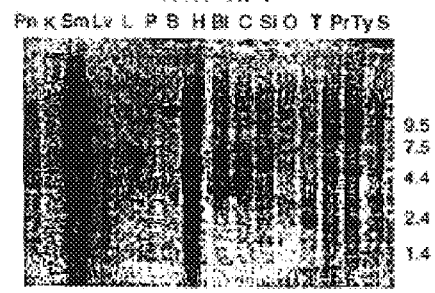
Figure 1:
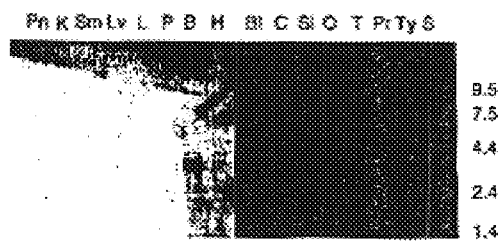

The following definitions apply to the terms used throughout this specification, unless otherwise defined in specific instances:

"cloning"—isolation of a particular gene from genetic material, for example a genome, genomic library, or cDNA library into a plasmid or other vector;

"coding region"—the region of a nucleic acid sequence that codes for an active protein;

"OATP"—organic anion transport protein;

"stringent conditions"—(as used concerning nucleic acid hybridization)—Southern blotting washed in 0.1×SSC and 0.1% SDS at a temperature of at least about 65° C. See Maniatis et al., Molecular Cloning: A Laboratory Manual, Cold Spring Harbor Laboratory, Cold Spring Harbor, N.Y. (1982); one skilled in the relevant art would recognize that less stringent conditions (e.g., 1× or 2×SSC, 0.1% SDS) may be employed in using the novel sequences disclosed herein to identify nucleic acid sequences encoding novel OATPs.

"Northern blotting"—a method of identifying particular RNA fragments by hybridization with a complementary nucleic acid, typically a cDNA or an oligonucleotide;

"open reading frame" or "ORF"—a DNA sequence containing a series of nucleotide triplets coding for amino acids and lacking any termination codes;

"plasmid"—cytoplasmic, autonomously replicating DNA elements found in microorganisms;

"promoter"—a region on DNA at which RNA polymerase binds and initiates transcription; and "Southern blotting"—a method of identifying particular DNA fragments by hybridization with a complementary nucleic acid, typically a cDNA or an oligonucleotide;

"transport"—the movement of a substance across a biological membrane as determined by measuring the redistribution of such a substance across the membrane upon exposure to a transporter.

For definitions of other terms in this specification, see F. Sherman et al., *Laboratory Course Manual for Methods in Yeast Genetics*, Cold Spring Harbor Laboratory, Cold Spring Harbor, N.Y. (1987) and Lewin, B., *Genes IV*, Oxford University Press, Oxford (1990). For the definitions of abbreviations, see *Aldrichimica Acta*, Vol. 17, No. 1 (1984).

Use and Utility

Figure 3E:
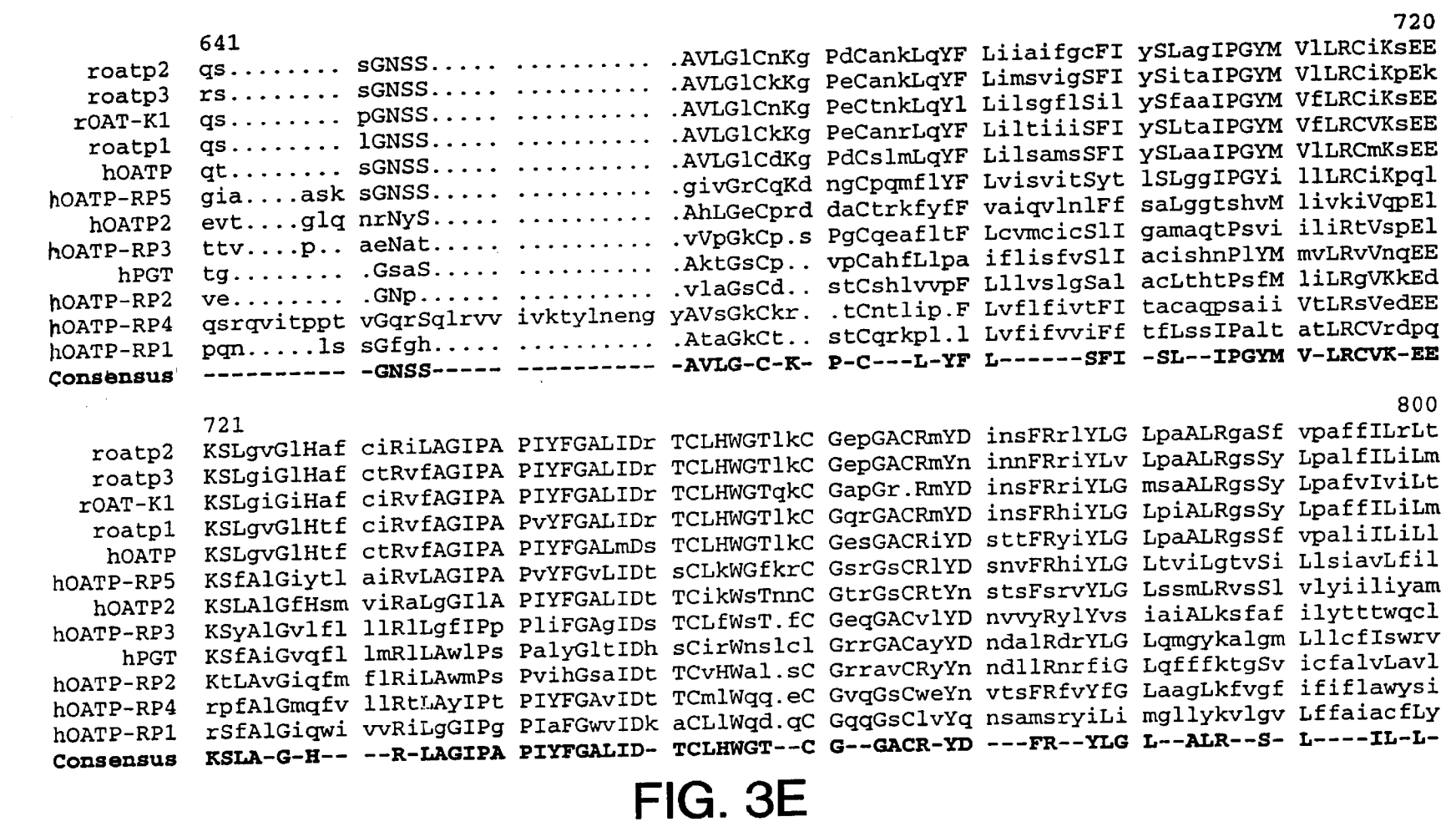

The amino acid sequences of the novel organic anion transport proteins of the present invention are aligned with known transporters of this family in FIG. 3. The degree of sequence homology between the sequences of the present invention and known organic anion transporters indicates that the proteins of the present invention are organic anion transporters.

It is believed by those skilled in the art that OATP proteins may be involved in the transport of compounds into the liver. Persons of ordinary skill in the art can use the OATP proteins of the present invention to assay for agents that may increase or decrease the rate of transport of compounds into the liver, or for compounds that are transported by the OATPs of the present invention that are useful as carriers for other compounds that are desired to be carried to a specific organ (e.g., the liver).

Therefore, agents that increase or decrease the rate of substrate transport by the OATPs of the present invention, or agents identified as carriers, are useful in the treatment of liver disease.

Because some of the OATPs of the present invention are organ specific/selective (e.g., OATP2—liver; OATP-RP4—heart and skeletal muscle, and OATP-RP5—brain and testis), compound specificity is built into any specific substrate of these OATPs and into molecular carriers transported by these OATPs. An agent transported by the above OATPs of the present invention would thus be delivered to the tissues in which they are expressed and not to tissues lacking the above OATPs, thereby achieving tissue specific targeting.

The OATP nucleic acids of the present invention, or antisense nucleic acids, may be useful therapeutic or diagnostic agents. For such gene therapy, the nucleic acids may be incorporated into vectors and/or formulated as described below and in further detail in the art.

The present invention also provides a basis for diagnostic genetic screens for predicting response to drugs. At least one of the transporters disclosed and claimed herein is a transporter of a known drug (i.e., OATP2 transports pravastatin into hepatocytes). Other transporters disclosed herein may similarly transport additional drugs into tissues. Persons skilled in the art can: (1) screen the transporter genes for allelic variants (genotypes) in the general population by various sequencing methods; and (2) determine the association of these transporter genotypes in patients with response to the transported drug in clinical trials. Particular allelic variants may be more or less effective in transporting a drug, which would be related to drug efficacy. Thus, genotyping of the claimed transporters could form the basis of a clinical diagnostic test to predict a patient's response to drug therapy.

Persons skilled in the art can use the polypeptides and nucleic acids of this invention to prepare vectors, cells or cell lines, and antibodies. All of these are useful in assays for identification of OATP positive and negative modulators (i.e., agonists and/or antagonists) and OATP carriers. The term "positive modulator" as used herein refers to an agent or compound that increases the rate or amount of transport of a compound into an organ, e.g., the liver, or an agent or compound that decreases the rate or amount of transport of a compound into an organ. The term "negative modulator" refers to a compound that is joined to a second compound to prevent the second compounds transport into or out of cells. The term "carrier" as used herein refers to an agent or compound that is transported by an OATP of the present invention and that is capable of being joined to or associated with another compound to chaperone that other compound into an organ, e.g., the liver. A carrier includes an agent that is used to transport a compound into an organ that is otherwise not transported into said organ, and includes an agent that increases the transport of a compound into an organ that is capable of being transported by an OATP.

One can administer OATP modulators and carriers to various mammalian species, such as monkeys, dogs, cats, mice, rats, humans, etc. By known methods, persons skilled in the pharmaceutical art can incorporate OATP modulators and carriers in a conventional systemic dosage form, such as a tablet, capsule, elixir or injectable formulation. The above dosage forms will also include any necessary physiologically acceptable carrier material, excipient, lubricant, buffer, antibacterial, bulking agent (such as mannitol), anti-oxidants (ascorbic acid or sodium bisulfite) or the like.

Process of Preparation

In General

This specification describes the cloning and functional expression of full-length human cDNA clones of OATPs, preferably the nucleic acid sequence of OATP2 (SEQ ID NO:1), the amino acid sequence of OATP2 (SEQ ID NO:2), the nucleic acid sequence of OATP-RP2 (SEQ ID NO:3), the amino acid sequence of OATP-RP2 (SEQ ID NO:4), the nucleic acid sequence of OATP-RP3 (SEQ ID NO:5), the amino acid sequence of OATP-RP3 (SEQ ID NO:6), the nucleic acid sequence of OATP-RP4 (SEQ ID NO:7), the amino acid sequence of OATP-RP4 (SEQ ID NO:8), the nucleic acid sequence of OATP-RP5 (SEQ ID NO:9), the amino acid sequence of OATP-RP5 (SEQ ID NO:10), the nucleic acid sequence of OATP-RP1 (SEQ ID NO:11), and the amino acid sequence of OATP-RP1 (SEQ ID NO:12).

DNA clones comprising nucleotide sequences encoding the OATPs described above were deposited with the American Type Culture Collection ("ATCC") (10801 University Blvd., Manassas, Va. 20110–2209) on April 20, 1999, and given the following ATCC Accession Numbers: 207209 (OATP-RP3), 207210 (OATP-RP4), 207211 (OATP-RP5), 207212 (OATP-RP2), 207213 (OATP2), and 207214 (OATP-RP1). The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the of the polypeptides encoded thereby, are incorporated herein by reference and are controlling in the event of any conflict with any description of sequences herein. A license may be required to make, use or sell the deposited materials, and no such license is hereby granted.

Nucleic Acids

With the disclosed OATP gene sequences in hand, one skilled in the art can obtain OATP nucleic acids of this invention by known methods. Such methods include: (1) Southern and Northern blotting; (2) Western immunoblotting; (3) chemical synthesis; (4) synthesis by polymerase chain reaction (PCR) from primers; (5) expression cloning; and (6) subtractive cDNA cloning.

Preferred nucleic acid sequences of the present invention include the following (preferably the coding sequences as shown below):

```
OATP2 (SEQ ID NOS:1 and 2):
CGGACGCGTG GGCGGACGCG TGGGTCGCCC ACGCGTCCGA CTTGTTGCAG        50

TTGCTGTAGG ATTCTAAATC CAGGTGATTG TTTCAAACTG AGCATCAACA       100

ACAAAAACAT TTGTATGATA TCTATATTTC AATC ATG GAC CAA AAT CAA    149
                                      M   D   Q   N   Q

CAT TTG AAT AAA ACA GCA GAG GCA CAA CCT TCA GAG AAT AAG      191
 H   L   N   K   T   A   E   A   Q   P   S   E   N   K

AAA ACA AGA TAC TGC AAT GGA TTG AAG ATG TTC TTG GCA GCT      233
 K   T   R   Y   C   N   G   L   K   M   F   L   A   A

CTG TCA CTC AGC TTT ATT GCT AAG ACA CTA GGT GCA ATT ATT      275
 L   S   L   S   F   I   A   K   T   L   G   A   I   I

ATG AAA AGT TCC ATC ATT CAT ATA GAA CGG AGA TTT GAG ATA      317
 M   K   S   S   I   I   H   I   E   R   R   F   E   I

TCC TCT TCT CTT GTT GGT TTT ATT GAC GGA AGC TTT GAA ATT      359
 S   S   S   L   V   G   F   I   D   G   S   F   E   I

GGA AAT TTG CTT GTG ATT GTA TTT GTG AGT TAC TTT GGA TCC      401
 G   N   L   L   V   I   V   F   V   S   Y   F   G   S

AAA CTA CAT AGA CCA AAG TTA ATT GGA ATC GGT TGT TTC ATT      443
 K   L   H   R   P   K   L   I   G   I   G   C   F   I

ATG GGA ATT GGA GGT GTT TTG ACT GCT TTG CCA CAT TTC TTC      485
 M   G   I   G   G   V   L   T   A   L   P   H   F   F

ATG GGA TAT TAC AGG TAT TCT AAA GAA ACT AAT ATC GAT TCA      527
 M   G   Y   Y   R   Y   S   K   E   T   N   I   D   S

TCA GAA AAT TCA ACA TCG ACC TTA TCC ACT TGT TTA ATT AAT      569
 S   E   N   S   T   S   T   L   S   T   C   L   I   N

CAA ATT TTA TCA CTC AAT AGA GCA TCA CCT GAG ATA GTG GGA      611
 Q   I   L   S   L   N   R   A   S   P   E   I   V   G

AAA GGT TGT TTA AAG GAA TCT GGG TCA TAC ATG TGG ATA TAT      653
 K   G   C   L   K   E   S   G   S   Y   M   W   I   Y

GTG TTC ATG GGT AAT ATG CTT CGT GGA ATA GGG GAG ACT CCC      695
 V   F   M   G   N   M   L   R   G   I   G   E   T   P

ATA GTA CCA TTG GGG CTT TCT TAC ATT GAT GAT TTC GCT AAA      737
 I   V   P   L   G   L   S   Y   I   D   D   F   A   K

GAA GGA CAT TCT TCT TTG TAT TTA GGT ATA TTG AAT GCA ATA      779
 E   G   H   S   S   L   Y   L   G   I   L   N   A   I

GCA ATG ATT GGT CCA ATC ATT GGC TTT ACC CTG GGA TCT CTG      821
 A   M   I   G   P   I   I   G   F   T   L   G   S   L

TTT TCT AAA ATG TAC GTG GAT ATT GGA TAT GTA GAT CTA AGC      863
 F   S   K   M   Y   V   D   I   G   Y   V   D   L   S

ACT ATC AGG ATA ACT CCT ACT GAT TCT CGA TGG GTT GGA GCT      905
 T   I   R   I   T   P   T   D   S   R   W   V   G   A

TGG TGG CTT AAT TTC CTT GTG TCT GGA CTA TTC TCC ATT ATT      947
 W   W   L   N   F   L   V   S   G   L   F   S   I   I

TCT TCC ATA CCA TTC TTT TTC TTG CCC CAA ACT CCA AAT AAA      989
 S   S   I   P   F   F   F   L   P   Q   T   P   N   K

CCA CAA AAA GAA AGA AAA GCT TCA CTG TCT TTG CAT GTG CTG     1031
 P   Q   K   E   R   K   A   S   L   S   L   H   V   L
```

-continued

```
GAA ACA AAT GAT GAA AAG GAT CAA ACA GCT AAT TTG ACC AAT    1073
 E   T   N   D   E   K   D   Q   T   A   N   L   T   N

CAA GGA AAA AAT ATT ACC AAA AAT GTG ACT GGT TTT TTC CAG    1115
 Q   G   K   N   I   T   K   N   V   T   G   F   F   Q

TCT TTT AAA AGC ATC CTT ACT AAT CCC CTG TAT GTT ATG TTT    1157
 S   F   K   S   I   L   T   N   P   L   Y   V   M   F

GTG CTT TTG ACG TTG TTA CAA GTA AGC AGC TAT ATT GGT GCT    1199
 V   L   L   T   L   L   Q   V   S   S   Y   I   G   A

TTT ACT TAT GTC TTC AAA TAC GTA GAG CAA CAG TAT GGT CAG    1241
 F   T   Y   V   F   K   Y   V   E   Q   Q   Y   G   Q

CCT TCA TCT AAG GCT AAC ATC TTA TTG GGA GTC ATA ACC ATA    1283
 P   S   S   K   A   N   I   L   L   G   V   I   T   I

CCT ATT TTT GCA AGT GGA ATG TTT TTA GGA GGA TAT ATC ATT    1325
 P   I   F   A   S   G   M   F   L   G   G   Y   I   I

AAA AAA TTC AAA CTG AAC ACC GTT GGA ATT GCC AAA TTC TCA    1367
 K   K   F   K   L   N   T   V   G   I   A   K   F   S

TGT TTT ACT GCT GTG ATG TCA TTG TCC TTT TAC CTA TTA TAT    1409
 C   F   T   A   V   M   S   L   S   F   Y   L   L   Y

TTT TTC ATA CTC TGT GAA AAC AAA TCA GTT GCC GGA CTA ACC    1451
 F   F   I   L   C   E   N   K   S   V   A   G   L   T

ATG ACC TAT GAT GGA AAT AAT CCA GTG ACA TCT CAT AGA GAT    1493
 M   T   Y   D   G   N   N   P   V   T   S   H   R   D

GTA CCA CTT TCT TAT TGC AAC TCA GAC TGC AAT TGT GAT GAA    1535
 V   P   L   S   Y   C   N   S   D   C   N   C   D   E

AGT CAA TGG GAA CCA GTC TGT GGA AAC AAT GGA ATA ACT TAC    1577
 S   Q   W   E   P   V   C   G   N   N   G   I   T   Y

ATC TCA CCC TGT CTA GCA GGT TGC AAA TCT TCA AGT GGC AAT    1619
 I   S   P   C   L   A   G   C   K   S   S   S   G   N

AAA AAG CCT ATA GTG TTT TAC AAC TGC AGT TGT TTG GAA GTA    1661
 K   K   P   I   V   F   Y   N   C   S   C   L   E   V

ACT GGT CTC CAG AAC AGA AAT TAC TCA GCC CAT TTG GGT GAA    1703
 T   G   L   Q   N   R   N   Y   S   A   H   L   G   E

TGC CCA AGA GAT GAT GCT TGT ACA AGG AAA TTT TAC TTT TTT    1745
 C   P   R   D   D   A   C   T   R   K   F   Y   F   F

GTT GCA ATA CAA GTC TTG AAT TTA TTT TTC TCT GCA CTT GGA    1787
 V   A   I   Q   V   L   N   L   F   F   S   A   L   G

GGC ACC TCA CAT GTC ATG CTG ATT GTT AAA ATT GTT CAA CCT    1829
 G   T   S   H   V   M   L   I   V   K   I   V   Q   P

GAA TTG AAA TCA CTT GCA CTG GGT TTC CAC TCA ATG GTT ATA    1871
 E   L   K   S   L   A   L   G   F   H   S   M   V   I

CGA GCA CTA GGA GGA ATT CTA GCT CCA ATA TAT TTT GGG GCT    1913
 R   A   L   G   G   I   L   A   P   I   Y   F   G   A

CTG ATT GAT ACA ACG TGT ATA AAG TGG TCC ACC AAC AAC TGT    1955
 L   I   D   T   T   C   I   K   W   S   T   N   N   C

GGC ACA CGT GGG TCA TGT AGG ACA TAT AAT TCC ACA TCA TTT    1997
 G   T   R   G   S   C   R   T   Y   N   S   T   S   F

TCA AGG GTC TAC TTG GGC TTG TCT TCA ATG TTA AGA GTC TCA    2039
 S   R   V   Y   L   G   L   S   S   M   L   R   V   S

TCA CTT GTT TTA TAT ATT ATA TTA ATT TAT GCC ATG AAG AAA    2081
 S   L   V   L   Y   I   I   L   I   Y   A   M   K   K

AAA TAT CAA GAG AAA GAT ATC AAT GCA TCA GAA AAT GGA AGT    2123
 K   Y   Q   E   K   D   I   N   A   S   E   N   G   S

GTC ATG GAT GAA GCA AAC TTA GAA TCC TTA AAT AAA AAT AAA    2165
 V   M   D   E   A   N   L   E   S   L   N   K   N   K
```

```
CAT TTT GTC CCT TCT GCT GGG GCA GAT AGT GAA ACA CAT TGT      2207
 H   F   V   P   S   A   G   A   D   S   E   T   H   C

TAA GGGGAGAAAA AAAGCCACTT CTGCTTCTGT GTTTCCAAAC AGCATTGCAT   2260
 *

TGATTCAGTA AGATGTTATT TTTGAGGAGT TCCTGGTCCT TTCACTAAGA       2310

ATTTCCACAT CTTTTATGGT GGAAGTATAA ATAAGCCTAT GAACTTATAA       2360

TAAAACAAAC TGTAGGTAGA AAAAATGAGA GTACTCATTG TTACATTATA       2410

GCTACATATT TGTGGTTAAG GTTAGACTAT ATGATCCATA CAAATTAAAG       2460

TGAGAGACAT GGTTACTGTG TAATAAAAGA AAAAATACTT GTTCAGGTAA       2510

TTCTAATTCT TAATAAAACA AATGAGTATC ATACAGGTAG AGGTTAAAAA       2560

GGAGGAGCTA GATTCATATC CTAAGTAAAG AGAAATGCCT AGTGTCTATT       2610

TTATTAAACA AACAAACACA GAGTTTGAAC TATAATACTA AGGCCTGAAG       2660

TCTAGCTTGG ATATATGCTA CAATAATATC TGTTACTCAC ATAAAATTAT       2710

ATATTTCACA GACTTTATCA ATGTATAATT AACAATTATC TTGTTTAAGT       2760

AAATTTAGAA TACATTTAAG TATTGTGGAA GAAATAAAGA CATTCCAATA       2810

TTTGCAAAAA AAAAAAAAA                                         2830

OATP-RP2 (SEQ ID NOS:3 and 4):
CCCGGGTCGA CCCACGCGTC CGGGATAAAG TACTCCCAGG AAGGCTTTGA         50

GCCTTGGCAG AAGAGGCTGG GATTGAAGCT TCAGGGAGAG CCAGAGGTGA        100

GGCTGGAGTG GGAGATCACC TGAGGCAGGG CCAGCGGGTG AGGTACCCCA        150

GGTACCAGAC AAGGAAACCA AAGCCACA ATG GGC ACA GAA AAC ACA CCT    199
                                M   G   T   E   N   T   P

GGA GGC AAA GCC AGC CCA GAC CCT CAG GAC GTG CGG CCA AGT       241
 G   G   K   A   S   P   D   P   Q   D   V   R   P   S

GTG TTC CAT AAC ATC AAG CTG TTC GTT CTG TGC CAC AGC CTG       283
 V   F   H   N   I   K   L   F   V   L   C   H   S   L

CTG CAG CTG GCG CAG CTC ATG ATC TCC GGC TAC CTA AAG AGC       325
 L   Q   L   A   Q   L   M   I   S   G   Y   L   K   S

TCC ATC TCC ACA GTG GAG AAG CGC TTC GGC CTC TCC AGC CAG       367
 S   I   S   T   V   E   K   R   F   G   L   S   S   Q

ACG TCG GGC CTG CTG GCC TCC TTC AAC GAG GTG GGG AAC ACA       409
 T   S   G   L   L   A   S   F   N   E   V   G   N   T

GCC TTG ATT GTG TTT GTG AGC TAT TTT GGC AGC CGG GTG CAC       451
 A   L   I   V   F   V   S   Y   F   G   S   R   V   H

CGA CCC CGA ATG ATT GGC TAT GGG GCT ATC CTT GTG GCC CTG       493
 R   P   R   M   I   G   Y   G   A   I   L   V   A   L

GCG GGC CTG CTC ATG ACT CTC CCG CAC TTC ATC TCG GAG CCA       535
 A   G   L   L   M   T   L   P   H   F   I   S   E   P

TAC CGC TAC GAC AAC ACC AGC CCT GAG GAT ATG CCA CAG GAC       577
 Y   R   Y   D   N   T   S   P   E   D   M   P   Q   D

TTC AAG GCT TCC CTG TGC CTG CCC ACA ACC TCG GCC CCA GCC       619
 F   K   A   S   L   C   L   P   T   T   S   A   P   A

TCG GCC CCC TCC AAT GGC AAC TGC TCA AGC TAC ACA GAA ACC       661
 S   A   P   S   N   G   N   C   S   S   Y   T   E   T

CAG CAT CTG AGT GTG GTG GGG ATC ATG TTC GTG GCA CAG ACC       703
 Q   H   L   S   V   V   G   I   M   F   V   A   Q   T

CTG CTG GGC GTG GGC GGG GTG CCC ATT CAG CCC TTT GGC ATC       745
 L   L   G   V   G   G   V   P   I   Q   P   F   G   I
```

-continued

| | |
|---|---|
| TCC TAC ATC GTT GAC TTT GCC CAC AAC AGT AAC TCG CCC CTC<br>S   Y   I   V   D   F   A   H   N   S   N   S   P   L | 787 |
| TAC CTC GGG ATC CTG TTT GCA GTG ACC ATG ATG GGG CCA GGC<br>Y   L   G   I   L   F   A   V   T   M   M   G   P   G | 829 |
| CTG GCC TTT GGG CTG GGC AGC CTC ATG CTG CGC CTT TAT GTG<br>L   A   F   G   L   G   S   L   M   L   R   L   Y   V | 871 |
| GAC ATT AAC CAG ATG CCA GAA GGT GGT ATC AGC CTG ACC ATA<br>D   I   N   Q   M   P   E   G   G   I   S   L   T   I | 913 |
| AAG GAC CCC CGA TGG GTG GGT GCC TGG TGG CTG GGT TTC CTC<br>K   D   P   R   W   V   G   A   W   W   L   G   F   L | 955 |
| ATC GCT GCC GGT GCA GTG GCC CTG GCT GCC ATC CCC TAC TTC<br>I   A   A   G   A   V   A   L   A   A   I   P   Y   F | 997 |
| TTC TTC CCC AAG GAA ATG CCC AAG GAA AAA CGT GAG CTT CAG<br>F   F   P   K   E   M   P   K   E   K   R   E   L   Q | 1039 |
| TTT CGG CGA AAG GTC TTA GCA GTC ACA GAC TCA CCT GCC AGG<br>F   R   R   K   V   L   A   V   T   D   S   P   A   R | 1081 |
| AAG GGC AAG GAC TCT CCC TCT AAG CAG AGC CCT GGG GAG TCC<br>K   G   K   D   S   P   S   K   Q   S   P   G   E   S | 1123 |
| ACG AAG AAG CAG GAT GGC CTA GTC CAG ATT GCA CCA AAC CTG<br>T   K   K   Q   D   G   L   V   Q   I   A   P   N   L | 1165 |
| ACT GTG ATC CAG TTC ATT AAA GTC TTC CCC AGG GTG CTG CTG<br>T   V   I   Q   F   I   K   V   F   P   R   V   L   L | 1207 |
| CAG ACC CTA CGC CAC CCC ATC TTC CTG CTG GTG GTC CTG TCC<br>Q   T   L   R   H   P   I   F   L   L   V   V   L   S | 1249 |
| CAG GTA TGC TTG TCA TCC ATG GCT GCG GGC ATG GCC ACC TTC<br>Q   V   C   L   S   S   M   A   A   G   M   A   T   F | 1291 |
| CTG CCC AAG TTC CTG GAG CGC CAG TTT TCC ATC ACA GCC TCC<br>L   P   K   F   L   E   R   Q   F   S   I   T   A   S | 1333 |
| TAC GCC AAC CTG CTC ATC GGC TGC CTC TCC TTC CCT TCG GTC<br>Y   A   N   L   L   I   G   C   L   S   F   P   S   V | 1375 |
| ATC GTG GGC ATC GTG GTG GGT GGC GTC CTG GTC AAG CGG CTC<br>I   V   G   I   V   V   G   G   V   L   V   K   R   L | 1417 |
| CAC CTG GGC CCT GTG GGA TGC GGT GCC CTT TGC CTG CTG GGG<br>H   L   G   P   V   G   C   G   A   L   C   L   L   G | 1459 |
| ATG CTG CTG TGC CTC TTC TTC AGC CTG CCG CTC TTC TTT ATC<br>M   L   L   C   L   F   F   S   L   P   L   F   F   I | 1501 |
| GGC TGC TCC AGC CAC CAG ATT GCG GGC ATC ACA CAC CAG ACC<br>G   C   S   S   H   Q   I   A   G   I   T   H   Q   T | 1543 |
| AGT GCC CAC CCT GGG CTG GAG CTG TCT CCA AGC TGC ATG GAG<br>S   A   H   P   G   L   E   L   S   P   S   C   M   E | 1585 |
| GCC TGC TCC TGC CCA TTG GAC GGC TTT AAC CCT GTC TGC GAC<br>A   C   S   C   P   L   D   G   F   N   P   V   C   D | 1627 |
| CCC AGC ACT CGT GTG GAA TAC ATC ACA CCC TGC CAC GCA GGC<br>P   S   T   R   V   E   Y   I   T   P   C   H   A   G | 1669 |
| TGC TCA AGC TGG GTG GTC CAG GAT GCT CTG GAC AAC AGC CAG<br>C   S   S   W   V   V   Q   D   A   L   D   N   S   Q | 1711 |
| GTT TTC TAC ACC AAC TGC AGC TGC GTG GTG GAG GGC AAC CCC<br>V   F   Y   T   N   C   S   C   V   V   E   G   N   P | 1753 |
| GTG CTG GCA GGA TCC TGC GAC TCA ACG TGC AGC CAT CTG GTG<br>V   L   A   G   S   C   D   S   T   C   S   H   L   V | 1795 |
| GTG CCC TTC CTG CTC CTG GTC AGC CTG GGC TCG GCC CTG GCC<br>V   P   F   L   L   L   V   S   L   G   S   A   L   A | 1837 |
| TGT CTC ACC CAC ACA CCC TCC TTC ATG CTC ATC CTA AGA GGA<br>C   L   T   H   T   P   S   F   M   L   I   L   R   G | 1879 |

-continued

```
GTG AAG AAA GAA GAC AAG ACT TTG GCT GTG GGC ATC CAG TTC      1921
 V   K   K   E   D   K   T   L   A   V   G   I   Q   F

ATG TTC CTG AGG ATT TTG GCC TGG ATG CCC AGC CCC GTG ATC      1963
 M   F   L   R   I   L   A   W   M   P   S   P   V   I

CAC GGC AGC GCC ATC GAC ACC ACC TGT GTG CAC TGG GCC CTG      2005
 H   G   S   A   I   D   T   T   C   V   H   W   A   L

AGC TGT GGG CGT CGA GCT GTC TGT CGC TAC TAC AAT AAT GAC      2047
 S   C   G   R   R   A   V   C   R   Y   Y   N   N   D

CTG CTC CGA AAC CGG TTC ATC GGC CTC CAG TTC TTC TTC AAA      2089
 L   L   R   N   R   F   I   G   L   Q   F   F   F   K

ACA GGT TCT GTG ATC TGC TTC GCC TTA GTT TTG GCT GTC CTG      2131
 T   G   S   V   I   C   F   A   L   V   L   A   V   L

AGG CAG CAG GAC AAA GAG GCA AGG ACC AAA GAG AGC AGA TCC      2173
 R   Q   Q   D   K   E   A   R   T   K   E   S   R   S

AGC CCT GCC GTA GAG CAG CAA TTG CTA GTG TCG GGC CCA GGG      2215
 S   P   A   V   E   Q   Q   L   L   V   S   G   P   G

AAG AAG CCA GAG GAT TCC CGA GTG TGA GCTGTCTTGG GGCCCCACCT    2262
 K   K   P   E   D   S   R   V   *

GGCCAAGAGT AGCAGCCACA GCAGTACCTC CTCTGAGTCC TTTGCCCAAG       2312

ATTGGGTGTC AAGAGCCCTG TGTTCCATTC TGGCTCCTCC ACTAAATTGC       2362

TGTGTGACTT CAGGCAAAAA AAAAAAAAAA AAAAAAAAAA AAAAAAAAAA       2412

AAAAAAAAAA AAAAAAAAAA AAAAAAAAA                              2442

OATP-RP3 (SEQ ID NOS:5 and 6):
                                                CC CACGCGTCCG      12

GCGAGGAGCT GTGCCTTCCA CCTCTCCAGC CCCGGCAGGA CGGGGGCGGC               62

CGCCGCGAAC CCGGGGCGGG GACAGCACGC AGCCTCGAGG CGCGCACCCC              112

CGCCCGGCAG CGGCCCCGAC ACCCGGGGCG AGCGGGAAAG CGGCAGCGGC              162

GGCGGCGGCG GCGGCGGCGG GGGAAGG ATG CAG GGG AAG AAG CCG GGC           210
                                 M   Q   G   K   K   P   G

GGT TCG TCG GGC GGC GGC CGG AGC GGC GAG CTG CAG GGG GAC             252
 G   S   S   G   G   G   R   S   G   E   L   Q   G   D

GAG GCG CAG AGG AAC AAG AAA AAG AAA AAG AAG GTG TCC TGC             294
 E   A   Q   R   N   K   K   K   K   K   K   V   S   C

TTT TCC AAC ATC AAG ATC TTC CTG GTG TCC GAG TGC GCC CTG             336
 F   S   N   I   K   I   F   L   V   S   E   C   A   L

ATG CTG GCG CAG GGC ACG GTG GGC GCC TAC CTG GTG AGC GTC             378
 M   L   A   Q   G   T   V   G   A   Y   L   V   S   V

CTG ACC ACC CTG GAG CGT AGG TTC AAC CTG CAG AGC GCT GAC             420
 L   T   T   L   E   R   R   F   N   L   Q   S   A   D

GTG GGT GTG ATC GCT AGC AGC TTC GAG ATC GGG AAC CTG GCG             462
 V   G   V   I   A   S   S   F   E   I   G   N   L   A

CTC ATC CTC TTC GTG AGC TAC TTC GGG GCA CGC GGG CAC CGG             504
 L   I   L   F   V   S   Y   F   G   A   R   G   H   R

CCG CGC CTG ATC GGC TGC GGC GGC ATC GTC ATG GCG CTG GGC             546
 P   R   L   I   G   C   G   G   I   V   M   A   L   G

GCG CTG CTG TCG GCG CTG CCC GAG TTC CTG ACC CAC CAG TAC             588
 A   L   L   S   A   L   P   E   F   L   T   H   Q   Y

AAG TAC GAG GCG GGC GAG ATC CGC TGG GGC GCC GAG GGC CGC             630
 K   Y   E   A   G   E   I   R   W   G   A   E   G   R

GAC GTC TGC GCA GCC AAC GGC TCG GGC GGC GAC GAG GGG CCC             672
 D   V   C   A   A   N   G   S   G   G   D   E   G   P
```

```
GAC CCC GAC CTC ATC TGC CGC AAC CGG ACG GCT ACC AAC ATG      714
 D   P   D   L   I   C   R   N   R   T   A   T   N   M

ATG TAC TTG CTG CTC ATT GGG GCC CAG GTG CTC CTG GGC ATC      756
 M   Y   L   L   L   I   G   A   Q   V   L   L   G   I

GGT GCT ACC CCT GTG CAG CCC CTG GGC GTC TCC TAC ATC GAC      798
 G   A   T   P   V   Q   P   L   G   V   S   Y   I   D

GAC CAC GTG CGG AGG AAG GAC TCC TCG CTC TAT ATA GGA ATC      840
 D   H   V   R   R   K   D   S   S   L   Y   I   G   I

CTG TTC ACG ATG CTG GTA TTT GGA CCA GCC TGC GGG TTT ATC      882
 L   F   T   M   L   V   F   G   P   A   C   G   F   I

CTG GGC TCT TTC TGT ACC AAA ATC TAC GTG GAT GCG GTC TTC      924
 L   G   S   F   C   T   K   I   Y   V   D   A   V   F

ATT GAC ACA AGT AAC CTG GAC ATC ACT CCG GAC GAC CCC CGC      966
 I   D   T   S   N   L   D   I   T   P   D   D   P   R

TGG ATC GGA GCC TGG TGG GGT GGC TTT CTG CTC TGC GGT GCC     1008
 W   I   G   A   W   W   G   G   F   L   L   C   G   A

TTA CTC TTC TTC TCT TCC CTC TTG ATG TTT GGG TTT CCA CAG     1050
 L   L   F   F   S   S   L   L   M   F   G   F   P   Q

TCC CTG CCC CCG CAC TCA GAC CCC GCC ATG GAA AGC GAG CAG     1092
 S   L   P   P   H   S   D   P   A   M   E   S   E   Q

GCC ATG CTC TCC GAA AGA GAA TAC GAG AGA CCC AAG CCC AGC     1134
 A   M   L   S   E   R   E   Y   E   R   P   K   P   S

AAC GGG GTC CTG AGG CAC CCC CTG GAG CCA GAC AGC AGT GCC     1176
 N   G   V   L   R   H   P   L   E   P   D   S   S   A

TCC TGT TTC CAG CAG CTG AGA GTG ATC CCG AAG GTC ACC AAG     1218
 S   C   F   Q   Q   L   R   V   I   P   K   V   T   K

CAC CTG CTC TCA AAC CCT GTG TTC ACC TGC ATC ATC CTG GCC     1260
 H   L   L   S   N   P   V   F   T   C   I   I   L   A

GCC TGC ATG GAG ATT GCA GTG GTG GCT GGC TTC GCT GCC TTT     1302
 A   C   M   E   I   A   V   V   A   G   F   A   A   F

TTG GGG AAG TAC CTG GAG CAG CAG TTT AAC CTC ACC ACC TCT     1344
 L   G   K   Y   L   E   Q   Q   F   N   L   T   T   S

TCT GCC AAC CAG CTG CTT GGG ATG ACT GCG ATC CCG TGT GCT     1386
 S   A   N   Q   L   L   G   M   T   A   I   P   C   A

TGT CTG GGT ATC TTC CTG GGA GGT CTT TTG GTG AAG AAG CTC     1428
 C   L   G   I   F   L   G   G   L   L   V   K   K   L

AGC CTG TCT GCC CTG GGG GCC ATT CGG ATG GCC ATG CTC GTC     1470
 S   L   S   A   L   G   A   I   R   M   A   M   L   V

AAC CTG GTG TCC ACT GCT TGC TAC GTC TCC TTC CTC TTC CTG     1512
 N   L   V   S   T   A   C   Y   V   S   F   L   F   L

GGC TGC GAC ACT GGC CCT GTG GCT GGG GTT ACT GTT CCC TAT     1554
 G   C   D   T   G   P   V   A   G   V   T   V   P   Y

GGA AAC AGC ACA GCA CCT GGC TCA GCC CTG GAC CCC TAC TCG     1596
 G   N   S   T   A   P   G   S   A   L   D   P   Y   S

CCC TGC AAT AAT AAC TGT GAA TGC CAA ACC GAT TCC TTC ACT     1638
 P   C   N   N   N   C   E   C   Q   T   D   S   F   T

CCA GTG TGT GGG GCA GAT GGC ATC ACC TAC CTG TCT GCC TGC     1680
 P   V   C   G   A   D   G   I   T   Y   L   S   A   C

TTT GCT GGC TGC AAC AGC ACG AAT CTC ACG GGC TGT GCG TGC     1722
 F   A   G   C   N   S   T   N   L   T   G   C   A   C

CTC ACC ACC GTC CCT GCT GAG AAC GCA ACC GTG GTT CCT GGA     1764
 L   T   T   V   P   A   E   N   A   T   V   V   P   G

AAA TGC CCC AGT CCT GGG TGC CAA GAG GCC TTC CTC ACT TTC     1806
```

```
          K   C   P   S   P   G   C   Q   E   A   F   L   T   F
CTC TGT GTG ATG TGT ATC TGC AGC CTG ATC GGT GCC ATG GCA          1848
 L   C   V   M   C   I   C   S   L   I   G   A   M   A

CAG ACA CCC TCA GTC ATC ATC CTC ATC AGG ACA GTC AGC CCT          1890
 Q   T   P   S   V   I   I   L   I   R   T   V   S   P

GAA CTC AAG TCT TAC GCT TTG GGA GTT CTT TTT CTC CTC CTT          1932
 E   L   K   S   Y   A   L   G   V   L   F   L   L   L

CGT TTG TTG GGC TTC ATC CCT CCA CCC CTC ATC TTC GGG GCT          1974
 R   L   L   G   F   I   P   P   P   L   I   F   G   A

GGC ATC GAC TCC ACC TGC CTG TTC TGG AGC ACG TTC TGT GGG          2016
 G   I   D   S   T   C   L   F   W   S   T   F   C   G

GAG CAA GGC GCC TGC GTC CTC TAC GAC AAT GTG GTC TAC CGA          2058
 E   Q   G   A   C   V   L   Y   D   N   V   V   Y   R

TAC CTG TAT GTC AGC ATC GCC ATC GCG CTC AAA TCC TTC GCC          2100
 Y   L   Y   V   S   I   A   I   A   L   K   S   F   A

TTC ATC CTG TAC ACC ACC ACG TGG CAG TGC CTG AGG AAA AAC          2142
 F   I   L   Y   T   T   T   W   Q   C   L   R   K   N

TAT AAA CGC TAC ATC AAA AAC CAC GAG GGC GGG CTG AGC ACC          2184
 Y   K   R   Y   I   K   N   H   E   G   G   L   S   T

AGT GAG TTC TTT GCC TCT ACT CTG ACC CTA GAC AAC CTG GGG          2226
 S   E   F   F   A   S   T   L   T   L   D   N   L   G

AGG GAC CCT GTG CCC GCA AAC CAG ACA CAT AGG ACA AAG TTT          2268
 R   D   P   V   P   A   N   Q   T   H   R   T   K   F

ATC TAT AAC CTG GAA GAC CAT GAG TGG TGT GAA AAC ATG GAG          2310
 I   Y   N   L   E   D   H   E   W   C   E   N   M   E

TCC GTT TTA TAG TGACTAAAGG AGGGCTGAAC TCTGTATTAG TAATCCAAGG      2362
 S   V   L   *

GTCATTTTTT TCTTAAAAAA AGAAAAAAAG GTTCCAAAAA AAACCAAAAC           2412

TCAGTACACA CACACAGGCA CAGATGCACA CACACGCAGA CAGACACACC           2462

GACTTTGTCC TTTTTCTCAG CATCAGAGCC AGACAGGATT CAGAATAAGG           2512

AGAGAATGAC ATCGTGCGGC AGGGTCCTGG AGGCCACTCG CGCGGCTGGG           2562

CCACAGAGTC TACTTTGAAG GCACCTCATG GTTTTCAGGA TGCTGACAGC           2612

TGCAAGCAAC AGGCACTGCC AAATTCAGGG AACAGTGGTG GCCAGCTTGG           2662

AGGATGGACA TTTCTGGATA CACATACACA TACAAAACAG AAAACATTTT           2712

TTAAAAGAAG TTTCCTAAAA TAAAAAAAAT AAAAAAAAAA AAAAA                2757
```

OATP-RP4 (SEQ ID NOS:7 and 8) (Nucleotide 713, designated Y, can be either a C (in which case the encoded amino acid X is Leu) or a T (in which case the encoded amino acid X is Phe); Nucleotide 2397, designated K, can be either a G (in which case the encoded amino acid X is Gly) or a T (in which case the encoded amino acid X is Val)):

```
                     CTGATTTCTC TTCGGCTGGA CGGAGGCTGC CTCCTCACGC GGCTCCCAAC    50

TATTCCCGTA GCTCAGTGCC CCCCTCCCGC CGCTCTACTC AGCCAGGCAG   100

ACAGACTGAC AGACTCGCTA GTCGGCAGCT TCACTCCCGA GGGTGCCGCG   150

AGCCCAGGCG GCGAACACCC GGTACCCCTG GCGCAGCGAG GTGGGATGCT   200

GTACGGACAG CAGCGCTAAG TGCCCCCCCA CCCCCGGCGC AGGGTGCACT   250

CGCTCCTGGC CGCGGGCCCA GCGGCGGCGG CGGCGGCGGC GGCGGAGGGG   300

ATGAGCCCGG GACGCGCGAG GCGCCTGCCT CAAGCTACCG CCCGGAGAGG   350

GACGCCGAGT AGGGCTCATC GCAGTACCGC GCGGACCCCT GCCCCCTGTG   400
```

-continued

```
GCACGCGGCT GCGGAGCCTT GAAGCCGTGT CTGTGATCAG GATGCACTGG         450

GCGCCTCGCA GCTGGTGAGG ATGCCCTGCT GCGCGGCCCT GCGCCCCCAG         500

CCCCAGTCCC AGGTGGGCAA GACTGACTGG GCCCGGCTTC GGCCCCTCGT         550

GCCGGTGGAT GAAACGTGCC GGAGTGCTTG GGTGCCATCA GCTATCAAAT         600

CTGAATTCTA AGCGCC ATG GAC GAA GGC ACT GGA CTG CAG CCC GGG     646
               M   D   E   G   T   G   L   Q   P   G

GCG GGA GAG CAG CTG GAG GCG CCG GCC ACT GCA GAA GCT GTC        688
 A   G   E   Q   L   E   A   P   A   T   A   E   A   V

CAA GAG AGG TGC GAG CCG GAG ACC YTC AGG TCT AAG AGT TTA        730
 Q   E   R   C   E   P   E   T   X   R   S   K   S   L

CCG GTC CTC AGC AGC GCC TCC TGC CGG CCA AGC CTC AGT CCC        772
 P   V   L   S   S   A   S   C   R   P   S   L   S   P

ACT AGT GGA GAC GCC AAC CCG GCC TTT GGC TGT GTG GAT TCT        814
 T   S   G   D   A   N   P   A   F   G   C   V   D   S

TCG GGC CAC CAG GAG TTG AAG CAA GGC CCG AAC CCG TTG GCC        856
 S   G   H   Q   E   L   K   Q   G   P   N   P   L   A

CCC AGT CCC TCT GCC CCG TCC ACT TCG GCG GGG CTC GGG GAC        898
 P   S   P   S   A   P   S   T   S   A   G   L   G   D

TGT AAC CAC AGG GTG GAC CTC AGC AAA ACC TTC TCG GTG TCC        940
 C   N   H   R   V   D   L   S   K   T   F   S   V   S

TCC GCC TTG GCC ATG CTC CAG GAG AGA AGG TGC CTC TAC GTG        982
 S   A   L   A   M   L   Q   E   R   R   C   L   Y   V

GTC CTC ACG GAT TCC CGT TGC TTC CTG GTG TGC ATG TGC TTT       1024
 V   L   T   D   S   R   C   F   L   V   C   M   C   F

CTG ACC TTC ATC CAG GCG TTA ATG GTC TCT GGG TAC CTG AGC       1066
 L   T   F   I   Q   A   L   M   V   S   G   Y   L   S

AGC GTA ATT ACC ACC ATT GAA AGG CGC TAC AGT CTG AAG AGT       1108
 S   V   I   T   T   I   E   R   R   Y   S   L   K   S

TCC GAG TCG GGG CTG CTG GTC AGC TGC TTT GAC ATC GGG AAC       1150
 S   E   S   G   L   L   V   S   C   F   D   I   G   N

CTG GTG GTG GTG GTG TTC GTC AGC TAC TTC GGC GGC CGG GGT       1192
 L   V   V   V   V   F   V   S   Y   F   G   G   R   G

CGG CGG CCC CTG TGG CTG GCC GTG GGT GGA CTC CTC ATC GCC       1234
 R   R   P   L   W   L   A   V   G   G   L   L   I   A

TTC GGG GCA GCC CTC TTC GCC TTA CCT CAC TTC ATC TCG CCC       1276
 F   G   A   A   L   F   A   L   P   H   F   I   S   P

CCC TAC CAG ATC CAA GAG TTG AAC GCC TCG GCC CCC AAC GAC       1318
 P   Y   Q   I   Q   E   L   N   A   S   A   P   N   D

GGC CTG TGT CAG GGT GGC AAC TCC ACC GCC ACT TTG GAG CCT       1360
 G   L   C   Q   G   G   N   S   T   A   T   L   E   P

CCG GCC TGT CCG AAG GAC TCG GGA GGA AAT AAT CAC TGG GTC       1402
 P   A   C   P   K   D   S   G   G   N   N   H   W   V

TAC CTG GCT TTA TTC ATT TGC GCG CAG ATT CTC ATT GGA ATG       1444
 Y   L   A   L   F   I   C   A   Q   I   L   I   G   M

GGC TCC ACA CCT ATT TAT ACC CTG GGA CCA ACC TAC TTA GAT       1486
 G   S   T   P   I   Y   T   L   G   P   T   Y   L   D

GAC AAT GTC AAG AAA GAA AAC TCC TCC TTG TAC CTA GCC ATC       1528
 D   N   V   K   K   E   N   S   S   L   Y   L   A   I

ATG TAT GTC ATG GGA GCA CTT GGC CCT GCA GTG GGA TAT TTA       1570
 M   Y   V   M   G   A   L   G   P   A   V   G   Y   L

TTA GGT GGA CTT CTT ATT GGT TTT TAT GTT GAT CCC AGA AAT       1612
 L   G   G   L   L   I   G   F   Y   V   D   P   R   N
```

-continued

```
CCT GTT CAC CTT GAC CAG AAT GAC CCT CGT TTC ATT GGA AAC    1654
 P   V   H   L   D   Q   N   D   P   R   F   I   G   N

TGG TGG AGT GGA TTC CTC CTT TGT GCC ATT GCA ATG TTT CTT    1696
 W   W   S   G   F   L   L   C   A   I   A   M   F   L

GTG ATA TTC CCA ATG TTT ACT TTC CCA AAA AAG CTT CCA CCT    1738
 V   I   F   P   M   F   T   F   P   K   K   L   P   P

CGA CAC AAG AAA AAG AAA AAG AAA AAA TTT TCT GTT GAT GCT    1780
 R   H   K   K   K   K   K   K   K   F   S   V   D   A

GTT AGT GAT GAC GAT GTT CTG AAG GAG AAA TCA AAC AAC AGT    1822
 V   S   D   D   D   V   L   K   E   K   S   N   N   S

GAA CAA GCG GAC AAA AAA GTT TCT TCG ATG GGA TTT GGA AAG    1864
 E   Q   A   D   K   K   V   S   S   M   G   F   G   K

GAT GTC AGA GAC CTA CCA AGA GCA GCT GTC AGG ATC TTA AGC    1906
 D   V   R   D   L   P   R   A   A   V   R   I   L   S

AAC ATG ACA TTC CTT TTT GTG AGT TTG TCA TAC ACA GCT GAG    1948
 N   M   T   F   L   F   V   S   L   S   Y   T   A   E

AGT GCC ATT GTA ACT GCT TTC ATT ACC TTC ATT CCC AAG TTC    1990
 S   A   I   V   T   A   F   I   T   F   I   P   K   F

ATC GAG TCA CAG TTT GGT ATC CCA GCC TCC AAT GCC AGC ATC    2032
 I   E   S   Q   F   G   I   P   A   S   N   A   S   I

TAC ACT GGG GTT ATT ATC GTC CCC AGT GCT GGT GTT GGT ATT    2074
 Y   T   G   V   I   I   V   P   S   A   G   V   G   T

GTC CTC GGA GGC TAC ATT ATA AAA AAA TTG AAA CTT GGT GCC    2116
 V   L   G   G   Y   I   I   K   K   L   K   L   G   A

AGA GAA TCT GCA AAA CTA GCA ATG ATC TGC AGT GGT GTG TCT    2158
 R   E   S   A   K   L   A   M   I   C   S   G   V   S

TTA CTA TGT TTT TCA ACC CTA TTT ATT GTT GGA TGT GAA AGC    2200
 L   L   C   F   S   T   L   F   I   V   G   C   E   S

ATT AAT CTA GGG GGC ATA AAC ATC CCT TAT ACA ACA GGA CCT    2242
 I   N   L   G   G   I   N   I   P   Y   T   T   G   P

TCT CTC ACC ATG CCC CAT AGG AAT CTG ACA GGA AGC TGC AAC    2284
 S   L   T   M   P   H   R   N   L   T   G   S   C   N

GTT AAT TGT GGT TGT AAA ATA CAC GAG TAT GAG CCA GTC TGT    2326
 V   N   C   G   C   K   I   H   E   Y   E   P   V   C

GGA TCA GAT GGA ATT ACA TAC TTT AAC CCT TGT CTG GCT GGC    2368
 G   S   D   G   I   T   Y   F   N   P   C   L   A   G

TGT GTT AAT AGT GGT AAT CTT AGC ACT GKG ATA CGG AAT TAT    2410
 C   V   N   S   G   N   L   S   T   X   I   R   N   Y

ACA GAA TGC ACC TGT GTC CAA AGT CGC CAA GTG ATC ACT CCA    2452
 T   E   C   T   C   V   Q   S   R   Q   V   I   T   P

CCC ACC GTG GGA CAG CGA AGT CAG CTC CGT GTG GTT ATT GTC    2494
 P   T   V   G   Q   R   S   Q   L   R   V   V   I   V

AAG ACT TAT CTC AAT GAG AAC GGC TAT GCT GTG TCT GGG AAA    2536
 K   T   Y   L   N   E   N   G   Y   A   V   S   G   K

TGT AAA CGG ACC TGC AAT ACT CTT ATC CCA TTC TTA GTT TTT    2578
 C   K   R   T   C   N   T   L   I   P   F   L   V   F

CTT TTC ATA GTC ACC TTC ATC ACA GCA TGT GCC CAA CCA TCA    2620
 L   F   I   V   T   F   I   T   A   C   A   Q   P   S

GCT ATC ATA GTA ACA CTC AGG TCC GTA GAA GAT GAG GAG AGA    2662
 A   I   I   V   T   L   R   S   V   E   D   E   E   R

CCT TTT GCA CTG GGA ATG CAG TTT GTT TTG TTG CGA ACA CTT    2704
 P   F   A   L   G   M   Q   F   V   L   L   R   T   L

GCA TAC ATT CCT ACT CCA ATC TAC TTT GGA GCA GTC ATT GAC    2746
```

-continued

```
          A   Y   I   P   T   P   I   Y   F   G   A   V   I   D
ACC ACC TGC ATG CTC TGG CAA CAG GAA TGT GGT GTG CAG GGT         2788
 T   T   C   M   L   W   Q   Q   E   C   G   V   Q   G

TCT TGC TGG GAG TAC AAC GTG ACG TCG TTT CGT TTT GTG TAT         2830
 S   C   W   E   Y   N   V   T   S   F   R   F   V   Y

TTT GGT TTG GCT GCC GGC CTC AAA TTC GTT GGG TTT ATT TTT         2872
 F   G   L   A   A   G   L   K   F   V   G   F   I   F

ATT TTT CTG GCC TGG TAC TCC ATA AAA TAC AAG GAG GAT GGA         2914
 I   F   L   A   W   Y   S   I   K   Y   K   E   D   G

CTG CAG AGG CGG AGG CAG AGA GAA TTT CCC CTG AGC ACC GTG         2956
 L   Q   R   R   R   Q   R   E   F   P   L   S   T   V

AGT GAG AGA GTG GGA CAC CCC GAC AAT GCC CGG ACT AGA TCT         2998
 S   E   R   V   G   H   P   D   N   A   R   T   R   S

TGC CCA GCT TTC AGC ACC CAG GGA GAA TTC CAC GAA GAG ACT         3040
 C   P   A   F   S   T   Q   G   E   F   H   E   E   T

GGC CTG CAA AAA GGG ATC CAG TGC GCA GCA CAG ACC TAC CCG         3082
 G   L   Q   K   G   I   Q   C   A   A   Q   T   Y   P

GGG CCC TTC CCA GAA GCA ATA AGT TCC TCT GCG GAC CCG GGG         3124
 G   P   F   P   E   A   I   S   S   S   A   D   P   G

CTG GAA GAG AGC CCC GCT GCC TTG GAG CCG CCC TCC TGA             3163
 L   E   E   S   P   A   A   L   E   P   P   S   *

AGCTTGAAAA TGGAAGAATT TAGTTTTGTT GGTTGAATTG AAAATGGCGA          3213

CTTGAGAAAC AACTGTGCCT TCTTTTCTTT CTTTCTTTTT TTTAACCTCT          3263

ACAGACACAA TCCTCAAACC AACAAAACTC AGTATACACA GCCGCTATTC          3313

ATTGAGGGCT GGATACCTCA ACAAGACTGA GAGCCTTTCC CCGCTTCTCT          3363

CCAAGAAGGA GACGTTCAGC TAGATTTGTT CCCATTTCCG TTGTGTTAAT          3413

TCAAAGCTCA TGCTCCCCTA CGGTACAGGC TGAGGTACAC GGTTAGCAAA          3463

ACCATGGGAA GGGGAATGGC GGTGCATATC ATTAACTAAC ACTCCAAACA          3513

AAGGTGAGCT TGCCCAGGAC TTGGCATTTC CAAATCAAAG TTTTTAGATA          3563

TGAACACCTA CTGTGAGTTC TGCTACAAAG CACAAATGAA TTTGTCTCAA          3613

CTATGCAATT TGATTGGAAA AATGTATGTG CAGCATGTTA CATTTACTTT          3663

CACGGAATAA AGCAGATATG TTTCTGAAA                                 3692
```

OATP-RP5 (SEQ ID NOS:9 and 10):

```
CGCAAAGAAA TGGCTCAAAA GCTTCAGCTC TTTCTGTGCC CTGGGAGCTG           50

AGATGCACGT CAGTGGCCTT GCCAGCGTGG CCAATTCTCT GCTGACTGCC          100

AGAAAAAAGA GGCCAGGAAG AAAGAGGAAA GAGAAGAGAT CGCTCAGGGG          150

TGAGACCATG CCCTTCATCT TTTCTTTTCC CTAATCTCCT CTGCTTGTGT          200

CCACCCACAC TCTCCCCACC TGGCAAAATT GTTCAAAATT GCTGTGGAGT          250

TTACCTCAGT TTCCTCTTTC AGTCTGTGGT GTGTGGTCCA TCCTCTTGCT          300

GAGCACATTG AAAGGAACTG GCTATCTTTG ATCTCTTCCT CCAGATCAGA          350

GTCAAGGAAT GTGTTTATA ATG GAC ACT TCA TCC AAA GAA AAT ATC        396
                         M   D   T   S   S   K   E   N   I

CAG TTG TTC TGC AAA ACT TCA GTG CAA CCT GTT GGA AGG CCT         438
 Q   L   F   C   K   T   S   V   Q   P   V   G   R   P

TCT TTT AAA ACA GAA TAT CCC TCC TCA GAA GAA AAG CAA CCA         480
 S   F   K   T   E   Y   P   S   S   E   E   K   Q   P

TGC TGT GGT GAA CTA AAG GTG TTC TTG TGT GCC TTG TCT TTT         522
```

```
                    -continued
  C   C   G   E   L   K   V   F   L   C   A   L   S   F GTT TAC TTT GCC AAA GCA TTG GCA GAA GGC TAT CTG AAG AGC     564
 V   Y   F   A   K   A   L   A   E   G   Y   L   K   S ACC ATC ACT CAG ATA GAG AGA AGG TTT GAT ATC CCT TCT TCA     606
 T   I   T   Q   I   E   R   R   F   D   I   P   S   S CTG GTG GGA GTT ATT GAT GGT AGT TTT GAA ATT GGG AAT CTC     648
 L   V   G   V   I   D   G   S   F   E   I   G   N   L TTA GTT ATA ACA TTT GTT AGC TAC TTT GGA GCC AAA CTT CAC     690
 L   V   I   T   F   V   S   Y   F   G   A   K   L   H AGG CCA AAA ATA ATT GGA GCA GGG TGT GTA ATC ATG GGA GTT     732
 R   P   K   I   I   G   A   G   C   V   I   M   G   V GGA ACA CTG CTC ATT GCA ATG CCT CAG TTC TTC ATG GAG CAG     774
 G   T   L   L   I   A   M   P   Q   F   F   M   E   Q TAC AAA TAT GAG AGA TAT TCT CCT TCC TCC AAT TCC ACT CTC     816
 Y   K   Y   E   R   Y   S   P   S   S   N   S   T   L AGC ATC TCT CCG TGT CTC CTA GAG TCA AGC AGT CAA TTA CCA     858
 S   I   S   P   C   L   L   E   S   S   S   Q   L   P GTT TCA GTT ATG GAA AAA TCA AAA TCC AAA ATA AGT AAC GAA     900
 V   S   V   M   E   K   S   K   S   K   I   S   N   E TGT GAA GTG GAC ACT AGC TCT TCC ATG TGG ATT TAT GTT TTC     942
 C   E   V   D   T   S   S   S   M   W   I   Y   V   F CTG GGC AAT CTT CTT CGT GGA ATA GGA GAA ACT CCC ATT CAG     984
 L   G   N   L   L   R   G   I   G   E   T   P   I   Q CCT TTG GGC ATT GCC TAC CTG GAT GAT TTT GCC AGT GAA GAC    1026
 P   L   G   I   A   Y   L   D   D   F   A   S   E   D AAT GCA GCT TTC TAT ATT GGG TGT GTG CAG ACG GTT GCA ATT    1068
 N   A   A   F   Y   I   G   C   V   Q   T   V   A   I ATA GGA CCA ATC TTT GGT TTC CTG TTA GGC TCA TTA TGT GCC    1110
 I   G   P   I   F   G   F   L   L   G   S   L   C   A AAA CTA TAT GTT GAC ATT GGC TTT GTA AAC CTA GAT CAC ATA    1152
 K   L   Y   V   D   I   G   F   V   N   L   D   H   I ACC ATT ACC CCA AAA GAT CCC CAG TGG GTA GGA GCC TGG TGG    1194
 T   I   T   P   K   D   P   Q   W   V   G   A   W   W CTT GGC TAT CTA ATA GCA GGA ATC ATA AGT CTT CTT GCA GCT    1236
 L   G   Y   L   I   A   G   I   I   S   L   L   A   A GTG CCT TTC TGG TAT TTA CCA AAG AGT TTA CCA AGA TCC CAA    1278
 V   P   F   W   Y   L   P   K   S   L   P   R   S   Q AGT AGA GAG GAT TCT AAT TCT TCC TCT GAG AAA TCC AAG TTT    1320
 S   R   E   D   S   N   S   S   S   E   K   S   K   F ATT ATA GAT GAT CAC ACA GAC TAC CAA ACA CCC CAG GGA GAA    1362
 I   I   D   D   H   T   D   Y   Q   T   P   Q   G   E AAT GCA AAA ATA ATG GAA ATG GCA AGA GAT TTT CTT CCA TCA    1404
 N   A   K   I   M   E   M   A   R   D   F   L   P   S CTG AAG AAT CTT TTT GGA AAC CCA GTA TAC TTC CTA TAT TTA    1446
 L   K   N   L   F   G   N   P   V   Y   F   L   Y   L TGT ACA AGC ACT GTT CAG TTC AAT TCT CTG TTC GGC ATG GTG    1488
 C   T   S   T   V   Q   F   N   S   L   F   G   M   V ACG TAC AAA CCA AAG TAC ATT GAG CAG CAG TAT GGA CAG TCA    1530
 T   Y   K   P   K   Y   I   E   Q   Q   Y   G   Q   S TCC TCC AGG GCC AAC TTT GTG ATC GGG CTC ATC AAC ATT CCA    1572
 S   S   R   A   N   F   V   I   G   L   I   N   I   P GCA GTG GCC CTT GGA ATA TTC TCT GGG GGG ATA GTT ATG AAA    1614
 A   V   A   L   G   I   F   S   G   G   I   V   M   K
```

```
                                    -continued
AAA TTC AGA ATC AGT GTG TGT GGA GCT GCA AAA CTC TAC TTG    1656
 K   F   R   I   S   V   C   G   A   A   K   L   Y   L GGA TCA TCT GTC TTT GGT TAC CTC CTA TTT CTT TCC CTG TTT    1698
 G   S   S   V   F   G   Y   L   L   F   L   S   L   F GCA CTG GGC TGT GAA AAT TCT GAT GTG GCA GGA CTA ACT GTC    1740
 A   L   G   C   E   N   S   D   V   A   G   L   T   V TCC TAC CAA GGA ACC AAA CCT GTC TCT TAT CAT GAA CGA GCT    1782
 S   Y   Q   G   T   K   P   V   S   Y   H   E   R   A CTC TTT TCA GAT TGC AAC TCA AGA TGC AAA TGT TCA GAG ACA    1824
 L   F   S   D   C   N   S   R   C   K   C   S   E   T AAA TGG GAA CCC ATG TGC GGT GAA AAT GGA ATC ACA TAT GTA    1866
 K   W   E   P   M   C   G   E   N   G   I   T   Y   V TCA GCT TGT CTT GCT GGT TGT CAA ACC TCC AAC AGG AGT GGA    1908
 S   A   C   L   A   G   C   Q   T   S   N   R   S   G AAA AAT ATT ATA TTT TAC AAC TGC ACT TGT GTG GGA ATT GCA    1950
 K   N   I   I   F   Y   N   C   T   C   V   G   I   A GCT TCT AAA TCC GGA AAT TCC TCA GGC ATA GTG GGA AGA TGT    1992
 A   S   K   S   G   N   S   S   G   I   V   G   R   C CAG AAA GAC AAT GGA TGT CCC CAA ATG TTT CTG TAT TTC CTT    2034
 Q   K   D   N   G   C   P   Q   M   F   L   Y   F   L GTA ATT TCA GTC ATC ACA TCC TAT ACT TTA TCC CTA GGT GGC    2076
 V   I   S   V   I   T   S   Y   T   L   S   L   G   G ATA CCT GGA TAC ATA TTA CTT CTG AGG TGC ATT AAG CCA CAG    2118
 I   P   G   Y   I   L   L   L   R   C   I   K   P   Q CTT AAG TCT TTT GCC TTG GGT ATC TAC ACA TTA GCA ATA AGA    2160
 L   K   S   F   A   L   G   I   Y   T   L   A   I   R GTT CTT GCA GGA ATC CCA GCT CCA GTG TAT TTT GGA GTT TTG    2202
 V   L   A   G   I   P   A   P   V   Y   F   G   V   L ATT GAT ACT TCA TGC CTC AAA TGG GGA TTT AAA AGA TGT GGA    2244
 I   D   T   S   C   L   K   W   G   F   K   R   C   G AGT AGA GGA TCA TGC AGA TTA TAT GAT TCA AAT GTC TTC AGA    2286
 S   R   G   S   C   R   L   Y   D   S   N   V   F   R CAT ATA TAT TTG GGA CTA ACT GTG ATA CTG GGC ACA GTG TCA    2328
 H   I   Y   L   G   L   T   V   I   L   G   T   V   S ATT CTC CTA AGC ATT GCA GTA CTT TTC ATT TTA AAG AAA AAT    2370
 I   L   L   S   I   A   V   L   F   I   L   K   K   N TAT GTT TCA AAA CAC AGA AGT TTT ATA ACC AAG AGA GAA AGA    2412
 Y   V   S   K   H   R   S   F   I   T   K   R   E   R ACA ATG GTG TCT ACA AGA TTC CAA AAG GAA AAT TAC ACT ACA    2454
 T   M   V   S   T   R   F   Q   K   E   N   Y   T   T AGT GAT CAT CTG CTA CAA CCC AAC TAC TGG CCA GGC AAG GAA    2496
 S   D   H   L   L   Q   P   N   Y   W   P   G   K   E

ACT CAA CTT TAG AAACATGATG ACTGGAAGTC ATGTCTTCTA           2538
 T   Q   L   *

ATTGGTTGAC ATTTTGCAAA CAAATAAATT GTAATCAAAA GAGCTCTAAA     2588

TTTGTAATTT CTTTCTCCTT TCAAAAAATG TCTACTTTGT TTTGGTCCTA     2638

GGCATTAGGT AATATAACTG ATAATATACT GAAATATATA ATGGAAGATG     2688

CAGATGATAA AACTAATTTT GAACTTTTTA ATTTATATAA ATTATTTTAT     2738

ATCATTTACT TATTTCACTT TATTTTGCTT TGTGCTCATT GATATATATT     2788

AGCTGTACTC CTAGAAGAAC AATTGTCTCT ATTGTCACAC ATGGTTATAT     2838

TTAAAGTAAT TTCTGAACTG TGTAATGTGT CTAGAGTAAG CAAATACTGC     2888
```

-continued

```
TAACAATTAA CTCATACCTT GGGTTCCTTC AAGTATTACT CCTATAGTAT    2938

TTTCTCCCAT AGCTGTCTTC ATCTGTGTAT TTTAATAATG ATCTTAGGAT    2988

GGAGCAGAAC ATGGAGAGGA AGATTTCATT TTAAGCTCCT CCTTTTCCTT    3038

GAAATACAAT AATTTATATA GAAATGTGTA GCAGCAAATT ATATTGGGGA    3088

TTAGAATTTT GAATTAATAG CTCTCCTACT ATTAATTTAC ATGTGCTTTT    3138

TGTGTGGCGC TATAAGTGAC TATGGTTGTA AAGTAATAAA ATTGATGTTA    3188

ACATGCCCAA TTATTGTTCT TTTATGAATT CAATGAATTT AAAACTATTG    3238

TTAAATATAA TACTGCCCCA CTTTAATATA TGTAAGCAAC TTCCTACTTA    3288

TACACGACGT GTTCCTAAAA CATGTTTGAA AGGTGAATTT CTGAAAGTCT    3338

CCCATAAATG TAGGTGTTAC AACAGGAAAA AAAAAAAAAA AAA          3381
```

OATP-RP1 (SEQ ID NOS:11 and 12):

```
                                  GGCACGAG GCGCTGCGCG       18

GCGCGGCGGC CGGGCCCTCG AGACGGGAC GGACACACCA GCCCCTCGGA     68

TACCACTTGG CCACTCCCGC TGAGGCCACT CCCACTGCGT GGCTGAAGCC    118

TCGAGGTCAC CAGGCGGAGG CGCGGAG ATG CCC CTG CAT CAG CTG GGG 166
                                M   P   L   H   Q   L   G

GAC AAG CCG CTC ACC TTC CCC AGC CCC AAC TCA GCC ATG GAA   208
 D   K   P   L   T   F   P   S   P   N   S   A   M   E

AAC GGG CTT GAC CAC ACC CCA CCC AGC AGG AGG GCA TCC CCG   250
 N   G   L   D   H   T   P   P   S   R   R   A   S   P

GGC ACA CCC CTG AGC CCC GGG TCC CTC CGC TCC GCT GCC CAT   292
 G   T   P   L   S   P   G   S   L   R   S   A   A   H

AGC CCC CTG GAC ACC AGC AAG CAG CCC CTC TGC CAG CTC TGG   334
 S   P   L   D   T   S   K   Q   P   L   C   Q   L   W

GCC GAG AAG CAT GGC GCC CGG GGG ACC CAT GAG GTG CGG TAC   376
 A   E   K   H   G   A   R   G   T   H   E   V   R   Y

GTC TCG GCC GGG CAG AGC GTG GCG TGC GGC TGG TGG GCC TTC   418
 V   S   A   G   Q   S   V   A   C   G   W   W   A   F

GCA CCG CCG TGC CTG CAG GTC CTC AAC ACG CCC AAG GGC ATC   460
 A   P   P   C   L   Q   V   L   N   T   P   K   G   I

CTG TTC TTC CTG TGT GCG GCC GCA TTC CTG CAG GGG ATG ACT   502
 L   F   F   L   C   A   A   A   F   L   Q   G   M   T

GTG AAT GGC TTC ATC AAC ACA GTC ATC ACC TCC CTG GAG CGC   544
 V   N   G   F   I   N   T   V   I   T   S   L   E   R

CGC TAT GAC CTG CAC AGC TAC CAG AGC GGG CTC ATC GCC AGC   586
 R   Y   D   L   H   S   Y   Q   S   G   L   I   A   S

TCC TAC GAC ATT GCC GCC TGC CTC TGC CTC ACC TTC GTC AGC   628
 S   Y   D   I   A   A   C   L   C   L   T   F   V   S

TAC TTC GGG GGC TCA GGG CAC AAG CCG CGC TGG CTG GGC TGG   670
 Y   F   G   G   S   G   H   K   P   R   W   L   G   W

GGC GTG CTG CTT ATG GGC ACG GGG TCG CTG GTG TTC GCG CTG   712
 G   V   L   L   M   G   T   G   S   L   V   F   A   L

CCC CAC TTC ACG GCT GGC CGC TAT GAG GTG GAG TTG GAC GCG   754
 P   H   F   T   A   G   R   Y   E   V   E   L   D   A

GGT GTC AGG ACG TGC CCT GCC AAC CCC GGC GCG GTG TGT GCG   796
 G   V   R   T   C   P   A   N   P   G   A   V   C   A

GAC AGC ACC TCG GGC CTG TCC CGC TAC CAG CTG GTC TTC ATG   838
 D   S   T   S   G   L   S   R   Y   Q   L   V   F   M

CTG GGC CAG TTC CTG CAT GGC GTG GGT GCC ACA CCC CTC TAC   880
```

-continued

```
        L    G    Q    F    L    H    G    V    G    A    T    P    L    Y
ACG CTG GGC GTC ACC TAC CTG GAT GAG AAC GTC AAG TCC AGC           922
 T   L   G   V   T   Y   L   D   E   N   V   K   S   S

TGC TCG CCC GTC TAC ATT GCC ATC TTC TAC ACA GCG GCC ATC           964
 C   S   P   V   Y   I   A   I   F   Y   T   A   A   I

CTG GGC CCA GCT GCC GGC TAC CTG ATT GGA GGT GCC CTG CTG          1006
 L   G   P   A   A   G   Y   L   I   G   G   A   L   L

AAT ATC TAC ACG GAA ATG GGC CGA CGG ACG GAG CTG ACC ACC          1048
 N   I   Y   T   E   M   G   R   R   T   E   L   T   T

GAG AGC CCA CTG TGG GTC GGC GCC TGG TGG GTC GGC TTC CTG          1090
 E   S   P   L   W   V   G   A   W   W   V   G   F   L

GGC TCT GGG GCC GCT GCT TTC TTC ACC GCC GTT CCC ATC CTT          1132
 G   S   G   A   A   A   F   F   T   A   V   P   I   L

GGT TAC CCT CGG CAG CTG CCA GGC TCC CAG CGC TAC GCG GTC          1174
 G   Y   P   R   Q   L   P   G   S   Q   R   Y   A   V

ATG AGA GCG GCG GAA ATG CAC CAG TTG AAG GAC AGC AGC CGT          1216
 M   R   A   A   E   M   H   Q   L   K   D   S   S   R

GGG GAG GCG AGC AAC CCG GAC TTT GGG AAA ACC ATC AGA GAC          1258
 G   E   A   S   N   P   D   F   G   K   T   I   R   D

CTG CCT CTC TCC ATC TGG CTC CTG CTG AAG AAC CCC ACG TTC          1300
 L   P   L   S   I   W   L   L   L   K   N   P   T   F

ATC CTG CTC TGC CTG GCC GGG GCC ACC GAG GCC ACT CTC ATC          1342
 I   L   L   C   L   A   G   A   T   E   A   T   L   I

ACC GGC ATG TCC ACG TTC AGC CCC AAG TTC TTG GAG TCC CAG          1384
 T   G   M   S   T   F   S   P   K   F   L   E   S   Q

TTC AGC CTG AGT GCC TCA GAA GCT GCC ACC TTG TTT GGG TAC          1426
 F   S   L   S   A   S   E   A   A   T   L   F   G   Y

CTG GTG GTG CCA GCG GGT GGT GGC GGC ACC TTC CTG GGC GGC          1468
 L   V   V   P   A   G   G   G   G   T   F   L   G   G

TTC TTT GTG AAC AAG CTC AGG CTC CGG GGC TCC GCG GTC ATC          1510
 F   F   V   N   K   L   R   L   R   G   S   A   V   I

AAG TTC TGC CTG TTC TGC ACC GTT GTC AGC CTG CTG GGC ATC          1552
 K   F   C   L   F   C   T   V   V   S   L   L   G   I

CTC GTC TTC TCA CTG CAC TGC CCC AGT GTG CCC ATG GCG GGC          1594
 L   V   F   S   L   H   C   P   S   V   P   M   A   G

GTC ACA GCC AGC TAC GGC GGG AGC CTC CTG CCC GAA GGC CAC          1636
 V   T   A   S   Y   G   G   S   L   L   P   E   G   H

CTG AAC CTA ACG GCT CCC TGC AAC GCT GCC TGC AGC TGC CAG          1678
 L   N   L   T   A   P   C   N   A   A   C   S   C   Q

CCA GAA CAC TAC AGC CCT GTG TGC GGC TCG GAC GGC CTC ATG          1720
 P   E   H   Y   S   P   V   C   G   S   D   G   L   M

TAC TTC TCA CTG TGC CAC GCA GGG TGC CCT GCA GCC ACG GAG          1762
 Y   F   S   L   C   H   A   G   C   P   A   A   T   E

ACG AAT GTG GAC GGC CAG AAG GTG TAC CGA GAC TGT AGC TGT          1804
 T   N   V   D   G   Q   K   V   Y   R   D   C   S   C

ATC CCT CAG AAT CTT TCC TCT GGT TTT GGC CAT GCC ACT GCA          1846
 I   P   Q   N   L   S   S   G   F   G   H   A   T   A

GGG AAA TGC ACT TCA ACT TGT CAG AGA AAG CCC CTC CTT CTG          1888
 G   K   C   T   S   T   C   Q   R   K   P   L   L   L

GTT TTC ATA TTC GTT GTA ATT TTC TTT ACA TTC CTC AGC AGC          1930
 V   F   I   F   V   V   I   F   F   T   F   L   S   S

ATT CCT GCA CTA ACG GCA ACT CTA CGA TGT GTC CGT GAC CCT          1972
 I   P   A   L   T   A   T   L   R   C   V   R   D   P
```

```
                        -continued
CAG AGA TCC TTT GCC CTG GGA ATC CAG TGG ATT GTA GTT AGA      2014
 Q   R   S   F   A   L   G   I   Q   W   I   V   V   R ATA CTA GGG GGC ATC CCG GGG CCC ATC GCC TTC GGC TGG GTG      2056
 I   L   G   G   I   P   G   P   I   A   F   G   W   V ATC GAC AAG GCC TGT CTG CTG TGG CAG GAC CAG TGT GGC CAG      2098
 I   D   K   A   C   L   L   W   Q   D   Q   C   G   Q CAG GGC TCC TGC TTG GTG TAC CAG AAT TCG GCC ATG AGC CGC      2140
 Q   G   S   C   L   V   Y   Q   N   S   A   M   S   R TAC ATA CTC ATC ATG GGG CTC CTG TAC AAG GTG CTG GGC GTC      2182
 Y   I   L   I   M   G   L   L   Y   K   V   L   G   V CTC TTC TTT GCC ATA GCC TGC TTC TTA TAC AAG CCC CTG TCG      2224
 L   F   F   A   I   A   C   F   L   Y   K   P   L   S GAG TCT TCA GAT GGC CTG GAA ACT TGT CTG CCC AGC CAG TCC      2266
 E   S   S   D   G   L   E   T   C   L   P   S   Q   S TCA GCC CCT GAC AGT GCC ACA GAT AGC CAG CTC CAG AGC AGC      2308
 S   A   P   D   S   A   T   D   S   Q   L   Q   S   S

GTC TGA CCACCGCCCG CGCCCACCCG GCCACGGCGG GCACTCAGCA          2354
 V   *

TTTCCTGATG ACAGAACAGT GCCGTTGGGT GATGCAATCA CACGGGAACT       2404

TCTATTTGAC CTGCAACCTT CTACTTAACC TGTGGTTTAA AGTCGGCTGT       2454

GACCTCCTGT CCCCAGAGCT GTACGGCCCT GCAGTGGGTG GGAGGAACTT       2504

GCATAAATAT ATATTTATGG ACACACAGTT TGCATCAGAA CGTGTTTATA       2554

GAATGTGTTT TATACCCGAT CGTGTGTGGT GTGCGTGAGG ACAAACTCCG       2604

CAGGGGCTGT GAATCCCACT GGGAGGGCGG CGGGCCTGCA GCCCGAGGAA       2654

GGCTTGTGTG TCCTCAGTTA AAACTGTGCA TATCGAAATA TATTTTGTTA       2704

TTTAAGCCTG CGAAAAAAAA AAAAAAAAAA AAAAAAAAAA AAAAAAAAAA       2754

AAAAAAAAAA                                                   2763
```

Persons skilled in the art can also modify the nucleic acids coding for the OATPs of the present invention to prepare useful mutations. For example, one may modify the sequence to provide additional restriction endonuclease recognition sites in the nucleic acid. Such mutations may be silent or may change the amino acid encoded by the mutated codon. One can prepare these modified nucleic acids, for example, by mutating the nucleic acid coding for an OATP of the present invention to result in deletion, substitution, insertion, inversion or addition of one or more amino acids in the encoded polypeptide. For methods of site-directed mutagenesis, see Taylor, J. W. et al. (1985), Nucl. Acids Res. 13, 8749–64 and Kunkel, J. A. (1985), Proc. Natl. Acad. Sci. USA 82: 482–92. In addition, kits for site-directed mutagenesis are available from commercial vendors (e.g., BioRad Laboratories, Richmond, Calif.; Amersham Corp., Arlington Heights, Ill.). For disruption, deletion and truncation methods, see Sayers, J. R. et al. (1 988), Nucl. Acids Res. 16: 791–800.

This invention also comprises modified nucleic acids, including (1) alternative splice exon variants; (2) allelic variants; and (3) chimeric proteins in which the fusion construct comprises an OATP or fragment thereof. Such modified nucleic acids can be obtained by persons of ordinary skill in the art when armed with the present disclosure.

Expression Vectors

This invention further concerns expression vectors comprising a nucleotide sequence encoding an OATP of the present invention. Preferably, the expression vectors comprise all or a portion of the nucleic acid sequence as shown in SEQ ID NO:1, SEQ ID NO:3, SEQ ID NO:5, SEQ ID NO:7, SEQ ID NO:9, or SEQ ID NO:11; preferred is a nucleotide sequence encoding an OATP as shown above (i.e., the coding region).

Expression vectors are usually plasmids, but the invention includes other vector forms that serve equivalent functions and become known in the art subsequently hereto. A person skilled in the art might also stably integrate a sequence encoding an OATP into the chromosome of an appropriate host cell.

Expression vectors typically contain regulatory elements capable of affecting expression of an OATP. These regulatory elements can be heterologous or native OATP elements. Typically, a vector contains an origin of replication, a promoter, and a transcription termination sequence. The vector may also include other regulatory sequences, including mRNA stability sequences, which provide for stability of the expression product; secretory leader sequences, which provide for secretion of the expression product; environmental feedback sequences, which allow expression of the structural gene to be modulated (e.g., by the presence or absence of nutrients or other inducers in the growth medium); marking sequences, which are capable of providing phenotypic selection in transformed host cells; restriction sites, which provide sites for cleavage by restriction endonucleases; and sequences which allow expression in various types of hosts, including prokaryotes, yeasts, fungi, plants and higher eukaryotes.

An expression vector of this invention is at least capable of directing the replication, and preferably the expression, of the nucleic acids and protein of this invention. Suitable origins of replication include, for example, the Col E1, the SV40 viral, Epstein Barr viral, and the M13 origins of replication. Suitable promoters include, for example, the cytomegalovirus promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like.

Persons skilled in the art may insert DNA encoding An OATP of the present invention into several commercially available vectors. Examples include vectors compatible with mammalian cells, such as pcDNA3 or pCEP4; baculovirus vectors such as pBlueBac; prokaryotic vectors such as pcDNA2; and yeast vectors such as pYes2. For vector modification techniques, see Sambrook et al. (1989), *Molecular Cloning: A Laboratory Manual*, Second Edition, Cold Spring Harbor Laboratory, Cold Spring Harbor, N.Y.

Host Cells

This invention additionally concerns host cells containing an expression vector that comprises a sequence encoding an OATP, preferably the OATP2, OATP-RP2, OATP-RP3, OATP-RP4, OATP-RP5 or OATP-RP1 of the present invention. The host cells preferably contain an expression vector which comprises all or part of the DNA sequence having the nucleotide sequence substantially as shown in SEQ ID NO:1, SEQ ID NO:3, SEQ ID NO:5, SEQ ID NO:7, SEQ ID NO:9, or SEQ ID NO:11, particularly the coding regions thereof. Suitable host cells include both prokaryotic cells (e.g., *E. coli* strains HB101, DH5a, XL1 Blue, Y1090 and JM101) and eukaryotic cells (e.g., *Spodoptera frugiperda* insect cells, CHO cells, COS-7 cells, HEK 293 cells, human skin fibroblasts, and *S. cerevisiae* cells).

Persons skilled in the art may introduce expression vectors into host cells by various methods known in the art. Exemplary methods are transfection by calcium phosphate precipitation, electroporation, liposomal fusion, nuclear injection, and viral or phage infection. One may then culture the host cell under conditions permitting expression of large amounts of OATP.

One may identify such modified host cells by any of five general approaches:

(a) DNA-DNA hybridization with probes complementary to the sequence encoding an OATP (Southern blotting).

(b) detection of marker gene functions, such as thymidine kinase activity, resistance to antibiotics, and the like. A marker gene can be placed in the same plasmid as an OATP sequence under the regulation of the same or a different promoter.

(c) detection of mRNA transcripts by hybridization assays (e.g., Northern blotting or a nuclease protection assay using a probe complementary to the RNA sequence).

(d) immunodetection of gene expression (e.g., by Western blotting with antibody to OATP).

(e) PCR with primers homologous to expression vector sequences or sequences encoding OATP. The PCR produces a DNA fragment of predicted length, indicating incorporation of the expression system in the host cell.

Persons skilled in the art may determine DNA sequences by various known methods. See, for example, the dideoxy chain termination method in Sanger et al. (1977), *Proc. Natl. Acad. Sci. USA* 74: 5463–7 and the Maxam-Gilbert method in Maxam-Gilbert (1977), *Proc. Natl. Acad. Sci. USA* 74: 560–4.

One may use the host cells of this invention in a variety of ways that are now apparent. One may use the cells to screen for compounds that bind to or otherwise modulate or regulate the function of an OATP of the present invention, which would be useful for modulation, for example activation or inactivation, of OATP2, OATP-RP2, OATP-RP3, OATP-RP4, OATP-RP5 or OATP-RP1 activity; to study signal transduction mechanisms and protein-protein interactions; and to prepare OATP for the uses described below.

Not all expression vectors and DNA regulatory sequences will function equally well to express the DNA sequences of this invention. Neither will all host cells function equally well with the same expression system. However, one of ordinary skill in the art may make a selection among expression vectors, DNA regulatory sequences, and host cells using the guidance provided herein without undue experimentation and without departing from the scope of the invention.

Polypeptides

This invention further concerns polypeptides comprising all or a portion of the amino acid sequences of OATPs of the present invention. The inventors prefer polypeptides comprising all or a portion of the amino acid sequences shown as in SEQ ID NO:2 (OATP2), SEQ ID NO:4 (OATP-RP2), SEQ ID NO:6 (OATP-RP3), SEQ ID NO:8 (OATP-RP4), SEQ ID NO:10 (OATP-RP5) or SEQ ID NO:12 (OATP-RP1). Where a portion of an OATP of the present invention is used, preferably the portion exhibits the same biological activity of the OATP from which the portion is derived. For example, and within the scope of the invention, are polypeptides that comprise all or a portion of OATP2, OATP-RP2, OATP-RP3, OATP-RP4, OATP-RP5 or OATP-RP1 that exhibit transport activity. The portions may contain one or more mutations so that the protein(s) fail(s) to exhibit transport activity, but that can be used to screen for compounds that will modulate or bind to the protein or portion thereof.

Persons having ordinary skill in the art may prepare these polypeptides by methods known in the art. For example, one may use chemical synthesis, such as the solid phase procedure described by Houghton et al. (1985), *Proc. Natl. Acad. Sci.* 82: 5131–5. Another method is in vitro translation of mRNA. One may also produce the polypeptides in the above-described host cells, which is the preferred method. For example, one may synthesize DNA comprising all or a portion of SEQ ID NO:1, SEQ ID NO:3, SEQ ID NO:5, SEQ ID NO:7, SEQ ID NO:9, or SEQ ID NO:11 by PCR as described above, insert the synthesized DNA into an expression vector, transform a host cell with the expression vector, and culture the host cell to produce the desired polypeptides.

Persons skilled in the art can isolate and purify such polypeptides by any one of several known techniques; for example, ion exchange chromatography, gel filtration chromatography and affinity chromatography. Such techniques may require modification of the protein. For example, one may add a histidine tag to the protein to enable purification on a nickel column.

Persons skilled in the art can use the polypeptides of the invention in a wide variety of ways. For example, one may use them to generate polyclonal or monoclonal antibodies. One may then use such antibodies for immunodetection (e.g., radioimmunoassay, enzyme immunoassay, or immunocytochemistry), immunopurification (e.g., affinity chromatography) of polypeptides from various sources, or immunotherapy.

Persons skilled in the art may make modified OATP polypeptides by known techniques. Such modifications may cause higher or lower activity, permit higher levels of protein production, or simplify purification of the protein. Such modifications may help identify specific OATP amino acids involved in binding, which in turn may help rational drug design of OATP modulators. One can make amino acid substitutions based on similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. All such modified polypeptides are included within the scope of the invention.

Preferred analogs include proteins that differ from the novel OATPs of the present invention (or biologically active fragments thereof) by one or more conservative amino acid substitutions or by one or more non-conservative amino acid substitutions, deletions or insertions which do not abolish the biological activity of the analog. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

The inventors contemplate a number of other variations of the above-described polypeptides. Such variations include salts and esters of the polypeptides, as well as precursors of the aforementioned polypeptides (e.g., having N-terminal substituents such as methionine, N-formylmethionine and leader sequences). The invention includes all such variations.

Method for Detecting Nucleic Acids

The present invention further concerns a method for detecting nucleic acids encoding OATP proteins. In this method, a person of ordinary skill in the art (a) contacts nucleic acids of unknown sequence with a nucleic acid having a sequence complementary to a known coding sequence (e.g., a sequence of at least about 10 nucleotides from, e.g., SEQ ID NO:1, SEQ ID NO:3, SEQ ID NO:5, SEQ ID NO:7, SEQ ID NO:9, or SEQ ID NO:11, particularly the coding regions thereof), wherein the latter nucleic acid has a detectable marker; and (b) determines the presence of marker bound to any of the nucleic acids of unknown sequence. The presence of bound marker indicates the presence of the desired nucleic acids. One can apply this method to detect OATP nucleic acids from other tissues (which may have different regulatory elements) and nucleic acids from other species (e.g., monkey).

Persons of ordinary skill in the art generally know how to obtain nucleic acids to be analyzed in this method. For genomic DNA, one can rapidly freeze tissue, crush the tissue into readily digestible pieces, and incubate the crushed tissue in proteinase K and SDS to degrade most cellular proteins. One can then deproteinize the genomic DNA by successive phenol/chloroform/isoamyl alcohol extractions, recover DNA by ethanol precipitation, dry it and resuspend it in buffer. For RNA, one can lyse cultured cells in 4M guanidinium solution, draw the lysate through a 20-gauge needle, pellet the RNA through a cesium chloride step gradient, and remove the supernatant. The pellet should contain purified RNA.

The detectable marker may be a radioactive ion linked to one of the nucleotides of the complementary nucleic acid. Common radioactive labels are $^{32}P$ and $^{35}S$, although one may also use other labels such as biotin. Persons skilled in the art are aware of various methods to attach the labels to the complementary nucleic acid (e.g., the random primer method for attachment of $^{32}P$ or $^{35}S$).

Persons of ordinary skill in the art generally know how to carry out such a method of detecting nucleic acids. For example, one may perform a Southern or northern blot using a radiolabeled OATP complementary oligonucleotide probe. One can then detect hybridization by autoradiography. Depending on the marker, one may also use other detection methods (e.g., spectrophotometry).

Methods for Detecting OATP Modulators and Compounds Transported by the OATPs of the Present Invention This invention further concerns methods for detecting modulators of the OATPs of the present invention, as well as methods for detecting compounds that are transported by the OATPs of the present invention (e.g., compounds that are transported into the liver that may be used as carriers for other compounds). A screen for OATP modulators entails detecting binding of molecules (e.g., polypeptides, natural products, synthetic compounds) in cells expressing OATP protein. Alternatively, a screen for OATP positive modulators and/or negative modulators entails detecting the augmentation and/or inhibition of transport of a known compound. A screen for OATP-transported compounds entails detecting the transport of molecules (e.g., polypeptides, natural products, synthetic compounds) by an OATP.

Cloning and sequencing of the OATPs of the present invention enables construction of cells useful in screening for natural products and synthetic compounds that bind to, modulate, and/or are transported by OATP activity. A process for detecting OATP modulators requires transforming a suitable vector into compatible host cells as described previously herein. One treats such transformed cells with test substances (e.g., synthetic compounds or natural products), and then measures activity in the presence and absence of the test substance.

OATP Assay

An assay for the measurement of OATP activity is performed as follows: HEK293 cells are plated in Dulbeccos Modified Eagles Medium (DMEM) plus 10% fetal bovine serum plus penecillin and streptomycin, in poly-d-lysine coated dishes and co-transfected with OATP transporter expression plasmids using Lipofectamine Plus (Life Technologies, Inc.). The cells and media are assayed for substrate transport 24 hours later. Alternatively, cell lines engineered to stably express OATPs could be plated and assayed directly without transfection. To measure transport, media is removed and monolayers are assayed in triplicate by washing once in serum-free DMEM and adding the same medium containing [$^3$H]-substrate alone or in the presence of various concentrations of unlabeled test compounds. For OATP2, the [$^3$H]-substrate could be [$^3$H]-pravastatin, [$^3$H]-taurocholate, or [$^3$H]-dehydroepiandrosterone sulfate, or [$^{125}$I]-thyroid hormone (T4). Monolayers are incubated at room temperature for 5 to 10 minutes depending on the transporter. Then the cells are rapidly washed once with ice cold DMEM containing 5% BSA, twice with DMEM plus 0.1% BSA and once with DMEM alone. Cells are lysed in 0.1 N NaOH and a fraction of the lysate is used to determine radiolabel incorporation by liquid scintillation counting, and another is used to determine protein concentration in the lysate using the Bradford assay with BSA as a standard. The transport activity is expressed as moles of substrate transported into cells/mg of cell protein/minute.

Drug Targeting

Also included within the present invention is tissue expression of an OATP of the present invention. The OATPs of the present invention are also useful for targeting drugs to certain organs that express an OATP described herein (e.g., the liver), and for modulating the concentration of endogenous substrates.

For example, the novel organic anion transporter disclosed herein, OATP2, represents a potential therapeutic target due to its ability to modulate the cellular uptake and potential secretion of a several biologically important organic anions, including bile acids and the androgen hormone dehydroepiandrosterone sulfate ("DHEAS"). Furthermore, since OATP2 transports at least one drug (i.e. pravastatin), and other members of this family are known to transport a variety of other xenobiotics, this transporter could be exploited to optimize the delivery of drugs into liver and away from other tissues.

OATP2 is unique among the OATP family, in that it is the only known organic anion transporter that is expressed exclusively in the liver. Thus, drugs optimized for this transporter could be targeted for hepatic delivery with greater selectivity than with any other known transporter. To generalize this approach, it may be possible to identify a small molecule "adaptor" that is efficiently recognized and transported by OATP2 (an OATP2-transported compound) that could be appended to other drugs for hepatic targeting even if the parent compound is not transported by OATP2.

Alternatively, if a therapeutic compound is taken up into the liver entirely or substantially by OATP2, one could inhibit hepatic clearance and thereby elevate circulating concentrations, or increase the compounds half-life in the periphery, by adding a functionality to said compound that disallows transport by OATP2. Likewise, if an endogenous substance utilizes OATP2 for liver uptake and clearance from the circulation, a competitive or non-competitive OATP2 inhibitor could elevate plasma levels of said substance. As an example, DHEAS is an adrenal androgen that declines with age and on the basis of some animal data, it has been suggested that replacement of DHEAS deficiency may stimulate age-related immune deficiencies, increase cognitive function and insulin sensitivity, and maintain bone mass. Inhibiting the hepatic clearance of endogenous DHEAS through blocking its interactions with OATP2 could result in elevated hormone levels in the absence of hormone supplementation.

With the information provided herein, one skilled in the art is able to identify molecules, both naturally occurring and synthetic (including therapeutic drugs), that are transported by the OATPs, e.g., OATP2, disclosed herein. OATPs as a class generally exhibit broad substrate specificity ("polyspecific" transporters). Thus, it is anticipated that many additional substrates of these transporters will be identified.

Gene Therapy

Persons skilled in the art can also use sense and antisense nucleic acid molecules as therapeutic agents for OATP-related indications. One may construct vectors that direct the synthesis of the desired DNA or RNA or formulate the nucleic acid as described in the art.

Several references describe the usefulness of antisense molecule. See Toulme and Helene (1988), Gene 72: 51–8; Inouye (1988), Gene, 72: 25–34; Uhlmann and Peyman (1990), Chemical Reviews 90: 543–584; Biotechnology Newswatch (Jan. 15, 1996), p. 4; Robertson, Nature Biotechnology 15: 209 (1997); Gibbons and Dzau (1996), Science 272: 689–93. One can design them based on genomic DNA and/or cDNA, 5' and 3' flanking control regions, other flanking sequences, intron sequences, and nonclassic Watson and Crick base pairing sequences used in formation of triplex DNA. Such antisense molecules include antisense oligodeoxyribonucleotides, oligoribonucleotides, oligonucleotide analogues, and the like, and may comprise at least about 15 to 25 bases.

Antisense molecules may bind noncovalently or covalently to the OATP DNA or RNA. Such binding could, for example, cleave or facilitate cleavage of OATP DNA or RNA, increase degradation of nuclear or cytoplasmic mRNA, or inhibit transcription, translation, binding of trans-activating factors, or pre-mRNA splicing or processing. Antisense molecules may also contain additional functionalities that increase stability, transport into and out of cells, binding affinity, cleavage of the target molecule, and the like. All of these effects would decrease expression of OATP protein and thus make the antisense molecules useful as OATP modulators.

EXAMPLES

The following examples are included for understanding the present invention and are not intended to limit the scope of Applicants invention, which is defined solely by the claims.

Example 1
Isolation of OATP2, OATP-RP1, OATP-RP2, OATP-RP3, OATP-RP4 and OATP-RP5 Full Length cDNAs and Cloning into Mammalian Expression Vectors Human OATP2 was identified by searching the public EST databases for sequences homologous to human OATP. One EST sequence, Genbank accession number T73863, encoded a partial cDNA with significant sequence identity with OATP. EST sequences encoding partial cDNAs for OATP-RP1, OATP-RP2, OATP-RP3, OATP-RP4, and OATP-RP5 were identified by searching the public EST databases and the Incyte, Inc. EST database for sequences homologous to human OATP. The EST clone IDs corresponding to OATP-RP1 are 820117, 2668489, 1610706, 2972518, and 588148. These clones represent a contig encoding only part of the full length cDNA. The Incyte EST clone IDs corresponding to OATP-RP2 are 1664737 and 2641944. These clones represent a contig encoding only part of the full length cDNA. The Incyte EST clone IDs corresponding to OATP-RP3 are 2493241, 2497845, and 2664024. These clones represent a contig encoding only part of the full length cDNA. The Incyte EST clone IDs corresponding to OATP-RP4 are 1494683 and 1685219. These clones represent a contig encoding only part of the full length cDNA. The Incyte EST clone ID corresponding to OATP-RP5 is 925716. This clone encodes only part of the full length cDNA. Full length clones for each of the above genes were obtained using the Gene Trapper cDNA Positive Selection System (LifeTechnologies, Inc.). In this procedure, a single or multiple oligonucleotides complementary to each of the EST contigs or individual EST sequences, were biotinylated at the 3'-end and used to hybridize to a single-stranded human cDNA library constructed in pCMVSport2 (LifeTechnologies, Inc.). The sequence of oligonucleotides used for each gene as well as the tissue source of the libraries screened are shown in Table 2.

Hybrids between the biotinylated oligonucleotides and single-stranded cDNA were captured on streptavidin-coated paramagnetic beads. After washing, the captured single-stranded cDNA targets was released from the biotinylated oligonucleotides and converted to dsDNA by DNA polymerase using the corresponding unbiotinylated oligonucleotide. Following transformation and plating, several positive clones for each gene were identified by PCR analysis. Full-length cDNA clones were identified by sequencing. In the case of OATP-RP1, a partial cDNA was obtained by the above technique (pSP-RP1A). Another cDNA clone that was part of the OATP-RP1 contig was identified by searching the public EST databases (Genbank accession number AI027850). An EcoRI-NotI fragment of this clone containing the first 477 nucleotides of OATP-RP1 (SEQ ID NO:11) (obtained from Research Genetics, Inc.) was ligated to EcoRI-NotI digested pSP-RP1A to generate the full length sequence.

Two polymorphic positions were identified when sequencing multiple OATP-RP4 cDNA clones. Thus, nucleotide number 713 of SEQ ID NO:7 can be either a C, encoding Leu in SEQ ID NO:8, or a T, encoding a Phe in SEQ ID NO:8. Similarly, nucleotide number 2397 of SEQ ID NO:7 can be either a G, encoding a Gly in SEQ ID NO:8, or a T, encoding a Val in SEQ ID NO:8.

For expression studies, OATP2 cDNA was cloned into the expression vector pCEP4βR, a modified form of pCEP4 (Invitrogen, Inc.) in which the CMV promoter-driven expression cassette has been inverted, and used in transient transfections. To accomplish this, OATP2 cDNA in pCMVSport2, correponding to nucleotides 59 through 2361 of SEQ ID NO:1, was excised by digestion with KpnI and NotI. This fragment was cloned into KpnI-NotI digested pCEP4βR. This clone, pCEP-OATP2 was used for transient transfection expression studies.

Example 2
Tissue and Cellular Distribution of OATP2, OATP-RP1, OATP-RP2, OATP-RP4, and OATP-RP5

The tissue distribution of OATP2, OATP-RP1, OATP-RP2, OATP-RP4, and OATP-RP5 expression was determined by Northern blotting of poly A+RNA from a variety of human tissues (FIG. 1). Transporters of this family previously described in the literature, namely human OATP, rat oatp1, rat oatp2 and rat oatp3, are all expressed in liver, kidney and brain. All of the above transport bile acids as well as a variety of other substrates that are specific for subsets of these transporters. In contrast, the expression of OATP2, which also transports bile acids, is very hepato-specific; a major 3.2 kb and several minor hybridizing bands were observed only in RNA from liver and no other tissue. The specific cell types that express this transporter were examined by in situ hybridization of OATP2 riboprobe to human liver samples. Strong hybridization signal was seen localized to hepatocytes throughout the liver lobule with no significant difference in signal intensity among centrilobular, midzonal or periportal regions. No signal was observed in bile ducts, Kupffer cells, or blood vessels, nor in any cell types from human lung (data not shown).

TABLE 2

Oligonucleotides used to screen for OATP Full length cDNAs using Gene-Trapper Selection

| Gene | Biotinylated capture oligonucleotide(s) used | Seq ID number of oligonucleotide | Human cDNA library screened |
|---|---|---|---|
| OATP2 | 5'-ACCCTGTCTAGCAGGTTGCA-3' | 13 | liver |
| OATP-RP1 | 5'-CTGTCGGAGTCTTCAGATG-3' | 14 | brain |
| OATP-RP2 | 5'-TCCATCACAGCCTCCTACGC-3' | 15 | liver |
| OATP-RP3 | 5'-TGCCTCTACTCTGACCCTAG-3' | 16 | heart |
| OATP-RP4 | 5'-GGAGCAGTCATTGACACCAC-3' | 17 | heart |
|  | 5'-TGCTGGGAGTACAACGTGACG-3' | 18 |  |
|  | 5'-ACAAGGAGGATGGACTGCAG-3' | 19 |  |
| OATP-RP5 | 5'-CAGGAATCCCAGCTCCAGTG-3' | 20 | brain |
|  | 5'-GCTACAACCCAACTACTGGC-3' | 21 |  |
|  | 5'-GGGACTAACTGTGATACTGG-3' | 22 |  |

OATP-RP1 is expressed in nearly all tissues tested with highest abundance in skeletal muscle, lung, placenta, and heart. OATP-RP2 is ubiquitously expressed in all tissues tested. OATP-RP4 has a much more restricted pattern of expression with abundant transcipts in skeletal muscle and heart and much less in prostate and thymus. The expression of OATP-RP5 is likewise tissue specific, with brain and testes being the only sites where transcripts were detected.

Example 3
Expression of OATP2 in Transfected Cells

Figure 2C:
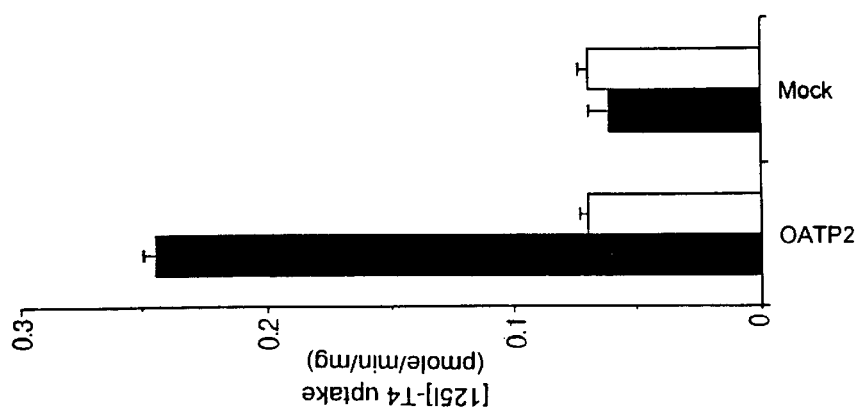
FIG. 2 shows that OATP2 transports pravastatin, dehydroepiandosterone sulfate (DHEAS), taurocholate and thyroid hormone (T).
FIG. 2A shows specific uptake of [$^3$H]-pravastatin and [$^3$H]-DHEAS.
FIG. 2B shows specific uptake of [$^3$H]-taurocholate. Panel 2C shows specific uptake of [125I]-thyroid hormone (T4). The uptake of radiolabeled substrate for 5 minutes into cells transfected with pCEPOATP-RP1 or empty vector (MOCK) was determined in the absence (solid bars) and presence (open bars) of excess unlabeled substrate.
Figure 2B:
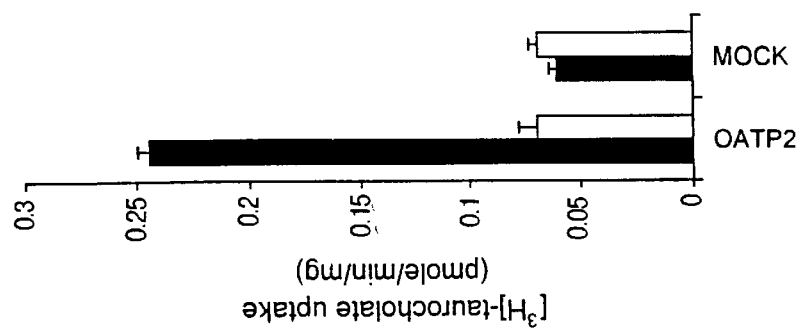
Figure 2A:
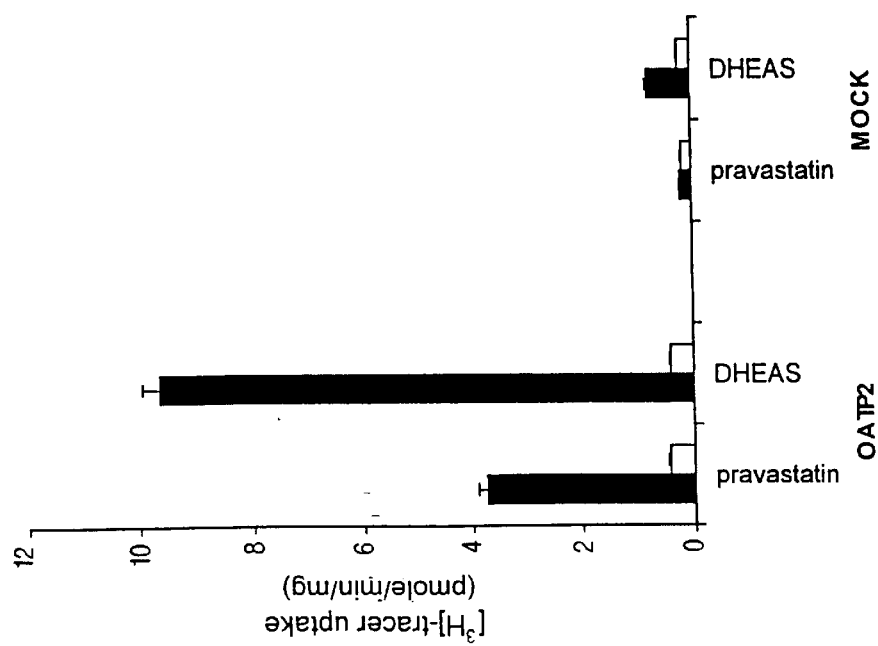

293EBNA cells (Invitrogen, Inc.), an HEK293 cell derivative, were transiently transfected with the OATP2 expression vector pCEP-OATP2, or the pCEP4 vector alone (MOCK) and the transport of [$^3$H]-labeled substrates was determined 24 hours later. FIG. 2A shows specific uptake of [$^3$H]-pravastatin and [$^3$H]-DHEAS. FIGS. 2B and 2C show the specific uptake of [$^3$H]-taurocholate and [125I]-thyroid hormone (T4), repsectively. The uptake of radiolabeled substrate for 5 minutes into cells transfected with pCEP-OATP2 or empty vector (MOCK) was determined in the absence (solid bars) and presence (open bars) of excess unlabeled substrate. Thus, OATP2 is a liver specific human transporter of at least some HMG CoA reductase inhibitors, bile acids, adrenal steroids, and thyroid hormone.

We claim:

1. A purified and isolated nucleic acid molecule encoding organic anion transport protein OATP2, wherein OATP2 has an amino acid sequence of SEQ ID NO:2, comprising anyone of:
   (a) the nucleic acid molecule of SEQ ID NO:1;
   (b) the coding region of (a); or
   (c) a nucleic acid molecule that differs from (a) or (b) due to degeneracy of the genetic code.

2. An expression vector comprising a nucleic acid molecule as claimed in claim 1 and an expression control sequence operatively linked to the nucleic acid molecule.

3. A host cell including an expression vector comprising a nucleic acid molecule as claimed in claim 1 and an expression control sequence operatively linked to the nucleic acid molecule, wherein said expression vector is capable of directing the expression of OATP2 protein.

4. A method of producing OATP2 protein, said method comprising the steps of:
   (a) inserting a nucleic acid molecule according to claim 1 encoding said OATP2 protein, into an appropriate expression vector,
   (b) introducing said expression vector into an appropriate host cell,
   (c) growing said host cells under conditions permitting expression of said OATP2 protein, and
   (d) purifying said OATP2 protein.

5. An isolated and purified nucleic acid molecule which hybridizes under stringent conditions to any one of:
   (a) the nucleic acid molecule of SEQ ID NO:1;
   (b) the coding region of (a);
   (c) the complement of (a);
   (d) the complement of (b); or
   (e) a nucleic acid molecule that differs from (a), (b), (c) or (d) due to degeneracy of the genetic code;
   wherein said nucleic acid molecule contains at least 300 contiguous nucleotides from either nucleotides 135–2207 of SEQ ID NO:1 or the complement of nucleotides 135–2207 of SEQ ID NO:1, and wherein said stringent conditions are Southern blotting washed in 0.1×SSC and 0.1% SDS at a temperature of at least about 65° C.

6. An isolated and purified nucleic acid molecule comprising the OATP2 gene, or a complement of the OATP2 gene, contained in ATCC Accession Number 207213.

7. An isolated purified nucleic acid molecule comprising anyone of:
   a) the complement of the nucleic acid molecule of SEQ ID NO:1;
   b) the complement of the nucleic acid molecule of the coding region of SEQ ID NO:1; or
   c) a nucleic acid molecule that differs from a) or b) due to degeneracy of the genetic code.

* * * * *